United States Patent [19]
Moberg
[11] Patent Number: 4,510,136
[45] Date of Patent: Apr. 9, 1985

[54] FUNGICIDAL 1,2,4-TRIAZOLE DERIVATIVES

[75] Inventor: William K. Moberg, Wilmington, Del.
[73] Assignee: E. I. Du Pont de Nemours and Company, Wilmington, Del.

[21] Appl. No.: 506,894
[22] Filed: Jun. 22, 1983

Related U.S. Application Data

[63] Continuation-in-part of Ser. No. 473,321, Mar. 15, 1983, abandoned, which is a continuation-in-part of Ser. No. 377,122, May 12, 1982, abandoned, which is a continuation-in-part of Ser. No. 349,261, Feb. 16, 1982, abandoned, which is a continuation-in-part of Ser. No. 276,986, Jun. 24, 1981, abandoned.

[51] Int. Cl.[3] .................... A61K 31/41; C07D 249/08
[52] U.S. Cl. .................................... 514/63; 548/110; 548/106; 548/101
[58] Field of Search ...................... 548/101, 106, 110; 424/184

[56] References Cited

U.S. PATENT DOCUMENTS

| | | | |
|---|---|---|---|
| 3,692,798 | 9/1972 | Barcza | 548/110 |
| 3,912,752 | 10/1975 | Meiser et al. | 424/269 |
| 4,248,992 | 2/1981 | Takago | 528/28 |

FOREIGN PATENT DOCUMENTS

| | | | |
|---|---|---|---|
| 785127 | 12/1972 | Belgium | 548/110 |
| 867245 | 11/1980 | Belgium . | |
| 29993 | 12/1979 | European Pat. Off. | 548/110 |
| 3000140 | 1/1980 | Fed. Rep. of Germany | 548/110 |
| 827703 | 10/1982 | South Africa | 546/14 |
| 271552 | 9/1970 | U.S.S.R. | 548/110 |
| 346306 | 10/1972 | U.S.S.R. | 548/110 |

*Primary Examiner*—Robert T. Bond
*Attorney, Agent, or Firm*—Gary H. Levin

[57] ABSTRACT

Silicon-containing 1,2,4-triazoles having broad-spectrum fungicidal activity have been discovered.

36 Claims, No Drawings

FUNGICIDAL 1,2,4-TRIAZOLE DERIVATIVES

RELATED APPLICATIONS

This application is a continuation-in-part of my copending application U.S. Ser. No. 473,321, filed Mar. 15, 1983, which is a continuation-in-part of my copending application U.S. Ser. No. 377,122, filed May 12, 1982, which is a continuation-in-part of my copending application U.S. Ser. No. 349,261, filed Feb. 16, 1982, which is a continuation-in-part of my copending application U.S. Ser. No. 276,986, filed June 24, 1981. All of these applications have now been abandoned.

BACKGROUND OF THE INVENTION

The present invention relates to silylmethyltriazoles, and, more particularly, this invention relates to silylmethyltriazoles such as dimethyl(phenyl)(1H-1,2,4-triazol-1-ylmethyl)silane, and to their use in controlling fungus diseases of living plants.

U.S. Pat. No. 3,692,798 discloses compounds of the formula:

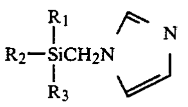

wherein $R_1$, $R_2$ and $R_3$ can be lower alkyl and phenyl. It is stated that these compounds are useful as anti-microbial agents.

European Pat. No. 29,993 discloses compounds of the formula:

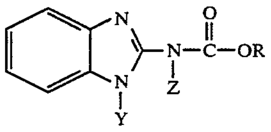

wherein R can be $C_1$–$C_4$ alkyl and Y and Z can be H or $SiR_1R_2R_3$, wherein $R_1$, $R_2$, and $R_3$ can be alkyl, haloalkyl, alkenyl, alkynyl, or substituted phenyl. It is taught that the compounds are useful as agricultural fungicides.

U.S. Pat. Nos. 3,256,308 and 3,337,598 disclose compounds of the formula:

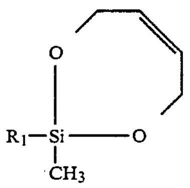

wherein $R_1$ can be methyl, ethyl, vinyl, or phenyl. Their use to control fungi is also taught.

Belgian Pat. No. 785,127 discloses quaternary ammonium salts such as:

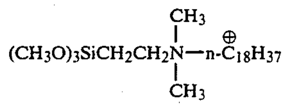

and their use as fungicides.

Research Disclosure 17,652 discloses silyl ethers of the formula:

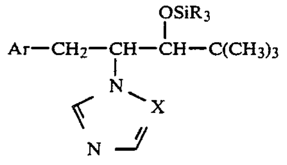

wherein Ar can be substituted phenyl, X can be CH or N, and R can be alkyl. It is taught that the compounds are useful as agricultural fungicides.

West German Pat. DE No. 3,000,140 discloses silyl ethers of the formula:

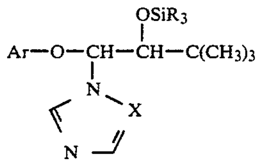

wherein Ar can be substituted phenyl, X can be CH or N, and R can be phenyl or lower alkyl. It is taught that these compounds are useful as agricultural fungicides.

U.S. Pat. No. 4,248,992 discloses guanidines of the formula:

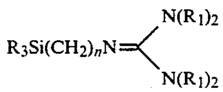

wherein R can be H, alkyl, or alkoxy and $R_1$ can be H or alkyl. It is taught that these compounds are useful as antifungal agents for molded plastics and rubbers.

U.S.S.R. Pat. No. 346,306 discloses silylmethylazoles of the formula:

$$(R_1)_n(R_2O)_{3-n}SiCH_2Az$$

wherein $R_1$ and $R_2$ are alkyl groups, n is 0–3, and Az is a pyrazole, imidazole, or benzimidazole ring, optionally substituted.

U.S.S.R. Pat. No. 271,552 discloses silylethylazoles of the formula:

$$(R_1)_n(R_2O)_{3-n}SiCH_2CH_2Az$$

wherein $R_1$, $R_2$, n, and Az are as described in the previous reference.

European Pat. No. 11,769 teaches that compounds of the general formula:

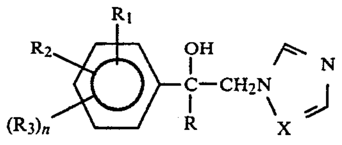

wherein

R is a substituted phenyl, naphthyl or tetrahydronaphthyl ring;

$R_1$ is a substituted phenyl or cycloalkyl ring;

$R_2$ is H, or together with $R_1$ it may form an annelated aryl or alkyl ring;

$R_3$ is halogen, alkyl, alkoxy or haloalkyl;

n is 0, 1, 2 or 3; and

X is CH or N, are useful as antimicrobial agents.

European Pat. No. 15,756 discloses compounds of the formula:

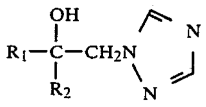

where $R_1$ is alkyl, cycloalkyl, or substituted phenyl; and $R_2$ is substituted phenyl or benzyl, and their use as agricultural fungicides.

European Pat. No. 36,133 discloses compounds of the formula:

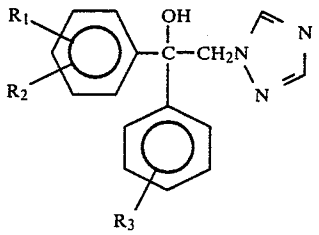

where $R_1$, $R_2$ and $R_3$ are H or Cl, provided that at least one of $R_1$ or $R_3$ is Cl, and their use as antimicrobials.

Belgian Pat. No. 867,245 discloses compounds of the formula:

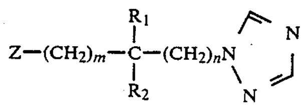

where

Z is aryl;

$R_1$ is CN, H, alkyl, cycloalkyl, alkenyl, cycloalkenyl, alkynyl, substituted aryl, or substituted aralkyl;

$R_2$ is H, alkyl, cycloalkyl, alkenyl, cycloalkenyl, alkynyl, substituted aryl, substituted aralkyl, alkoxy, alkenoxy, alkynoxy, OH, substituted aryloxy, or substituted aralkyloxy;

m is 0 or 1; and n is 1 or 2, and their use as agricultural fungicides.

SUMMARY OF THE INVENTION

This invention relates to novel compounds of Formula I, to agriculturally useful compositions of these compounds, and to the method of using these compounds to control plant fungus diseases.

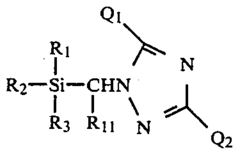

I wherein $Q_1$ and $Q_2$ are independently H or $CH_3$;

$R_1$ is $C_2$-$C_{18}$ alkyl, $C_3$-$C_6$ cycloalkyl, naphthyl, or

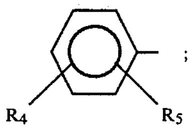

;

where $R_4$ and $R_5$ are independently —H, halogen, —$OCH_3$, —$OCF_3$, —$SCH_3$, —$SO_2CH_3$, phenyl, phenyl substituted with halogen and/or $C_1$-$C_4$ alkyl and/or —$CF_3$, phenoxy, phenoxy substituted with halogen and/or $C_1$-$C_4$ alkyl and/or —$CF_3$, —$CF_3$, $C_1$-$C_4$ alkyl, or cyclohexyl; and $R_2$ and $R_3$ are independently $C_1$-$C_6$ alkyl, $C_3$-$C_6$ cycloalkyl, $OR_6$, or

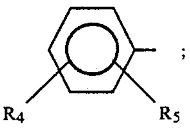

;

where $R_6$ is H, $C_1$-$C_4$ alkyl, or

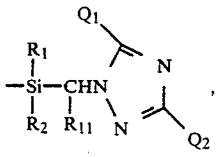

, with the proviso that when both $R_2$ and $R_3$ are $OR_6$, then $R_6$ must be $C_1$-$C_4$ alkyl; or $R_2$ and $R_3$ may be a 1,2- or 1,3- or 1,4-glycol bridge or a 1,4 unsaturated glycol bridge substituted by up to four alkyl groups $R_7$-$R_{10}$ that have a total of up to four carbon atoms

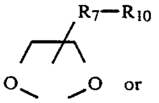

or

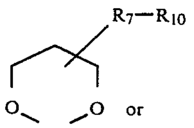

or

-continued

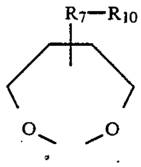 or 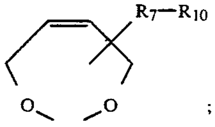 ; and and $R_{11}$ is H or $C_1$–$C_4$ alkyl.

This invention also relates to fungicidally active salts of compunds of Formula I with protic acids and complexes with metal ions.

Preferred for their high activity and/or favorable ease of synthesis are compounds of general formula I wherein $Q_1=Q_2=H$, and $R_{11}$ is H or $CH_3$.

More preferred for their higher activity and/or more favorable ease of synthesis are compounds of the preferred scope wherein $R_1$ is 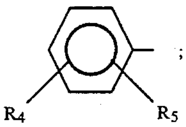 ;

and $R_2$ is $C_1$–$C_4$ alkyl or

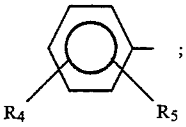 ;

and $R_3$ is $C_1$–$C_4$ alkyl or $OR_6$, where $R_6$ is H, $C_1$–$C_4$ alkyl or

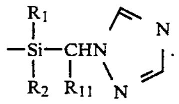

Most preferred for their highest activity and/or most favorable ease of synthesis are compounds of the more preferred scope wherein $R_1$ is 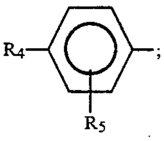 ;

where $R_4$ is at the para position of $R_1$, and $R_4$ is H, F, Cl, Br, or phenyl, and $R_5$ is H, F, Cl, or Br; and $R_2$ is

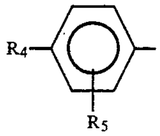

or $C_1$–$C_4$ alkyl; and $R_3$ is $C_1$–$C_4$ alkyl or $OR_6$, where $R_6$ is H, $C_1$–$C_4$ alkyl or

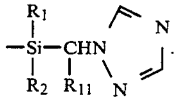

Specifically preferred for their excellent fungicidal activity and/or most favorable ease of synthesis are:

(1,1'-Biphenyl-4-yl)dimethyl(1H-1,2,4-triazol-1-ylmethyl)silane;

bis(4-Fluorophenyl)methyl(1H-1,2,4-triazol-1-ylmethyl)silane;

bis(4-Fluorophenyl)hydroxy(1H-1,2,4-triazol-1-ylmethyl)silane;

Oxybis[bis(4-fluorophenyl)(1H-1,2,4-triazol-1-ylmethyl)silane]; and bis(4-Fluorophenyl)methyl[1-(1H-1,2,4-triazol-1-yl)ethyl]silane.

When $Q_1$ and $Q_2$ are both H or both $CH_3$, the process for preparing the compounds of this invention produces a mixture of two triazole isomers:

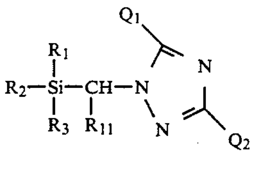 and 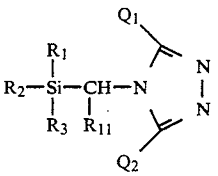

Formula IA Formula IB

Three isomers are possible when one triazole substituent is H and the other is $CH_3$;

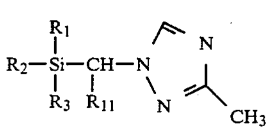 and 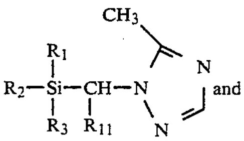 and

Formula IC Formula ID

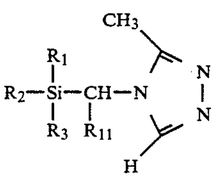

Formula IE

The mixture will contain predominately the isomers of Formula IA or Formula IC; however, the isomers of Formulae IB, ID, and IE also have fungicidal activity, and separation of the isomers is not required.

DETAILED DESCRIPTION OF THE INVENTION

Synthesis

The compounds of this invention wherein $R_{11}$ is H can be prepared from chloromethylsilanes and 1,2,4-triazole sodium salt or its monomethyl or dimethyl homologs:

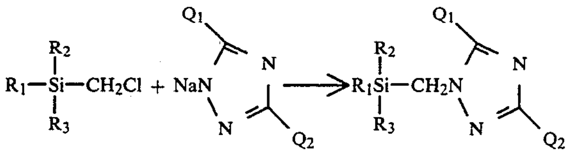

$Q_1, Q_2$ = H or $CH_3$

Lithium and potassium triazole salts may also be used. Bromomethylsilanes, iodomethylsilanes, or arylsulfonyloxymethylsilanes may be used instead of chloromethylsilanes. Roughly equimolar amounts of the reagents are used (except when $R_3{=}OR_6$; see below), with the triazole salt often taken in 5–10% excess of theory. In addition, 1,2,4-triazole itself can be used if an acid acceptor is added. Suitable acceptors include alkali metal alkoxides such as sodium methoxide or potassium tert-butoxide, inorganic bases such as potassium carbonate, or sodium hydride, and tertiary amines such as triethylamine. When the acid acceptor is a good nucleophile, such as sodium methoxide, an excess should be avoided to prevent undesired side reactions. Suitable solvents include polar aprotic solvents such as dimethylformamide, dimethyl sulfoxide, or acetonitrile; ethers such as tetrahydrofuran or 1,2-dimethoxyethane; and ketones such as 2-butanone. Non-polar solvents, for example aromatic hydrocarbons such as toluene, may also be used if a suitable phase transfer catalyst such as tetrabutylammonium hydrogen sulfate is added. The reaction temperature can vary between 0° and 200°, preferably between 25° and 100°. The reaction can be conducted under elevated pressure, but it is generally preferable to operate at atmospheric pressure. The optimum temperature and reaction time will vary with the concentration and choice of reagents, and especially with the choice of solvent. For example, 1,2,4-triazole and sodium methoxide at roughly 2 molar concentration in dimethylformamide gives good conversion in approximately 2 hours at 80°–90°, whereas 1,2,4-triazole and potassium carbonate at roughly 1 molar in 2-butanone requires 8–12 hours at reflux. In general, reaction times of 1 to 24 hours are required. Progress of the reaction can be followed by working up aliquots for nmr analysis and following the intensities of the starting material $SiCH_2Cl$ singlet near 2.9 and the product $SiCH_2N$ singlet near 3.8.

In the course of this reaction, the 1H-1,2,4-triazol-1-ylmethyl compound as prepared above is accompanied by a minor amount of the isomeric 4H-1,2,4-triazol-4-ylmethyl compound:

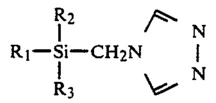

The ratio of isomers varies with values of R and reaction conditions, with a 1-substituted to 4-substituted ratio of roughly 10:1 often observed. The mono- and dimethyltriazoles give similar 4H-isomers as minor products:

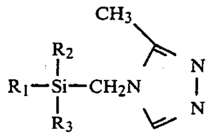
or
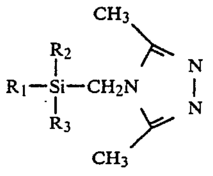

When the unsubstituted silylmethyltriazole is available, metalation-methylation provides an alternate synthesis of the methylated homologs:

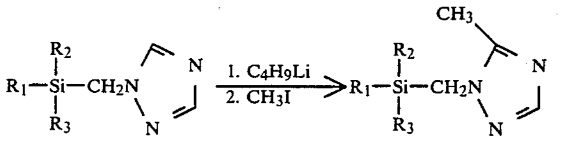

For the case where $R_3{=}OR_6$ in the product, the chlorines of a chloro(chloromethyl)silane can be replaced in one of two ways. In one method, at least two equivalents of 1,2,4-triazole sodium salt is used. An intermediate containing a very reactive silicon-triazole bond forms, and reaction with water or an alcohol gives the desired oxygenated compounds as shown in the following reaction sequence:

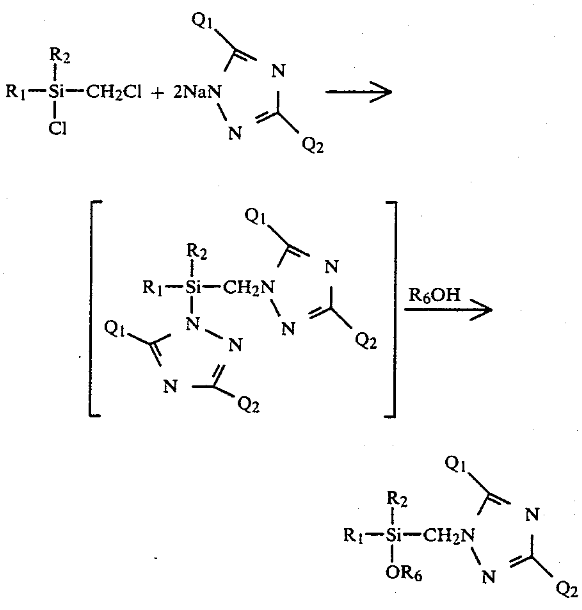

Suitable solvents and reaction conditions are the same as those outlined previously for triazole displacements. The temperature of alcoholysis is not critical, and warming to 50°–100° can be used to ensure complete reaction when $R_6{=}C_1$–$C_4$ alkyl. For $R_6{=}H$, however, hydrolysis is best conducted near room temperature to minimize disiloxane formation, recognizing that silanol-disiloxane equilibrium is possible whenever $R_6{=}H$:

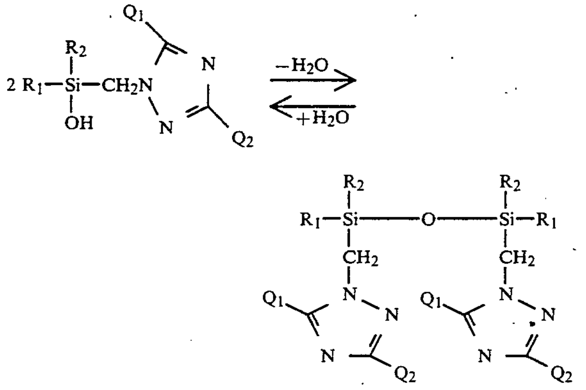

The position of equilibrium and the rate at which it is established will vary with the values of $R_1$ and $R_2$, solvent, temperature, and the presence or absence of acidic or basic catalysts.

In the second method, the silicon-oxygen bond is formed first, followed by triazole displacement as described earlier:

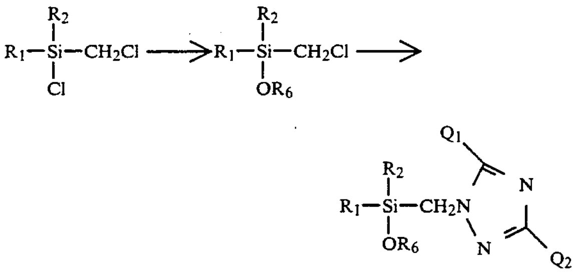

Reaction of the chlorosilane with $R_6OH$ may be conducted in almost any non-hydroxylic solvent, with ethers such as diethyl ether, 1,2-dimethoxyethane, and tetrahydrofuran or dipolar aprotic solvents such as dimethylformamide and acetonitrile being preferred. Although an acid acceptor is not required, it is preferred to add a tertiary amine such as triethylamine or pyridine. The reaction temperature may vary from 0° to 100°, and $R_6OH$ is often taken in excess of theory. The combination of 2 equivalents of $R_6OH$, 1.1 equivalents of triethylamine, and 0.1 equivalents of imidazole in dimethylformamide at 80° for two hours has been broadly applicable. Compounds having $R_6$=alkyl may be converted to silanols ($R_6$=H) and/or the corresponding disiloxanes by hydrolysis, catalyzed by acid or base, preferably catalyzed by acid. In some instances this cleavage may occur during the triazole displacement, so that chloromethyl silyl ethers having $R_6$=alkyl can give rise directly to triazolylmethyl silanols having $R_6$=H.

Extending these methods to (chloromethyl)dichlorosilanes provides dioxygenated silanes:

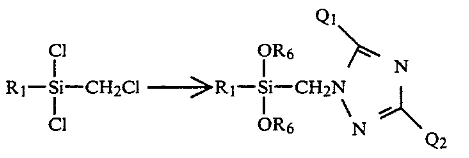

After forming the silicon-oxygen bonds, it is sometimes advantageous to convert the chloromethylsilane to an iodomethylsilane with a suitable source of iodide ion before performing the triazole displacement reaction. Conversion of these dioxygenated compounds to the glycol bridge substituted silanes is accomplished by heating with equimolar amounts of the suitably substituted glycol in the presence of acid catalysts such as p-toluenesulfonic acid while $R_6OH$ is distilled away:

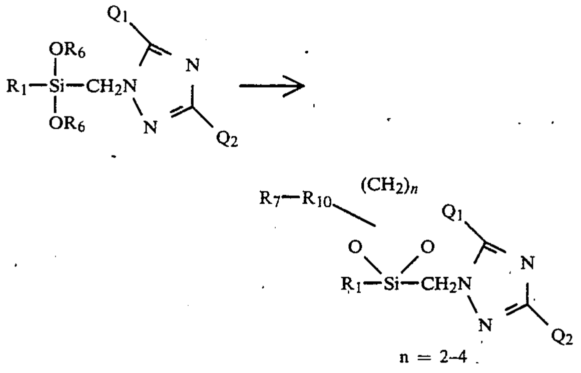

or

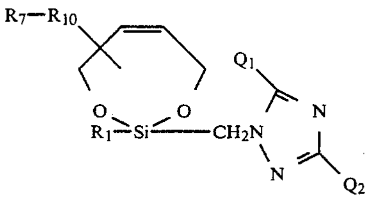

An alternative synthesis for alkoxy(chloromethyl)silanes involves selective replacement of one alkoxy group of a dialkoxysilane with an organometallic reagent as shown in the following reaction sequence:

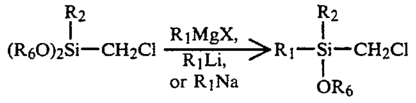

Conditions for this displacement are described below, with the added stipulation that the organometallic is preferably added to the dialkoxysilane.

The required chloromethylsilane starting materials are made from commercially available chloro(chloromethyl)dimethylsilane, chloromethyl(dichloro)methylsilane, or chloromethyltrichlorosilane:

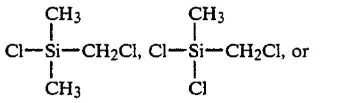

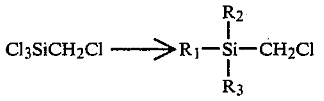

The Si—Cl bonds in these compounds react with organolithium, organosodium, or Grignard reagents to introduce alkyl and/or aryl groups according to literature procedures, leaving the C—Cl bond intact. For the silanes containing two or three Si—Cl bonds, stepwise replacements are possible, giving considerable flexibility to the values of $R_1$–$R_3$. Bromosilanes, iodosilanes, or alkoxysilanes may be substituted for chlorosilanes in these reactions. Preferred solvents for these reactions include ethers such as tetrahydrofuran, 1,2-dimethoxyethane, and diethyl ether, or hydrocarbons such as hexane and toluene. The temperature will vary between −80° and 40° depending on the nature of the organometallic reagent, how it was generated, and the solvent. For example, when aryllithium reagents are generated in tetrahydrofuran from aryl bromides using butyllithium, the mixture should be held below about −40° to avoid side reactions involving the bromobutane produced. If the organometallic solution is stable at higher temperatures, however, reactions may be run at −20° to 25° without competing reaction of the $CH_2Cl$ group.

Reactions of $ClSi(CH_3)_2CH_2Cl$ with Grignard reagents are described by C. Eaborn and J. C. Jeffrey, *J. Chem. Soc.*, 1954, 4266; and a recent review on synthesis of aryltrimethylsilanes from $ClSi(CH_3)_3$, which contains experimental procedures useful for $ClSi(CH_3)_2CH_2Cl$ reactions, is that of D. Habich and F. Effenberger, *Synthesis*, 1979, 841. Selective introduction of one new alkyl group into $Cl_2Si(CH_3)CH_2Cl$ is described by V. P. Kuznetsova and R. M. Sokolovaskaya, *Zh. Obshch. Khim.*, 1969, 1977; *Chem. Abstr.*, 72, 31897 p; and one aryl group may be introduced selectively as well:

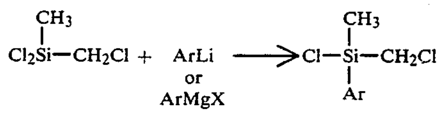

In some cases the organometallic reagent is preferably added to the dichlorosilane at low temperature with good mixing for best yields. Grignard reagents tend to be more selective than organolithiums.

Reaction of $Cl_3SiCH_2Cl$ with Grignard reagents are described by A. A. Zhdanov, V. I. Pakhomov, and T. Bazhanova, *Zh. Obshch. Khim.*, 1973, 1280; *Chem. Abstr.*, 79, 66452 m. One or two aryl groups may be introduced selectively as shown below:

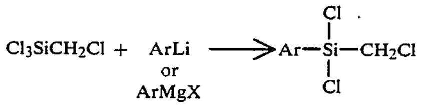

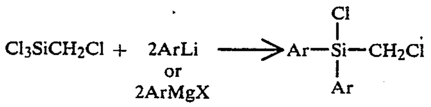

Grignard reagents are again more selective than organolithiums, and in many cases a third equivalent of Grignard reacts slowly or not at all, providing a very clean synthesis of diarylchloro(chloromethyl)silanes.

A useful modification of literature procedures, applicable when $R_1$ is an aryl group, has been developed in the present work. Instead of preforming an organolithium reagent and then combining it with a chlorosilane, it has been found that an aryl bromide and a chlorosilane such as $ClSi(CH_3)_2CH_2Cl$ may be combined in an inert solvent such as tetrahydrofuran and treated at −80° to −40° with butyllithium. Brominelithium exchange proceeds selectively, and the resulting aryllithium reacts with the Si-Cl bond as it is formed:

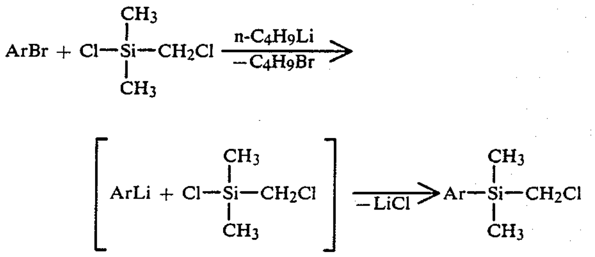

This reaction works equally well for aryl-substituted chlorosilanes such as $ClSi(CH_3)(C_6H_5)CH_2Cl$, and it can be used to introduce two aryl groups into $Cl_2Si(CH_3)CH_2Cl$. In a further extension, an aryl and an n-butyl group may be introduced in one step:

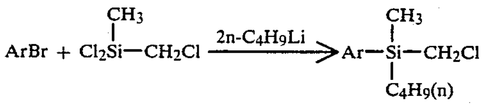

Substitution of other alkyllithiums RLi for n-butyllithium provides a general route to $Ar(CH_3)Si(R)CH_2Cl$.

The compounds of this invention wherein $R_{11}$ is $C_1$–$C_4$ alkyl are prepared by applying the reaction described above to $R_1R_2R_3SiCH(R_{11})Cl$. The required 1-chloroalkylsilane intermediates can be prepared by either of two literature methods. Free-radical chlorination of alkylchlorosilanes with sulfuryl chloride is described by Y. Nagai, N. Machida, H. Kono and T. Migita, *J. Org. Chem.*, 32, 1194 (1967). Mixtures of 1-, 2-, 3- etc. chloroalkylchlorosilanes are obtained. The 1-chloroalkyl isomer can be separated, for example by distillation, and converted to the appropriately substituted 1-chloroalkylsilane by Grignard addition as described above. This is illustrated for an alkyltrichlorosilane as follows:

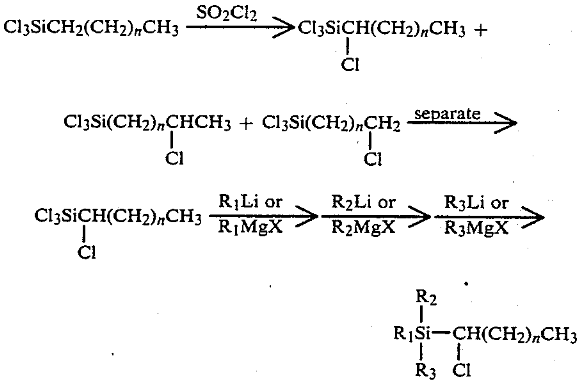

n = 0, 1, 2 or 3

An alternative synthesis was developed using metallation chemistry. Reaction of chloromethyltrimethylsilane with secondary butyllithium and tetramethylethylenediamine (TMEDA) forming 1-lithio-1-chloromethyltrimethylsilane, followed by treatment with methyl iodide to yield 1-chloroethyltrimethylsilane, is described by C. Burford, F. Cooke, E. Ehlinger and P. Magnus, *J. Am. Chem. Soc.*, 99, 4536 (1977) and F. Cooke and P. Magnus, *J. Chem. Soc. Chem. Comm.*, 513 (1977):

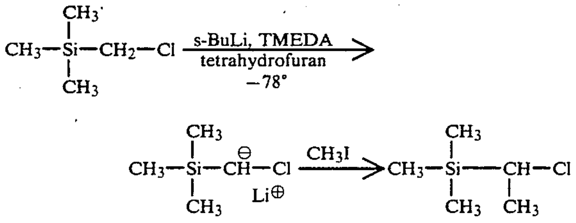

A useful modification of the literature method has been developed in the present work, extending it to more complex silanes and other alkylating agents. Deprotonation of chloromethylsilanes with sec-butyllithium followed by treatment with alkyl halides has been found to give 1-chloroalkylsilanes:

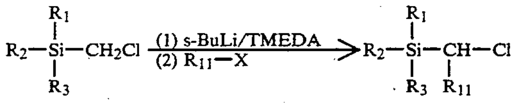

Displacement of the 1-chloroalkylsilanes with triazole is accomplished as described above for chloromethylsilanes; however, longer reaction times are required. For example, 1H-1,2,4-triazole sodium salt in dimethylformamide gives good conversion in approximately 64 hours at 50° when $R_{11}$ is $CH_3$.

In the following examples, temperatures are reported in degrees Celsius. Abbreviations for nuclear magnetic resonance (nmr) spectra are s=singlet, d=doublet, t=triplet, q=quartet, m=multiplet; peak positions are reported as parts per million downfield from internal tetramethylsilane. Infrared (ir) peak positions are given in reciprocal centimeters ($cm^{-1}$). Hexanes refers to the mixture of isomers boiling 68°–69°, and ether refers to diethyl ether.

EXAMPLE 1

Preparation of (1,1′-Biphenyl-4-yl)(chloromethyl)dimethylsilane

A solution of 9.9 g (0.042 mol) of 4-bromobiphenyl in 50 ml of dry tetrahydrofuran was cooled to −78° under nitrogen and stirred while 26.5 ml (0.042 mol) of 1.6 molar n-butyllithium in hexane was added dropwise over 15 minutes. A thick slurry formed, and 35 ml of tetrahydrofuran was added to facilitate stirring. With continued cooling, 5.9 ml (6.7 g, 0.046 mol) of chlorochloromethyldimethylsilane was added over 10 minutes, giving a clear solution that was allowed to warm to room temperature. Addition of 300 ml of ether, filtration to remove precipitated lithium chloride, and evaporation of the filtrate left 13.2 g of semisolid. Redissolution in ether, filtration, and evaporation of the filtrate left 11.0 g (100% crude) of the title compound as a colorless solid, m.p. 30°–40°, suitable for further reaction. Trace impurities could be removed by sublimation at 30°/0.1 mm, leaving the title compound unsublimed in 83% recovery; m.p. 37°–40°; ir (Nujol ®) 1585, 1240, 1110, 830, 810, 750, 690 $cm^{-1}$, nmr ($CDCl_3$) 0.4 (6H, s), 2.9 (2H, s), 7.3–7.7 (9H, m).

EXAMPLE 2

Preparation of (4-Bromophenyl)(chloromethyl)dimethylsilane

4-Bromophenylmagnesium bromide was prepared from 11.8 g (0.050 mol) of 1,4-dibromobenzene and 1.2 g (0.050 g-atom) of magnesium turnings in 75 ml of ether according to G. P. Schiemenz, *Org. Syn.*, Coll. Vol. 5, 496 (1973). The resulting mixture was chilled in ice under a nitrogen atmosphere while a solution of 6.6 ml (7.2 g, 0.050 mol) of chlorochloromethyldimethylsilane in 10 ml of ether was added dropwise. The reaction mixture was then stirred overnight at room temperature, quenched carefully with saturated aqueous ammonium chloride, and filtered. The ether phase of the filtrate was washed with brine, dried over magnesium sulfate, and evaporated to leave 9.8 g of an oil. Distillation gave 3.8 g (29%) of the title compound as a colorless liquid: bp 97° (1 mm); ir (neat) 2950, 1575, 1475, 1370, 1250, 1065, 1010, 840, 805, 720 $cm^{-1}$; nmr ($CDCl_3$) 0.4 (6H, s), 2.9 (2H, s), 7.3–7.7 (4H, m).

EXAMPLE 3

Preparation of (Chloromethyl)(4-chlorophenyl)dimethylsilane

A solution of 9.6 g (0.050 mol) of 4-bromochlorobenzene and 6.6 ml (7.2 g, 0.050 mol) of chlorochloromethyldimethylsilane in 75 ml of tetrahydrofuran was stirred at −78° under nitrogen while 31 ml (0.050 mol) of 1.6 molar n-butyllithium in hexane was added dropwise. The resulting clear solution was allowed to warm to room temperature, diluted with ether until no more lithium chloride precipitated, and filtered. Evaporation of the filtrate left 10.6 g of a light yellow liquid, which was distilled to give 6.0 g (55%) of the title compound as a colorless liquid: bp 54°–58° C. (0.05 mm); ir (neat) 2910, 1560, 1470, 1370, 1250, 1080, 1010, 840, 805, 790, 740 $cm^{-1}$; nmr ($CDCl_3$) 0.4 (6H, s), 2.9 (2H, s), 7.1–7.6 (4H, q).

The in situ aryllithium generation described in this example is also useful for preparing the product of Example 1. If the reaction is run at 0.5–0.7 molar in 4-bromobiphenyl and the temperature is held at −65° to −55° C. during butyllithium addition, little or no solid precipitates.

EXAMPLE 4

Preparation of Chloromethyl(2,4-dichlorophenyl)dimethylsilane

A solution of 17.0 g (0.075 mol) of 2,4-dichlorobromobenzene and 10.8 ml (11.8 g, 0.082 mol) of chloro(chloromethyl)dimethylsilane in 100 ml of dry tetrahydrofuran was chilled to −70° under nitrogen and stirred while 49 ml (0.079 mol) of 1.6 molar n-butyllithium in hexane was added dropwise at a rate that held the mixture below −70°. The resulting cloudy reaction mixture was allowed to warm to room temperature, poured into 400 ml of hexanes, filtered, and evaporated to leave 20.5 of yellow liquid. Distillation gave 12.6 g (66%) of the title compound as a colorless liquid: bp 83° (0.02 mm); $n_D^{24}$ 1.5522; ir (neat) 1565, 1455, 1360, 1255, 1120, 1100, 1040, 825 $cm^{-1}$; nmr ($CDCl_3$) 0.5 (6H, s), 3.1 (2H, s), 7.0–7.5 (3H, m).

EXAMPLE 5

Preparation of Chloromethyl(2,6-dimethoxyphenyl)dimethylsilane

A solution of 25.0 g (0.181 mol) of 1,3-dimethoxybenzene in 250 ml of tetrahydrofuran was stirred at room temperature under nitrogen while 125 ml (0.200 mol) of 1.6 molar n-butyllithium in hexane was added dropwise over 30 minutes. The resulting mixture was refluxed 1.5 hour, giving an orange-brown solution that was cooled to 5° and stirred while 27 ml (29.4 g, 0.205 mol) of chloro(chloromethyl)dimethylsilane was added dropwise over 15 minutes. The resulting white suspension was allowed to warm to room temperature, stirred there 1 hour, diluted with ethyl acetate, poured into water, and extracted with ether. The organic layers were washed with brine, dried over magnesium sulfate, and distilled to give 37.0 g (84%) of the title compound as a colorless liquid: bp 98°-110° (0.1 mm); nmr ($CDCl_3$) 0.4 (6H, s), 3.1 (2H, s), 3.7 (6H, s), 6.3 (2H, d), 7.1 (1H, m).

By varying the organolithium or Grignard reagent, the procedures of Examples 1-5 can be used to prepare the compounds of Table I. Closely related procedures are also known in the literature, for example the use of arylmagnesium chlorides by C. Eaborn and J. C. Jeffrey, *J. Chem. Soc.*, 1954, 4266. For compounds where $R_1$ is a phenyl ring bearing a 2-halo substituent, an alternative to the in situ procedure of Example 4 is the special arylmagnesium iodide method of C. Eaborn, K. L. Jaura, and D. R. M. Walton, *J. Chem. Soc.*, 1964, 1198.

TABLE I

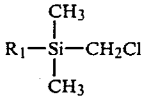

| $R_1$ | |
|---|---|
| $C_2H_5$ | bp 127-128° |
| n-$C_4H_9$ | bp 172° |
| n-$C_{12}H_{25}$ | $n_D^{23}$ 1.4510 |
| n-$C_{18}H_{37}$ | $n_D^{22}$ 1.4556 |
| cyclopropyl | |
| cyclopentyl | |
| cyclohexyl | bp 120-130° (10 mm) |
| 1-naphthyl | bp 112° (0.08 mm) |
| 2-naphthyl | |
| phenyl | bp 85-86° (3 mm) |
| 4-fluorophenyl | bp 59-60° (0.1 mm) |
| 4-methoxyphenyl | bp 80° (0.05 mm) |
| 4-phenoxyphenyl | bp 122° (0.03 mm) |
| 4-(4-chlorophenoxy)phenyl | $n_D^{22}$ 1.5773 |
| 4-(4-fluorophenoxy)phenyl | |
| 4-(4-trifluoromethylphenoxy)phenyl | |
| 4-(4-methylphenoxy)phenyl | |
| 4-thiomethylphenyl | bp 92-93° (0.05 mm) |
| 4-trifluoromethylphenyl | $n_D^{23}$ 1.4686 |
| 4-methylphenyl | bp 96° (7 mm) |
| 4-i-propylphenyl | |
| 4-t-butylphenyl | $n_D^{23}$ 1.5056 |
| 4-methylsulfonylphenyl | m.p. 64-68° |
| 4-cyclohexylphenyl | $n_D^{21}$ 1.5424 |
| 4-trifluoromethoxyphenyl | bp 55-57° (0.15 mm) |
| 4-(4-chlorophenyl)phenyl | |
| 4-(4-bromophenyl)phenyl | |
| 4-(4-methylphenyl)phenyl | |
| 4-(4-trifluoromethylphenyl)phenyl | |
| 4-(4-fluorophenyl)phenyl | |
| 3-phenylphenyl | $n_D^{20}$ 1.5862 |
| 3-trifluoromethylphenyl | bp 59-62° (0.3 mm) |
| 3-chlorophenyl | bp 73° (0.15 mm) |
| 2-trifluoromethylphenyl | $n_D^{23}$ 1.4826 |
| 2-phenylphenyl | $n_D^{20}$ 1.5772 |
| 2-chlorophenyl | bp 78-80° (0.3 mm) |
| 2-methoxyphenyl | $n_D^{21}$ 1.5164 |
| 2,3-dimethylphenyl | |
| 2,3-dimethoxyphenyl | $n_D^{22}$ 1.5254 |
| 2,4-difluorophenyl | |
| 2-fluoro-4-chlorophenyl | |
| 2-chloro-4-phenylphenyl | |
| 2-fluoro-4-phenylphenyl | |
| 2-methyl-5-chlorophenyl | |
| 2,6-dimethylphenyl | |
| 3,4-dichlorophenyl | bp 98° (0.6 mm) |

TABLE I-continued

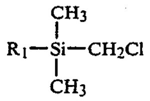

| $R_1$ | |
|---|---|
| 3-methyl-4-fluorophenyl | |
| 3,5-dichlorophenyl | bp 94-95° (0.25 mm) |

EXAMPLE 6

Preparation of (1,1'-Biphenyl-4-yl)butyl(chloromethyl)methylsilane

The title compound can be prepared by the procedure of Example 1 by substituting butylchloro(-chloromethyl)methylsilane for chlorochloromethyldimethylsilane.

Related compounds can be prepared by the procedures of Examples 1-5, using the appropriate organolithium or Grignard reagent and $Cl(R_2)Si(CH_3)CH_2Cl$. The required chloromethylsilane starting materials are made from $R_2MgCl$ or $R_2Li$ and $Cl_2Si(CH_3)CH_2Cl$ according to Examples 14 and 15, and literature procedures such as V. P. Kuznetsova and R. M. Sokolovaskaya, *Zh. Obshch. Khim.*, 1969, 1997.

Alternatively, both the biphenyl and butyl groups can be introduced simultaneously as follows: A solution of 23.3 g (0.10 mol) of 4-bromobiphenyl and 12.7 ml (16.4 g, 0.10 mol) of chloromethyl(dichloro)methylsilane in 150 ml of dry tetrahydrofuran was chilled under nitrogen to −70° and stirred while 125 ml (0.20 mol) of 1.6 molar n-butyllithium in hexane was added at a rate that held the mixture below −60° C. The resulting thin slurry was allowed to warm to room temperature, treated cautiously with 10 ml of ethyl acetate, and poured into 300 ml of water. The organic layer was separated, the aqueous phase was washed with another 100 ml of hexanes, and the combined organic phases were washed three times with water, once with brine, dried over magnesium sulfate, and evaporated to leave 33.9 g of a viscous yellow oil. Distillation gave 9.5 g (31%) of the title compound: bp 135°-158° (0.1 mm); $n_D^{22}$ 1.5743; ir (neat) 3060, 3015, 2960, 2920, 2870, 1600, 1485, 1390, 1380, 1250, 1120, 1075, 1005, 875, 810, 800, 760, 700 $cm^{-1}$; nmr ($CDCl_3$): 0.4 (3H, s), 0.6-1.8 (9H, m), 2.9 (2H, s) and 7.0-7.7 (9H, m).

EXAMPLE 7

Preparation of Butyl(chloromethyl)(4-chlorophenyl)methylsilane

A solution of 14.4 g (0.075 mol) of 4-bromochlorobenzene and 9.5 ml (12.3 g, 0.075 mol) of chloromethyl(-dichloro)methylsilane in 150 ml of tetrahydrofuran was cooled to −60° under nitrogen and stirred while 94 ml (0.15 mol) of 1.6 molar n-butyllithium in hexane was added dropwise at a rate that held the mixture between −65° and −55°. The resulting slurry was allowed to warm to room temperature, giving a solution that was diluted with hexanes until no more lithium chloride precipitated. Filtration, evaporation of the filtrate, dissolution of the residue in hexanes, refiltration, and evaporation left 19.8 g of a pale orange liquid. Distillation gave first 1.8 g (12%) of chloromethyl(dibutyl)methylsilane, bp 45° C. (0.05 mm), followed by 6.8 g (35%) of the title compound as a colorless liquid: bp 90° C. (0.05 mm); $n_D^{21}$ 1.5246; ir (neat) 2925, 1580, 1380, 1260, 1090, 1015, 820, 740 $cm^{-1}$; nmr ($CDCl_3$) 0.4 (3H, s), 0.6–1.5 (9H, m), 2.9 (2H, s), 7.0–7.4 (4H, q).

EXAMPLE 8

Preparation of Chloromethyl(2,4-dichlorophenyl)methyl(phenyl)silane

A solution of 13.6 g (0.060 mol) of 2,4-dichlorobromobenzene and 12.3 g (0.060 mol) of chloro(chloromethyl)methyl(phenyl)silane (prepared as in Example 14) in 85 ml of dry tetrahydrofuran was chilled to −60° under nitrogen and stirred while 38 ml (0.060 mol) of 1.6 molar n-butyllithium in hexane was added dropwise at a rate that held the mixture below −55°. The resulting red solution was allowed to warm to room temperature, treated with 5 ml of ethyl acetate to quench any unreacted organolithium reagent, and poured into 170 ml of water. The organic layer was separated, the aqueous phase was washed with 50 ml of hexanes, and the combined organic phases were washed three times with water and once with brine, dried over magnesium sulfate, and evaporated to leave 19.0 g of bright yellow oil. Distillation gave 8.6 g (45%) of the title compound as a colorless liquid: b.p. 125°–130° (0.05 mm); $n_D^{21}$ 1.5978; ir (neat) 3080, 3060, 2960, 2930, 1570, 1540, 1460, 1430, 1365, 1260, 1120, 1100, 1040, 820, 745, 735, 705 $cm^{-1}$; nmr ($CDCl_3$) 0.8 (3H, s), 3.4 (2H, s), 7.2–7.9 (8H, m).

EXAMPLE 9

Preparation of (1,1′-Biphenyl-4-yl)chloromethyl(4-fluorophenyl)methylsilane

A solution of 10.0 g (32.8 mmol) of (1,1′-biphenyl-4-yl)(chloromethyl)methyl(2-propoxy)silane and 3.6 ml (32.8 mmol) of 4-bromofluorobenzene in 30 ml of dry tetrahydrofuran was cooled to −60° under nitrogen and stirred while 20.5 ml (32.8 mmol) of 1.6 molar n-butyllithium in hexane was added at a rate that held the mixture below 50°. After stirring at −70° for another 30 minutes, the solution was allowed to warm to room temperature and was worked up as in Example 8. The resulting crude product was subjected to distillation at 130°–150° (0.2 mm) to remove unreacted starting material, leaving the title compound as an oil: $n_D^{23}$ 1.5128; nmr ($CDCl_3$): 0.7 (3H, s), 3.1 (2H, s), 7.1 (2H, t), 7.2–7.8 (11H, m).

EXAMPLE 10

Preparation of Chloromethylbis(4-chlorophenyl)methylsilane

A solution of 19.1 g (0.10 mol) of 4-chlorobromobenzene in 200 ml of dry tetrahydrofuran was chilled to −60° under nitrogen and stirred while 63 ml (0.10 mol) of 1.6 molar n-butyllithium in hexane was added dropwise at a rate that held the mixture below −55°. Stirring and cooling were continued while 6.3 ml (8.2 g, 0.05 mol) of chloromethyl(dichloro)methylsilane was added dropwise at a rate that held the mixture below −50°. The resulting orange solution was allowed to warm to room temperature, and workup as in Example 8 provided 16.5 g of a pale yellow oil. Kugelrohr distillation at 0.05 mm and an airbath temperature of 130°–150° C. gave 9.5 g (60%) of the title compound as a colorless liquid: $n_D^{24}$ 1.5913; ir (neat) 3080, 3040, 3020, 2960, 2930, 1580, 1490, 1380, 1260, 1085, 1015, 805, 790, 775, 740 $cm^{-1}$; nmr ($CDCl_3$) 0.7 (3H, s), 3.1 (2H, s), 7.2–7.7 (8H, m); analysis for $C_{14}H_{13}Cl_3Si$ (mw 315.70):

Calculated: C, 53.26; H, 4.15; Cl, 33.69. Found: C, 53.4; H, 4.4; Cl, 34.2. 53.5; 4.4; 34.1.

EXAMPLE 11

Preparation of (Chloromethyl)bis(4-fluorophenyl)methylsilane

A solution of 35 g (0.20 mol) of 4-fluorobromobenzene in 300 ml of dry tetrahydrofuran was chilled to −60° under nitrogen and stirred while 126 ml (0.20 mol) of 1.6 molar n-butyllithium in hexane was added dropwise at a rate that held the mixture below −55°. Stirring and cooling were continued while 12.6 ml (16.4 g, 0.10 mol) of chloromethyl(dichloro)methylsilane was added dropwise at a rate that held the mixture below −50°. The resulting solution was allowed to warm to room temperature, and workup as in Example 8 provided 26.4 g of a clear yellow liquid. Distillation gave 20.6 g (73%) of the title compound as a colorless liquid: bp 107°–127° (0.1 mm); $n_D^{22}$ 1.5481; nmr ($CDCl_3$): 0.7 (3H, s), 3.2 (2H, s), 7.1 (4H, t, J=9) and 7.6 (4H, d of d, J=6 and 9). A similar sample of the title compound was crystallized from ether-hexane at −78° to give colorless solid, m.p. 39°–40°.

Repeating this reaction using chloromethyl(diethoxy)methylsilane instead of the dichlorosilane gave the title compound in 58% yield after distillation: bp 115°–138° (0.2 mm); $n_D^{21}$ 1.5464; nmr as above.

EXAMPLE 12

Preparation of Chloromethyl(2-chlorophenyl)(4-chlorophenyl)methylsilane

A solution of 6.3 ml (8.2 g, 0.05 mol) of chloromethyl(dichloro)methylsilane and 8.1 g (0.05 mol) of 2-bromochlorobenzene in 75 ml of dry tetrahydrofuran was chilled to −60° under $N_2$ and stirred while 31 ml (0.05 mol) of 1.6 molar n-butyllithiumhexane solution was added at a rate that held the mixture below −55°. With continued cooling and stirring, 8.1 g (0.05 mol) of 4-bromochlorobenzene was added as a solid, followed by another 31 ml portion of the 1.6 molar n-butyllithium solution at a rate that held the mixture below −55° C. The resulting thin slurry was allowed to warm to room temperature, treated cautiously with 10 ml of ethyl acetate, and worked up as in Example 8 to give 15.0 g of a clear yellow oil. Distillation provided 5.9 g (37%) of the title compound: bp 150°–165° (0.7 mm); $n_D^{20}$ 1.5916; ir (neat) 3060, 3020, 2960, 2920, 2870, 1580, 1560, 1490, 1420, 1380, 1255, 1125, 1115, 1085, 1035, 1015, 805, 750 $cm^{-1}$; nmr ($CDCl_3$) 0.8 (3H, s), 3.3 (2H, s), 7.2–7.7 (8H, m).

The compounds of Table II are made by stepwise replacement of the Si—Cl bonds of $Cl_2Si(CH_3)CH_2Cl$, according to the procedures of Examples 6–12.

TABLE II

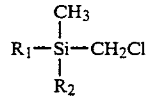

| $R_1$ | $R_2$ | |
|---|---|---|
| $C_2H_5$ | $C_2H_5$ | |
| i-$C_3H_7$ | cyclohexyl | |
| n-$C_4H_9$ | n-$C_4H_9$ | bp 45° (0.05 mm) |

TABLE II-continued

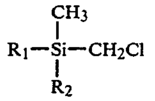

| $R_1$ | $R_2$ | |
|---|---|---|
| n-$C_{10}H_{21}$ | cyclopropyl | |
| n-$C_{18}H_{37}$ | 3-methylbutyl | |
| cyclopropyl | n-$C_6H_{13}$ | |
| cyclohexyl | cyclohexyl | |
| 1-naphthyl | t-$C_4H_9$ | |
| 2-naphthyl | n-$C_5H_{11}$ | |
| phenyl | n-$C_3H_7$ | |
| phenyl | n-$C_4H_9$ | bp 82–90° (0.1 mm) |
| phenyl | 1,1-dimethylpropyl | |
| 4-phenylphenyl | $C_2H_5$ | |
| 4-bromophenyl | i-$C_3H_7$ | |
| 4-fluorophenyl | n-$C_4H_9$ | bp 90–92° (0.1 mm) |
| 4-phenoxyphenyl | t-$C_4H_9$ | |
| 4-t-butylphenyl | cyclopentyl | |
| 3-trifluoromethylphenyl | s-$C_4H_9$ | |
| 3-chlorophenyl | n-$C_5H_{11}$ | |
| 2-thiomethylphenyl | cyclobutyl | |
| 2-phenylphenyl | i-$C_4H_9$ | |
| 2,4-dichlorophenyl | n-$C_4H_9$ | bp 109–112° (0.1 mm) |
| 2,4-dichlorophenyl | cyclopropyl | |
| 2,3-dimethylphenyl | n-$C_3H_7$ | |
| 2-methyl-5-fluorophenyl | cyclopentyl | |
| 2,5-dimethoxyphenyl | 4-methylpentyl | |
| 2,6-dimethylphenyl | 1-methylbutyl | |
| 3,5-dichlorophenyl | n-$C_4H_9$ | |
| 3,5-dichlorophenyl | cyclohexyl | |
| 3-methyl-4-chlorophenyl | cyclopropyl | |
| phenyl | phenyl | bp 104–110° (0.2 mm) |
| 4-fluorophenyl | phenyl | $n_D^{22}$ 1.5624 |
| 4-chlorophenyl | phenyl | bp 140–148° (0.1 mm) |
| 4-bromophenyl | phenyl | bp 145–155° (0.1 mm) |
| 4-phenylphenyl | phenyl | bp 173–178° (0.1 mm) |
| 4-t-butylphenyl | phenyl | |
| 4-thiomethylphenyl | phenyl | |
| 4-phenoxyphenyl | phenyl | |
| 4-trifluoromethoxyphenyl | phenyl | |
| 4-methylsulfonylphenyl | phenyl | |
| 4-cyclohexylphenyl | phenyl | |
| 4-(4-fluorophenyl)phenyl | phenyl | |
| 3-trifluoromethylphenyl | phenyl | |
| 2-chlorophenyl | phenyl | bp 132–135° (0.1 mm) |
| 2-methoxyphenyl | phenyl | |
| 2-chloro-4-phenylphenyl | phenyl | |
| 2-fluoro-4-phenylphenyl | phenyl | |
| 3,5-dichlorophenyl | phenyl | |
| 2,5-dimethoxyphenyl | phenyl | |
| 2,6-dimethoxyphenyl | phenyl | |
| 4-bromophenyl | 4-bromophenyl | bp 160–170° (0.1 mm) |
| 4-phenylphenyl | 4-phenylphenyl | m.p. 115–117° |
| 4-methylphenyl | 4-methylphenyl | bp 118–122° (0.1 mm) |
| 4-methoxyphenyl | 4-methoxyphenyl | bp 166–171° (0.1 mm) |
| 3-trifluoromethylphenyl | 3-trifluoromethyl-phenyl | |
| 2-methoxyphenyl | 2-methoxyphenyl | |
| 2-chlorophenyl | 2-chlorophenyl | bp 135–140° (0.1 mm) |
| 2,4-dichlorophenyl | 2,4-dichlorophenyl | $n_D^{21}$ 1.5956 |
| 3,5-dichlorophenyl | 3,5-dichlorophenyl | |
| 2-chlorophenyl | 4-fluorophenyl | |
| 4-phenylphenyl | 4-chlorophenyl | |
| 4-phenylphenyl | 2,4-dichlorophenyl | |
| 4-fluorophenyl | 2,4-dichlorophenyl | |
| 4-chlorophenyl | 2,4-dichlorophenyl | |
| 1-naphthyl | 2,6-dimethoxyphenyl | |

TABLE II-continued

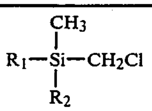

| $R_1$ | $R_2$ |
|---|---|
| 4-phenoxyphenyl | 3,4-dichlorophenyl |

EXAMPLE 13

Preparation of (1-1′-Biphenyl-1-yl)(chloromethyl)diethylsilane

The title compound can be prepared by the procedure of Example 1, using chlorochloromethyldiethylsilane instead of chlorochloromethyldimethylsilane.

Similar compounds can be prepared by applying the procedures of Examples 1–5 to the appropriate organolithium or Grignard reagent and $Cl(R_2)Si(R_3)CH_2Cl$. The required chlorochloromethyldialkylsilanes are made from $Cl_3SiCH_2Cl$, using two equivalents of $R_2MgCl$ or $R_2Li$ when $R_2=R_3$ (see, for example, A. A. Zhdanov, V. I. Pakhomov, and T. Bazhanova, *Zh. Obshch. Khim.*, 1973, 1280), or using one equivalent of $R_2MgCl$ or $R_2Li$ followed by one equivalent of $R_3MgCl$ or $R_3Li$ when $R_2$ is not equal to $R_3$.

EXAMPLE 14

Preparation of (Chloromethyl)triphenylsilane

A solution of 12.6 ml (18.4 g, 0.10 mol) of (chloromethyl)trichlorosilane in 150 ml of dry ether was stirred under nitrogen and chilled in ice while 162 ml (0.30 mol) of 1.85 molar phenyllithium in cyclohexane-ether 70:30 was added dropwise at a rate that held the mixture below 15° C. The resulting slurry was stirred overnight at room temperature, treated carefully with 10 ml of ethyl acetate to quench any remaining phenyllithium, washed with water and brine, dried over magnesium sulfate, and evaporated to leave 33 g of sticky solid. Recrystallization from 30 ml of cyclohexane provided 15.8 g (51%) of the title compound as an off white solid: m.p. 112°–115° C.; ir (Nujol®) 1420, 1110, 735, 730, 705, 695 $cm^{-1}$; nmr ($CDCl_3$) 3.5 (2H, s), 7.0–7.8 (15H, m).

EXAMPLE 15

Preparation of Chloromethyl[tris(4-chlorophenyl)]silane

A solution of 24.5 g (0.128 mol) of 4-bromochlorobenzene in dry tetrahydrofuran was cooled to −60° under nitrogen and stirred while 80 ml (0.128 mol) of 1.6 molar n-butyllithium in hexane was added at a rate that held the mixture below −50°. The resulting solution was stirred another 10 minutes at −60° to −70°, and then a solution of 5.2 ml (0.041 mol) chloromethyltrichlorosilane in tetrahydrofuran was added dropwise over 30 minutes. The resulting solution was stirred at −70° for 1 hour, allowed to warm to room temperature, quenched with saturated aqueous ammonium chloride, and extracted with ether. Washing the ether extracts with brine, drying over magnesium sulfate, and evaporation left a viscous oil, which was chromatographed over silica gel (hexanes elution) to give 9.1 g (53%) of the title compound as a colorless oil that solidified on standing: m.p. 89°–93°; nmr ($CDCl_3$) 3.4 (2H, s), 7.5 (12H, broad s).

The compounds of Table III are made by stepwise replacement of the Si—Cl bonds of $Cl_3SiCH_2Cl$, according to the procedures of Examples 13–15.

TABLE III

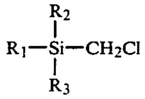

| $R_1$ | $R_2$ | $R_3$ |
|---|---|---|
| $C_2H_5$ | $C_2H_5$ | $C_2H_5$ |
| i-$C_3H_7$ | i-$C_3H_7$ | i-$C_3H_7$ |
| n-$C_4H_9$ | n-$C_4H_9$ | n-$C_4H_9$ |
| n-$C_8H_{17}$ | $C_2H_5$ | cyclopentyl |
| n-$C_{14}H_{29}$ | cyclopropyl | 1-methylbutyl |
| n-$C_{18}H_{37}$ | n-$C_6H_{13}$ | n-$C_6H_{13}$ |
| cyclopropyl | $C_2H_5$ | s-$C_4H_9$ |
| cyclohexyl | n-$C_3H_7$ | n-$C_3H_7$ |
| 1-naphthyl | n-$C_4H_9$ | n-$C_4H_9$ |
| 2-naphthyl | n-$C_4H_9$ | cyclobutyl |
| phenyl | cyclopropyl | n-$C_6H_{13}$ |
| 4-phenylphenyl | n-$C_4H_9$ | n-$C_4H_9$ |
| 4-phenylphenyl | n-$C_6H_{13}$ | n-$C_6H_{13}$ |
| 4-phenylphenyl | cyclohexyl | cyclohexyl |
| 4-chlorophenyl | n-$C_4H_9$ | n-$C_4H_9$ |
| 4-fluorophenyl | n-$C_3H_7$ | n-$C_3H_7$ |
| 4-phenoxyphenyl | n-$C_4H_9$ | cyclohexyl |
| 4-(4-chlorophenoxy)phenyl | n-$C_4H_9$ | n-$C_4H_9$ |
| 4-t-butylphenyl | s-$C_4H_9$ | i-$C_4H_9$ |
| 3-methoxyphenyl | $C_2H_5$ | t-$C_4H_9$ |
| 3-trifluoromethylphenyl | s-$C_4H_9$ | s-$C_4H_9$ |
| 2-thiomethylphenyl | i-$C_3H_7$ | 3-methylbutyl |
| 2-phenylphenyl | cyclohexyl | cyclohexyl |
| 2,4-dichlorophenyl | n-$C_4H_9$ | n-$C_4H_9$ |
| 2,6-dimethylphenyl | t-$C_4H_9$ | t-$C_4H_9$ |
| 3,5-dichlorophenyl | cyclopentyl | cyclopentyl |
| 3-methyl-4-chlorophenyl | s-$C_4H_9$ | s-$C_4H_9$ |
| $C_2H_5$ | phenyl | phenyl |
| cyclohexyl | phenyl | phenyl |
| n-$C_{18}H_{37}$ | phenyl | phenyl |
| n-$C_4H_9$ | 4-chlorophenyl | 4-chlorophenyl |
| n-$C_{12}H_{25}$ | 4-chlorophenyl | 4-chlorophenyl |
| 1-naphthyl | 4-fluorophenyl | 4-fluorophenyl |
| cyclopropyl | phenyl | 4-t-butylphenyl |
| n-$C_4H_9$ | phenyl | 4-phenylphenyl |
| t-$C_4H_9$ | phenyl | 2,4-dichlorophenyl |
| n-$C_3H_7$ | phenyl | 3-trifluoromethyl-phenyl |
| i-$C_4H_9$ | phenyl | 3,5-dichlorophenyl |
| cyclopentyl | phenyl | 2,6-dimethoxyphenyl |
| n-$C_{14}H_{29}$ | 4-chlorophenyl | 2-fluorophenyl |
| n-$C_4H_9$ | 4-fluorophenyl | 4-phenylphenyl |
| 4-fluorophenyl | 4-fluorophenyl | 4-fluorophenyl m.p. 57–60° |
| 4-phenylphenyl | 4-phenylphenyl | 4-phenylphenyl |
| 2,4-dichlorophenyl | 2,4-dichloro-phenyl | 2,4-dichlorophenyl |
| phenyl | 4-fluorophenyl | 4-fluorophenyl |
| phenyl | 4-chlorophenyl | 4-chlorophenyl |
| phenyl | 4-phenylphenyl | 4-phenylphenyl |
| phenyl | 2,4-dichloro-phenyl | 2,4-dichlorophenyl |
| 2-naphthyl | 4-methylthio-phenyl | 4-methylthiophenyl |
| 4-chlorophenyl | 2-methoxy-phenyl | 2-methoxyphenyl |
| 4-chlorophenyl | 3-chlorophenyl | 3-chlorophenyl |
| phenyl | 2-chlorophenyl | 4-fluorophenyl |
| phenyl | 4-chlorophenyl | 4-phenylphenyl |
| 1-naphthyl | 4-bromophenyl | 3-methylphenyl |
| 4-phenoxyphenyl | 3,5-dimethyl-phenyl | 3,4-dichlorophenyl |

EXAMPLE 16

Preparation of Chloro(chloromethyl)methyl(phenyl)silane

A solution of 12.7 ml (16.4 g, 0.10 mol) of chloromethyl(dichloro)methylsilane in 200 ml of ether was chilled to −70° under nitrogen and stirred vigorously while a mixture of 55 ml (0.10 mol) of 1.8 molar phenyllithium in 30:70 ether-cyclohexane and 55 ml of ether was added dropwise at a rate that kept the mixture below −70°. The resulting slurry was stirred and warmed to room temperature, then allowed to stand overnight. Filtration and evaporation of the filtrate left 20.4 g of a golden oil, which was distilled to give 14.6 g (71%) of the title compound as a colorless liquid: bp 71°–74° (0.6 mm); $n_D^{23}$ 1.5337; ir (neat) 3080, 3060, 2980, 2930, 1590, 1430, 1260, 1120, 820, 790, 740, 700 $cm^{-1}$; nmr ($CDCl_3$) 0.8 (3H, s), 3.1 (2H, s), 7.3–7.6 (3H, m), 7.6–7.8 (2H, m).

EXAMPLE 17

Preparation of Chloro(chloromethyl)[bis(4-fluorophenyl)]silane

A suspension of 7.0 g (0.288 mol) of magnesium turnings in 50 ml of ether was stirred under nitrogen while a solution of 50.2 g (0.287 mol) of 4-bromofluorobenzene in 200 ml of ether was added dropwise at a rate that maintained gentle reflux. After another 2 hours at reflux, the mixture was chilled in ice and a solution of 12.0 ml (0.096 mol) of chloromethyltrichlorosilane in 30 ml of ether was added dropwise. The resulting mixture was refluxed for 4 hours, chilled in ice, treated with a solution of 7.5 ml of isopropanol in 20 ml of ether, stirred 5 minutes, and filtered. The filtrate was evaporated to leave a viscous oil that was stirred with hexanes to give a slurry. Filtration under nitrogen and evaporation of the filtrate left a mobile oil that was distilled to give 17.6 g (61%) of the title compound: bp 100°–140° (0.1 mm); nmr ($CDCl_3$) 3.3 (2H, s), 7.1 (4H, t), 7.7 (4H, d of d).

EXAMPLE 18

Preparation of (1,1′-Biphenyl-4-yl)chloro(chloromethyl)methylsilane

The title compound can be prepared by reaction of equimolar quantities of 4-bromobiphenyl, chloromethyldichloro(methyl)silane, and n-butyllithium according to the procedure of Example 3.

The compounds of Table IV can be prepared using the procedures of Examples 16–18.

TABLE IV

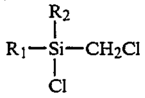

| $R_1$ | $R_2$ |
|---|---|
| $C_2H_5$ | $CH_3$ |
| t-$C_4H_9$ | $CH_3$ |
| n-$C_4H_9$ | $CH_3$ |
| n-$C_{12}H_{25}$ | $C_2H_5$ |
| n-$C_{18}H_{37}$ | n-$C_6H_{13}$ |
| cyclopropyl | $CH_3$ |
| cyclohexyl | $CH_3$ |
| 1-naphthyl | i-$C_3H_7$ |
| 2-naphthyl | cyclobutyl |
| phenyl | t-$C_4H_9$ |
| 4-phenylphenyl | n-$C_4H_9$ |
| 4-phenylphenyl | n-$C_6H_{13}$ |
| 4-chlorophenyl | n-$C_4H_9$ |
| 4-chlorophenyl | $CH_3$ |
| 4-fluorophenyl | n-$C_6H_{13}$ |
| 4-phenoxyphenyl | cyclohexyl |
| 4-t-butylphenyl | n-$C_3H_7$ |
| 4-trifluoromethoxyphenyl | $CH_3$ |
| 4-(4-fluorophenyl)phenyl | $CH_3$ |

TABLE IV-continued

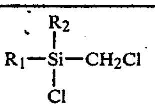

| $R_1$ | $R_2$ |
|---|---|
| 3-trifluoromethylphenyl | t-$C_4H_9$ |
| 2-thiomethylphenyl | cyclopentyl |
| 2,4-dichlorophenyl | $CH_3$ |
| 2,4-dichlorophenyl | n-$C_4H_9$ |
| 2-chloro-4-phenylphenyl | $CH_3$ |
| 2,3-dimethylphenyl | cyclopropyl |
| 2-methyl-5-fluorophenyl | s-$C_4H_9$ |
| 2,6-dimethoxyphenyl | 1,1-dimethylpropyl |
| 3-methyl-4-chlorophenyl | $C_2H_5$ |
| 3,5-dichlorophenyl | n-$C_5H_{11}$ |
| n-$C_{12}H_{25}$ | 2,4-dichlorophenyl |
| n-$C_{18}H_{37}$ | phenyl |
| 1-naphthyl | phenyl |
| phenyl | phenyl |
| 4-fluorophenyl | phenyl |
| 4-chlorophenyl | phenyl |
| 4-phenylphenyl | phenyl |
| 4-t-butylphenyl | phenyl |
| 3-fluorophenyl | phenyl |
| 2-methoxyphenyl | phenyl |
| 2-chlorophenyl | phenyl |
| 2,4-dichlorophenyl | phenyl |
| 3,5-dichlorophenyl | phenyl |
| 4-chlorophenyl | 4-chlorophenyl bp 110–130° (0.1 mm) |
| 4-phenylphenyl | 4-phenylphenyl |
| 2,4-dichlorophenyl | 2,4-dichlorophenyl |
| 3-trifluoromethylphenyl | 3-trifluoromethylphenyl |
| 2-methoxyphenyl | 2-methoxyphenyl |
| 2-chlorophenyl | 4-fluorophenyl |
| 3-trifluoromethylphenyl | 4-t-butylphenyl |
| 2-fluoro-4-chlorophenyl | 4-bromophenyl |
| 2,3-dimethylphenyl | 4-methylthiophenyl |
| 2,6-dimethoxyphenyl | 4-methoxyphenyl |
| 3,4-dichlorophenyl | 4-methylphenyl |

EXAMPLE 19

Preparation of Chloromethyl(methoxy)methyl(phenyl)silane

A solution of 1.6 ml (1.3 g, 0.040 mol) of methanol and 3.0 ml (2.2 g, 0.022 mol) of triethylamine in 100 ml of ether was stirred while a solution of 4.1 g (0.020 mol) of chloro(chloromethyl)methyl(phenyl)silane in 10 ml of ether was added dropwise. The resulting slurry was refluxed for 2 hours, cooled, washed with water, 0.1N aqueous HCl, saturated aqueous $NaHCO_3$, water, and brine, dried over magnesium sulfate, and evaporated to leave 3.2 g of a pale yellow liquid. Distillation provided 1.7 g (42%) of the title compound as a colorless liquid: bp 46°–49° (0.05 mm); $n_D^{22}$ 1.5207; nmr ($CDCl_3$): 0.5 (3H, s), 3.0 (2H, s), 3.5 (3H, s) and 7.3–7.8 (5H, m).

EXAMPLE 20

Preparation of Chloromethyl(1,1-dimethylethoxy)methyl(phenyl)silane

A mixture of 15.4 g (0.075 mol) of chloro(chloromethyl)methyl(phenyl)silane, 14 ml (11.1 g, 0.15 mol) of t-butanol, 11.5 ml (8.3 g, 0.082 g) of triethylamine, and 0.5 g (0.008 mol) of imidazole in 60 ml of dimethylformamide was stirred at 80° For 2 hours. The resulting slurry was cooled, poured into 200 ml of water, and extracted with ether. The ether extracts were washed three times with water, followed by 0.1N aqueous HCl, saturated aqueous $NaHCO_3$, and brine dried over magnesium sulfate, and evaporated to leave 14.0 g of a pale orange oil. Distillation provided 11.9 g (65%) of the title compound: bp 78°–82° (0.2 mm); $n_D^{21}$ 1.5010; ir (neat) 3080, 3060, 2990, 2940, 1600, 1435, 1395, 1370, 1260, 1245, 1195, 1125, 1060, 1030, 815, 790, 740, 725, 705, 650 $cm^{-1}$; nmr ($CDCl_3$): 0.5 (3H, s), 1.3 (9H, s), 2.9 (2H, s) and 7.3–7.8 (5H, m).

EXAMPLE 21

Preparation of (1,1′-Biphenyl-4-yl)chloromethyl(methyl)(2-propoxy)silane

A solution of 73.3 g (0.315 mol) of 4-bromobiphenyl in 300 ml of tetrahydrofuran was added dropwise to a stirred suspension of 7.64 g (0.315 mol) of magnesium in 100 ml of tetrahydrofuran at a rate that maintained gentle reflux. The resulting clear solution was stirred at room temperature for 1 hour and then cooled in ice, and a solution of 40 ml (0.315 mol) of chloromethyl(dichloro)methylsilane in 100 ml of tetrahydrofuran was added rapidly. The resulting solution was stirred at room temperature for 20 hours, treated with 50 ml of isopropanol, and cooled in ice again. A solution of 48 ml (0.344 mol) of triethylamine in tetrahydrofuran was then added at a rate that held the mixture below 25°. Stirring at room temperature for 90 minutes gave a slurry. Filtration, evaporation of the filtrate, trituration with hexanes, and a second filtration removed residual amine hydrochloride. Evaporation of the hexanes solution gave 92 g (96%) of the title compound as a pale yellow oil that solidified on standing: m.p. 35°–38°; nmr ($CDCl_3$) 0.5 (3H, s), 1.2 (6H, d), 3.0 (2H, s), 4.2 (1H, septet), 7.3–7.8 (9H, m).

EXAMPLE 22

Preparation of Chloromethyl[bis(4-fluorophenyl)](2-propoxy)silane

A mixture of 23.2 g (0.955 mol) of magnesium and 50 mg of iodine in 200 ml of ether was stirred while a solution of 167 g (0.954 mol) of 4-bromofluorobenzene in 600 ml of ether was added at a rate that maintained gentle reflux. After another 2 hours at reflux, the solution was cooled in ice and stirred while a solution of 40 ml (0.32 mol) of chloromethyltrichlorosilane in ether was added dropwise over 40 minutes. The resulting mixture was stirred at room temperature for 17 hours, chilled in ice, treated with 24 ml of isopropanol), stirred another 10 minutes, and filtered. The filtrate was concentrated to a gummy solid, hexanes was added, the resulting slurry was filtered, and the hexanes filtrate was evaporated to leave an oil. Analysis by nmr showed the presence of unreacted chlorosilane, so the oil was dissolved in hexanes containing 30 ml of isopropanol, and the solution was chilled in ice and treated with a solution of 42 ml (0.30 mol) of triethylamine in hexanes. The resulting slurry was stirred at room temperature for 3 hours and filtered, and the filtrate was evaporated to leave an oil. Distillation provided 44.8 g (43%) of the title compound as a colorless liquid: bp 120°–140° (0.1 mm); $n_D^{22}$ 1.5211; nmr ($CDCl_3$) 1.2 (6H, d), 3.2 (2H, s), 4.1 (1H, septet), 7.1 (4H, t), 7.7 (4H, d of d).

EXAMPLE 23

Preparation of Chloromethyl(ethoxy)methyl(phenyl)silane

A solution of 18.2 ml (18.2 g, 0.10 mol) of chloromethyl(diethoxy)methylsilane in 200 ml of dry ether was stirred vigorously under $N_2$ and chilled while 56 ml (0.10 mol) of 1.8 molar phenyllithium in 70:30 cyclohexane-ether was added at a rate that held the mixture below −50°. The resulting slurry was allowed to warm to room temperature, treated cautiously with 10 ml of ethyl acetate, washed with water and brine, dried over magnesium sulfate, and evaporated to leave 16.8 g of a golden yellow liquid. Distillation provided 9.5 g (44%) of the title compound as a colorless liquid: bp 80°-84° (0.1 mm); $n_D^{20}$ 1.5144; nmr ($CDCl_3$) 0.5 (3H, s), 1.2 (3H, t, J=7), 3.0 (2H, s), 3.8 (2H, q, J=7), 7.2-7.8 (5H, m).

The compounds of Table V can be prepared using the procedures of Examples 19-23.

TABLE V

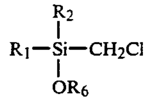

| $R_1$ | $R_2$ | $R_6$ |
|---|---|---|
| $C_2H_5$ | $CH_3$ | $CH_3$ |
| t-$C_4H_9$ | $CH_3$ | t-$C_4H_9$ |
| n-$C_4H_9$ | $CH_3$ | $C_2H_5$ |
| n-$C_{12}H_{25}$ | $C_2H_5$ | $CH_3$ |
| n-$C_{18}H_{37}$ | n-$C_6H_{13}$ | $CH_3$ |
| cyclopropyl | $CH_3$ | s-$C_4H_9$ |
| cyclohexyl | $CH_3$ | $CH_3$ |
| 1-naphthyl | i-$C_3H_7$ | i-$C_3H_7$ |
| 2-naphthyl | cyclobutyl | n-$C_3H_7$ |
| phenyl | $CH_3$ | H |
| phenyl | $CH_3$ | i-$C_3H_7$ bp 72-76° (0.1 mm) |
| phenyl | t-$C_4H_9$ | H |
| 4-phenylphenyl | n-$C_4H_9$ | $CH_3$ |
| 4-phenylphenyl | t-$C_4H_9$ | H |
| 4-phenylphenyl | $CH_3$ | $C_2H_5$ |
| 4-phenylphenyl | $CH_3$ | n-$C_4H_9$ |
| 4-chlorophenyl | n-$C_4H_9$ | n-$C_4H_9$ |
| 4-chlorophenyl | $CH_3$ | $CH_3$ |
| 4-chlorophenyl | $CH_3$ | $C_2H_5$ |
| 4-fluorophenyl | n-$C_6H_{13}$ | n-$C_3H_7$ |
| 4-fluorophenyl | $CH_3$ | $C_2H_5$ |
| 4-fluorophenyl | $CH_3$ | i-$C_3H_7$ $n_D^{22}$ 1.4827 |
| 4-phenoxyphenyl | cyclohexyl | i-$C_4H_9$ |
| 4-t-butylphenyl | n-$C_3H_7$ | s-$C_4H_9$ |
| 3-trifluoromethylphenyl | t-$C_4H_9$ | H |
| 2-methylthiophenyl | cyclopentyl | $C_2H_5$ |
| 2,4-dichlorophenyl | $CH_3$ | $CH_3$ |
| 2,4-dichlorophenyl | $CH_3$ | $C_2H_5$ |
| 2,4-dichlorophenyl | $CH_3$ | t-$C_4H_9$ |
| 2,4-dichlorophenyl | n-$C_4H_9$ | $C_2H_5$ |
| 2,3-dimethylphenyl | cyclopropyl | i-$C_3H_7$ |
| 2-methyl-5-fluorophenyl | s-$C_4H_9$ | n-$C_3H_7$ |
| 2,6-dimethoxyphenyl | 1,1-dimethylpropyl | H |
| 3-methyl-4-chlorophenyl | $C_2H_5$ | $CH_3$ |
| 3,5-dichlorophenyl | n-$C_5H_{11}$ | $C_2H_5$ |
| n-$C_{12}H_{25}$ | 2,4-dichlorophenyl | t-$C_4H_9$ |
| n-$C_{18}H_{37}$ | phenyl | $CH_3$ |
| 1-naphthyl | phenyl | $C_2H_5$ |
| phenyl | phenyl | t-$C_4H_9$ |
| 4-fluorophenyl | phenyl | $CH_3$ |
| 4-chlorophenyl | phenyl | n-$C_3H_7$ |
| 4-phenylphenyl | phenyl | $C_2H_5$ |
| 4-phenylphenyl | phenyl | s-$C_4H_9$ |
| 4-t-butylphenyl | phenyl | s-$C_4H_9$ |
| 3-fluorophenyl | phenyl | $C_2H_5$ |
| 2-methoxyphenyl | phenyl | H |
| 2-chlorophenyl | phenyl | $CH_3$ |
| 2,4-dichlorophenyl | phenyl | i-$C_3H_7$ |
| 3,5-dichlorophenyl | phenyl | n-$C_3H_7$ |
| 4-fluorophenyl | 4-fluorophenyl | t-$C_4H_9$ bp 110-111° (0.1 mm) |
| 4-fluorophenyl | 4-fluorophenyl | $C_2H_5$ |
| 4-chlorophenyl | 4-chlorophenyl | $CH_3$ |
| 4-chlorophenyl | 4-chlorophenyl | $C_2H_5$ |
| 4-chlorophenyl | 4-chlorophenyl | i-$C_3H_7$ $n_D^{22}$ 1.5650 |
| 4-phenylphenyl | 4-phenylphenyl | $CH_3$ |
| 2,4-dichlorophenyl | 2,4-dichlorophenyl | $C_2H_5$ |
| 3-trifluoromethylphenyl | 3-trifluoromethyl-phenyl | i-$C_4H_9$ |

TABLE V-continued

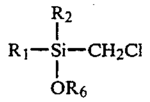

| $R_1$ | $R_2$ | $R_6$ |
|---|---|---|
| 2-methoxyphenyl | 2-methoxyphenyl | H |
| 2-chlorophenyl | 4-fluorophenyl | H |
| 3-trifluoromethylphenyl | 4-t-butylphenyl | n-$C_4H_9$ |
| 2-fluoro-4-chlorophenyl | 4-bromophenyl | i-$C_3H_7$ |
| 2,3-dimethylphenyl | 4-methylthiophenyl | $C_2H_5$ |
| 2,6-dimethoxyphenyl | 4-methoxyphenyl | H |
| 3,4-dichlorophenyl | 4-methylphenyl | i-$C_4H_9$ |

EXAMPLE 23A

Preparation of 1-Chloroethyltrichlorosilane and 2-Chloroethyltrichlorosilane A mixture of 50 ml (0.38 mol) of ethyltrichlorosilane, 36.5 ml (0.45 mol) of sulfuryl chloride, and 0.62 g (3.8 mmol) of 2,2'-azobis(2-methylpropionitrile) was heated at reflux for three hours, and the contents of the reaction pot were then distilled. The fraction boiling between 130° and 155° analyzed as 29% 1-chloroethyltrichlorosilane and 71% 2-chloroethyltrichlorosilane; yield 52.48 g (70%): nmr ($CDCl_3$) 1.7 (d, J=7 Hz, 1-chloro), 2.1 (t, J=9 Hz, 2-chloro), 3.6-3.9 (m). Distillation of the product mixture through a 60-cm Vigreux column gave a fraction bp 141°-143° that analyzed as 61% 1-chloroethyltrichlorosilane and 39% 2-chloroethyltrichlorosilane. This could be used as is for conversion to compounds of this invention.

EXAMPLE 23B

Preparation of bis(4-Fluorophenyl)-1-chloroethyl(chloro)silane and bis(4-Fluorophenyl)-2-chloroethyl(chloro)silane A mixture of 15.62 g (0.64 mol) of magnesium metal, 450 ml of tetrahydrofuran and 0.5 ml of ethylene bromide was stirred at room temperature while a solution of 67 ml (0.61 mol) of 4-fluorobromobenzene in 450 ml tetrahydrofuran was added at a rate to induce and maintain reflux. The resulting mixture was refluxed one more hour and cooled in an ice-bath, 57.65 g (0.29 mol) of a 61/39 1-chloroethyltrichlorosilane/2-chloroethyltrichlorosilane mixture in 50 ml of tetrahydrofuran was added dropwise, and the mixture was refluxed for three hours, cooled, filtered, evaporated, triturated with hexanes, filtered, evaporated, and distilled, providing 38.6 g (42%) of the title compounds as a 1 to 1 mixture: bp 140°-152° (0.5 mm); nmr ($CDCl_3$) 1.6 (d, J=7 Hz, 1-chloro), 2.0 (t, J=7 Hz, 2 -chloro), 3.6-4.0 (m), 6.8-7.2 (m) and 7.4-7.8 (m).

EXAMPLE 23C

Preparation of bis(4-Fluorophenyl)-1-chloroethyl(methyl)silane and bis(4-Fluorophenyl)-2-chloroethyl(methyl)silane A solution of 20 g (63 mmol) of a 1:1 mixture of bis(4-fluorophenyl)-1-chloroethyl(chloro)silane and bis(4-fluorophenyl)-2-chloroethyl(chloro)silane in 100 ml of tetrahydrofuran was treated dropwise with 25 ml (71 mmol) of 2.85 molar methyl magnesium bromide in tetrahydrofuran. The mixture was refluxed two hours, cooled, and diluted with saturated aqueous ammonium chloride and water. The aqueous phase was separated and extracted with ether, and the combined organic phases were washed with water and brine, dried over sodium sulfate, and evaporated to give 17.7 g (95%) of the title compounds as a 1:1 mixture: nmr ($CDCl_3$) 0.6 (s), 0.7 (s), 1.6 (d, J=7 Hz, 1-chloro), 1.8 t, J=7 Hz, 2-chloro), 3.5–4.0 (m), 6.9–7.3 (m) and 7.4–7.8 (m).

EXAMPLE 23D

Preparation of (1,1'-Biphenyl-4-yl)dimethyl-1-chloroethylsilane

A solution of 4.0 g (15.3 mmol) of (1,1'-biphenyl-4-yl)chloromethyldimethylsilane in 20 ml of tetrahydrofuran was cooled to −78°, and 12.5 ml (16.8 mmol) of 1.35 molar sec-butyllithium in hexane was slowly dripped in followed by addition of 2.42 ml (16.1 mmol) of tetramethylethylenediamine. After stirring for one hour at −78°, the solution was warmed to −55° and 1.43 ml (22.9 mmol) of methyl iodide in 5 ml of tetrahydrofuran was added dropwise. The mixture was stirred another 30 minutes at −50°, warmed to room temperature, poured into saturated aqueous ammonium chloride, and extracted with ether. The ether extracts were washed with water and brine, dried over magnesium sulfate, and evaporated to give 3.33 g (65%) of the title compound contaminated by about 18% of an impurity: nmr ($CDCl_3$) 0.3 (s, 2.7H, impurity), 0.4 (6H, s), 1.5 (3H, d, J=7 Hz), 3.5 (1H, q, J=7 Hz) and 7.3–7.7 (m, 13H).

The compounds in Table Va were made according to the procedure of Examples 23A–23D.

TABLE Va

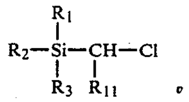

| $R_1$ | $R_2$ | $R_3$ | $R_{11}$ | |
|---|---|---|---|---|
| 4-fluorophenyl | 4-fluorophenyl | $CH_3$ | $C_2H_5$ | oil |
| 4-fluorophenyl | 4-fluorophenyl | $CH_3$ | n-$C_3H_7$ | |
| 4-fluorophenyl | 4-fluorophenyl | $CH_3$ | i-$C_3H_7$ | |
| 4-fluorophenyl | 4-fluorophenyl | $CH_3$ | n-$C_4H_9$ | |
| 4-fluorophenyl | 4-fluorophenyl | $CH_3$ | s-$C_4H_9$ | |
| 4-fluorophenyl | 4-fluorophenyl | $CH_3$ | i-$C_4H_9$ | |
| 2,4-dichlorophenyl | 4-chlorophenyl | $CH_3$ | $CH_3$ | |
| 4-phenylphenyl | $CH_3$ | $CH_3$ | $C_2H_5$ | |
| 4-phenylphenyl | $CH_3$ | $CH_3$ | n-$C_3H_7$ | oil |
| 4-phenylphenyl | $CH_3$ | $CH_3$ | i-$C_3H_7$ | oil |
| 4-phenylphenyl | $CH_3$ | $CH_3$ | n-$C_4H_9$ | |

EXAMPLE 24

Preparation of (1,1'-Biphenyl-4-yl)dimethyl(1H-1,2,4-triazol-1-ylmethyl)silane A mixture of 2.6 g (0.010 mol) of (1,1'-biphenyl-4-yl)chloromethyldimethylsilane and 1.1 g (0.012 mol) of 1,2,4-triazole sodium salt in 5 ml of dimethylformamide was warmed to 80°–90° for 2 hours, cooled, diluted with water, and extracted with ether. The ether solution was washed with water and brine, dried over magnesium sulfate, and evaporated to leave 2.3 g of colorless solid, m.p. 79°–86°. Recrystallization from a mixture of 25 ml of hexanes and 2 ml of ethyl acetate gave 1.1 g (38%) of the title compound: m.p. 92°–93°; ir (Nujol®) 1255, 1130, 1000, 825, 760, 695 $cm^{-1}$; nmr ($CDCl_3$) 0.4 (6H, s), 3.9 (2H, s), 7.2–7.7 (9H, m), 7.8 (1H, s), 7.9 (1H, s); analysis for $C_{17}H_{19}N_3Si$ (mw 293.43):

Calculated C, 69.58; H, 6.53; N, 14.32; Found C, 70.0; H, 6.6; N, 13.9; 69.8; 6.7; 13.8.

An equimolar mixture of 1,2,4-triazole and sodium methoxide can be used instead of preformed triazole sodium salt. Note that these reagents must be combined before the silane is added, since chloromethylsilanes react very vigorously with sodium methoxide in dimethylformamide, giving undesired products.

EXAMPLE 25

Isolation of (1,1'-Biphenyl-4-yl)dimethyl(4H-1,2,4-triazol-4-ylmethyl)silane A 5-g sample of once-crystallized 1,1'-(biphenyl-4-yl)dimethyl(1H-1,2,4-triazol-1-ylmethyl)silane, prepared as in Example 24 using sodium methoxide-1,2,4-triazole, was subjected to high pressure liquid chromatography (Waters Prep PAK-500 silica gel cartridge, 250 ml per minute flow rate). Elution with ethyl acetate-hexane 50:50 removed first some minor impurities and then provided the pure 1H-1,2,4-triazole-1-ylmethyl compound, m.p. 99°–100°. Continued elution with ethyl acetate-acetonitrile 80:20 provided a small amount of the title compound as a colorless solid: m.p. 130°–133° C.; nmr ($CDCl_3$) 0.4 (6H, s), 3.7 (2H, s), 7.2–7.7 (9H, m), 7.9 (2H, s); microanalysis for $C_{17}H_{19}N_3Si$ (mw 293.43):

Calculated: C, 69.58; H, 6.53; N, 14.32. Found: C, 69.0; H, 6.7; N, 13.9. 69.3; 6.7; 14.2.

EXAMPLE 26

Preparation of Dimethyl(phenyl)(1H-1,2,4-triazol-1-ylmethyl)silane

A mixture of 9.0 ml (9.2 g, 0.050 mol) of chloromethyldimethylphenylsilane and 5.5 g (0.060 mol) of 1,2,4-triazole sodium salt in 25 ml of dimethylformamide was stirred and warmed to 90°–95° C. for 2 hours, cooled, diluted with water, and extracted with ether. The ether solution was washed with water and brine, dried over magnesium sulfate, and evaporated to leave 8.1 g (75%) of a pale brown oil, $n_D^{22}$ 1.5350, containing the title compound and minor impurities as judged by nmr. A purer sample was obtained by distillation: bp 99° (0.02 mm); $n_D^{20}$ 1.5403; nmr ($CDCl_3$) 0.4 (6H, s), 3.8 (2H, s), 7.2–7.7 (5H, m), 7.7 (1H, s), 7.8 (1H, s); analysis for $C_{11}H_{15}N_3Si$ (mw 217.34):

Calculated C, 60.78; H, 6.96; N, 19.33; Found C, 60.7; H, 7.0; N, 16.9; 60.2; H, 7.0; N, 16.8.

EXAMPLE 27

Preparation of (4-Chlorophenyl)dimethyl(1H-1,2,4-triazol-1-ylmethyl)silane

A mixture of 2.2 g (0.010 mol) of chloromethyl(4-chlorophenyl)dimethylsilane and 1.1 g (0.012 mol) of 1,2,4-triazole sodium salt in 5 ml of dimethylformamide was warmed to 80°–90° for 2 hours, diluted with water, and extracted with ether. The ether solution was washed with water and brine, dried over magnesium sulfate, and evaporated to leave 2:1 g (83%) of the title compound as a yellow liquid: $n_D^{21}$ 1.5428; ir (neat) 1555, 1470, 1245, 1130, 1080, 1010, 835, 805, 795, 735 $cm^{-1}$; nmr ($CDCl_3$) 0.4 (6H, s), 3.8 (2H, s), 7.4 (4H, broad s), 7.8 (1H, s), 7.9 (1H, s).

EXAMPLE 28

Preparation of (2,4-Dichlorophenyl)dimethyl(1H-1,2,4-triazol-1-ylmethyl)silane

A mixture of 5.1 g (0.020 mol) of chloromethyl(2,4-dichlorophenyl)dimethysilane and 2.0 g (0.022 mol) of 1,2,4-triazole sodium salt in 10 ml of dry dimethylformamide was stirred at 80°-90° for 2 hours. The resulting slurry was cooled, diluted with water, and washed with ether. The ether extracts were washed with several portions of water and once with brine, dried over magnesium sulfate, and evaporated to leave 4.6 g (81%) of the title compound as a pale yellow liquid: $n_D^{23}$ 1.5580; ir (neat) 1550, 1485, 1440, 1345, 1260, 1240, 1130, 1085, 1025, 1005, 835 $cm^{-1}$; nmr ($CDCl_3$) 0.5 (6H, s), 4.1 (2H, s), 7.2-7.5 (3H, m), 7.8 (1H, s), 7.9 (1H, s).

EXAMPLE 29

Preparation of bis(4-Chlorophenyl)methyl(1H,-1,2,4-triazol-1-ylmethyl)silane

A mixture of 6.3 g (0.020 mol) of chloromethylbis(4-chlorophenyl)methylsilane and 2.0 g (0.022 mol) of 1,2,4-triazole sodium salt in 10 ml of dry dimethylformamide was stirred at 80° C. for 4 hours. The resulting slurry was cooled, diluted with water, and washed with ether. The ether extracts were washed with several portions of water and once with brine, dried over magnesium sulfate, and evaporated to leave 5.4 g of yellow oil. Kugelrohr distillation at 120°-150° (airbath)/0.05 mm gave 4.0 g (58% of the title compound as a pale yellow oil: $n_D^{26}$ 1.5966; nmr ($CDCl_3$) 0.7 (3H, s), 4.1 (2H, s), 7.2-7.5 (8H, m), 7.8 (1H, s), 7.9 (1H, s).

In a similar experiment, evaporation of the ether extracts gave a gummy solid that was triturated with hexanes to give the title compound as a colorless solid, m.p. 76°-80°.

EXAMPLE 30

Preparation of bis(4-Fluorophenyl)methyl(1H,-1,2,4-triazol-1-ylmethyl)silane and its hydrochloride salt A mixture of 4.2 g (0.015 mol) of (chloromethyl)bis(4-fluorophenyl)methylsilane and 1.4 g (0.015 mol) of 1,2,4-triazole sodium salt in 8 ml of dimethylformamide was stirred at 80° for 2 hours. The resulting slurry was cooled, diluted with water, and washed with ether. The ether extracts were washed with several portion of water and once with brine, dried over magnesium sulfate, and evaporated to leave 4.0 g of a pale yellow oil. Impurities were removed by Kugelrohr distillation at 120°-125° (0.05 mm), leaving behind 2.3 g (49%) of the title compound as a yellow oil: $n_D^{21}$ 1.5538; ir (neat) 3065, 3030, 2960, 2925, 1590, 1500, 1270, 1235, 1165, 1110, 1010, 830, 790 $cm^{-1}$; nmr ($CDCl_3$): 0.7 (3H, s), 4.2 (2H, s), 7.1 (4H, t, J=9), 7.5 (4H, d of d, J=6 and 9), 7.8 (1H, s) and 7.9 (1H, s). A sample prepared similarly was crystallized from hexane at −20° C. to give colorless solid, m.p. 52°-53°.

The hydrochloride salt of the title compound was prepared as follows. A solution of 5.0 g (0.016 mol) of [bis(4-fluorophenyl)]methyl(1H-1,2,4-triazol-1-ylmethyl)silane in 100 ml of toluene was stirred while HCl gas was passed over the solution surface until no further precipitate formed. The colorless solid was collected by filtration, washed with toluene and petroluem ether, and air-dried to give 5.1 g (91%) of the hydrochloride salt, m.p. 195°-197°. Recrystallization from 100 ml of hot ethanol gave 3.5 g of colorless crystals, m.p. 201°-203°. Acid salts of the other triazoles of this invention can be prepared similarly.

By applying the procedures of Examples 24 and 26-30 to appropriate chloromethylsilanes, the compounds of Table VI can be prepared.

TABLE VI

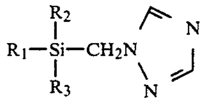

| $R_1$ | $R_2$ | $R_3$ | |
|---|---|---|---|
| $C_2H_5$ | $CH_3$ | $CH_3$ | $n_D^{22}$ 1.4713 |
| i-$C_3H_7$ | $CH_3$ | $CH_3$ | |
| n-$C_4H_9$ | $CH_3$ | $CH_3$ | $n_D^{19}$ 1.4687 |
| t-$C_4H_9$ | $CH_3$ | $CH_3$ | |
| n-$C_{12}H_{25}$ | $CH_3$ | $CH_3$ | $n_D^{23}$ 1.4626 |
| n-$C_{14}H_{29}$ | $CH_3$ | $CH_3$ | |
| n-$C_{18}H_{37}$ | $CH_3$ | $CH_3$ | $n_D^{21}$ 1.4597 |
| cyclopropyl | $CH_3$ | $CH_3$ | |
| cyclobutyl | $CH_3$ | $CH_3$ | |
| cyclopentyl | $CH_3$ | $CH_3$ | |
| cyclohexyl | $CH_3$ | $CH_3$ | $n_D^{22}$ 1.4906 |
| 1-naphthyl | $CH_3$ | $CH_3$ | $n_D^{23}$ 1.6051 |
| 2-naphthyl | $CH_3$ | $CH_3$ | |
| 4-bromophenyl | $CH_3$ | $CH_3$ | $n_D^{20}$ 1.5647 |
| 4-fluorophenyl | $CH_3$ | $CH_3$ | bp 108° (0.2 mm) |
| 4-methoxyphenyl | $CH_3$ | $CH_3$ | $n_D^{26}$ 1.5401 |
| 4-phenoxyphenyl | $CH_3$ | $CH_3$ | $n_D^{22}$ 1.5754 |
| 4-(4-chlorophenoxy)phenyl | $CH_3$ | $CH_3$ | $n_D^{22}$ 1.5703 |
| 4-(4-fluorophenoxy)phenyl | $CH_3$ | $CH_3$ | |
| 4-(4-trifluoromethylphenoxy)phenyl | $CH_3$ | $CH_3$ | |
| 4-(4-methylphenoxy)phenyl | $CH_3$ | $CH_3$ | |
| 4-thiomethylphenyl | $CH_3$ | $CH_3$ | $n_D^{23}$ 1.5790 |
| 4-trifluoromethylphenyl | $CH_3$ | $CH_3$ | $n_D^{22}$ 1.4909 |
| 4-methylphenyl | $CH_3$ | $CH_3$ | $n_D^{21}$ 1.5350 |
| 4-methylsulfonylphenyl | $CH_3$ | $CH_3$ | $n_D^{21}$ 1.5538 |

TABLE VI-continued

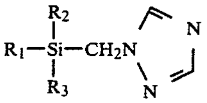

| $R_1$ | $R_2$ | $R_3$ | |
|---|---|---|---|
| 4-i-propylphenyl | $CH_3$ | $CH_3$ | |
| 4-t-butylphenyl | $CH_3$ | $CH_3$ | $n_D^{23}$ 1.5125 |
| 4-cyclohexylphenyl | $CH_3$ | $CH_3$ | $n_D^{21}$ 1.5235 |
| 4-trifluoromethoxyphenyl | $CH_3$ | $CH_3$ | $n_D^{22}$ 1.4768 |
| 4-(4-chlorophenyl)phenyl | $CH_3$ | $CH_3$ | |
| 4-(4-bromophenyl)phenyl | $CH_3$ | $CH_3$ | $n_D^{22}$ 1.5802 |
| 4-(4-methylphenyl)phenyl | $CH_3$ | $CH_3$ | |
| 4-(4-trifluoromethylphenyl)phenyl | $CH_3$ | $CH_3$ | |
| 4-(4-fluorophenyl)phenyl | $CH_3$ | $CH_3$ | |
| 3-phenylphenyl | $CH_3$ | $CH_3$ | $n_D^{21}$ 1.5939 |
| 3-trifluoromethylphenyl | $CH_3$ | $CH_3$ | $n_D^{20}$ 1.4845 |
| 3-chlorophenyl | $CH_3$ | $CH_3$ | m.p. 37-43° |
| 2-trifluoromethylphenyl | $CH_3$ | $CH_3$ | $n_D^{23}$ 1.4964 |
| 2-phenylphenyl | $CH_3$ | $CH_3$ | $n_D^{22}$ 1.5900 |
| 2-chlorophenyl | $CH_3$ | $CH_3$ | $n_D^{22}$ 1.5442 |
| 2-methoxyphenyl | $CH_3$ | $CH_3$ | $n_D^{21}$ 1.5216 |
| 2,3-dimethylphenyl | $CH_3$ | $CH_3$ | |
| 2,3-dimethoxyphenyl | $CH_3$ | $CH_3$ | $n_D^{22}$ 1.5322 |
| 2,4-difluorophenyl | $CH_3$ | $CH_3$ | |
| 2-fluoro-4-chlorophenyl | $CH_3$ | $CH_3$ | |
| 2-chloro-4-fluorophenyl | $CH_3$ | $CH_3$ | |
| 2-chloro-4-phenylphenyl | $CH_3$ | $CH_3$ | |
| 2-fluoro-4-phenylphenyl | $CH_3$ | $CH_3$ | |
| 2-methyl-5-chlorophenyl | $CH_3$ | $CH_3$ | |
| 2,6-dimethoxyphenyl | $CH_3$ | $CH_3$ | $n_D^{23}$ 1.5404 |
| 2,6-dimethylphenyl | $CH_3$ | $CH_3$ | |
| 3,4-dichlorophenyl | $CH_3$ | $CH_3$ | $n_D^{22}$ 1.5602 |
| 3-methyl-4-fluorophenyl | $CH_3$ | $CH_3$ | |
| 3,5-dichlorophenyl | $CH_3$ | $CH_3$ | m.p. 63-69° |
| $C_2H_5$ | $C_2H_5$ | $CH_3$ | |
| i-$C_3H_7$ | cyclohexyl | $CH_3$ | |
| n-$C_4H_9$ | n-$C_4H_9$ | $CH_3$ | $n_D^{22}$ 1.4672 |
| n-$C_{10}H_{21}$ | cyclopropyl | $CH_3$ | |
| n-$C_{12}H_{25}$ | n-$C_3H_7$ | $CH_3$ | |
| n-$C_{14}H_{29}$ | i-$C_3H_7$ | $CH_3$ | |
| n-$C_{18}H_{37}$ | 3-methylbutyl | $CH_3$ | |
| cyclopropyl | n-$C_6H_{13}$ | $CH_3$ | |
| cyclopentyl | cylopentyl | $CH_3$ | |
| cyclohexyl | cyclohexyl | $CH_3$ | |
| 1-naphthyl | n-$C_4H_9$ | $CH_3$ | |
| 1-naphthyl | t-$C_4H_9$ | $CH_3$ | |
| 2-naphthyl | n-$C_5H_{11}$ | $CH_3$ | |
| phenyl | n-$C_3H_7$ | $CH_3$ | |
| phenyl | n-$C_4H_9$ | $CH_3$ | $n_D^{21}$ 1.5297 |
| phenyl | 1,1-dimethylpropyl | $CH_3$ | |
| phenyl | n-$C_6H_{13}$ | $CH_3$ | |
| 4-phenylphenyl | $C_2H_5$ | $CH_3$ | |
| 4-phenylphenyl | n-$C_4H_9$ | $CH_3$ | $n_D^{22}$ 1.5838 |
| 4-bromophenyl | i-$C_3H_7$ | $CH_3$ | |
| 4-chlorophenyl | n-$C_4H_9$ | $CH_3$ | $n_D^{21}$ 1.5344 |
| 4-fluorophenyl | n-$C_4H_9$ | $CH_3$ | $n_D^{22}$ 1.5120 |
| 4-phenoxyphenyl | t-$C_4H_9$ | $CH_3$ | |
| 4-i-propylphenyl | cyclopropyl | $CH_3$ | |
| 4-t-butylphenyl | i-$C_4H_9$ | $CH_3$ | |
| 3-phenylphenyl | i-$C_4H_9$ | $CH_3$ | |
| 3-trifluoromethylphenyl | s-$C_4H_9$ | $CH_3$ | |
| 3-chlorophenyl | n-$C_5H_{11}$ | $CH_3$ | |
| 2-methoxyphenyl | t-$C_4H_9$ | $CH_3$ | |
| 2-thiomethylphenyl | cyclobutyl | $CH_3$ | |
| 2-phenylphenyl | i-$C_4H_9$ | $CH_3$ | |
| 2,4-dichlorophenyl | n-$C_4H_9$ | $CH_3$ | $n_D^{23}$ 1.5411 |
| 2,4-dichlorophenyl | cyclopropyl | $CH_3$ | |
| 2,3-dimethylphenyl | n-$C_3H_7$ | $CH_3$ | |
| 2-methyl-5-fluorophenyl | cyclopentyl | $CH_3$ | |
| 2,5-dimethoxyphenyl | 4-methylpentyl | $CH_3$ | |
| 2,6-dimethylphenyl | 1-methylbutyl | $CH_3$ | |
| 3,4-dichlorophenyl | n-$C_5H_{11}$ | $CH_3$ | |
| 3,5-dichlorophenyl | n-$C_4H_9$ | $CH_3$ | |
| 3,5-dichlorophenyl | cyclohexyl | $CH_3$ | |
| 3-methyl-4-chlorophenyl | cyclopropyl | $CH_3$ | |
| phenyl | phenyl | $CH_3$ | $n_D^{22}$ 1.5852 |
| 4-fluorophenyl | phenyl | $CH_3$ | $n_D^{20}$ 1.5718 |
| 4-chlorophenyl | phenyl | $CH_3$ | $n_D^{22}$ 1.5926 |
| 4-bromophenyl | phenyl | $CH_3$ | $n_D^{22}$ 1.6076 |
| 4-phenylphenyl | phenyl | $CH_3$ | $n_D^{21}$ 1.6328 |

TABLE VI-continued

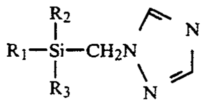

| $R_1$ | $R_2$ | $R_3$ | |
|---|---|---|---|
| 4-t-butylphenyl | phenyl | $CH_3$ | |
| 4-thiomethylphenyl | phenyl | $CH_3$ | |
| 4-phenoxyphenyl | phenyl | $CH_3$ | |
| 4-trifluoromethoxyphenyl | phenyl | $CH_3$ | |
| 4-methylsulfonylphenyl | phenyl | $CH_3$ | |
| 4-cyclohexylphenyl | phenyl | $CH_3$ | |
| 4-(4-fluorophenyl)phenyl | phenyl | $CH_3$ | |
| 3-trifluoromethylphenyl | phenyl | $CH_3$ | |
| 2-chlorophenyl | phenyl | $CH_3$ | $n_D^{20}$ 1.5742 |
| 2-methoxyphenyl | phenyl | $CH_3$ | |
| 2,4-dichlorophenyl | phenyl | $CH_3$ | $n_D^{23}$ 1.5941 |
| 2-chloro-4-phenylphenyl | phenyl | $CH_3$ | |
| 2-fluoro-4-phenylphenyl | phenyl | $CH_3$ | |
| 3,5-dichlorophenyl | phenyl | $CH_3$ | |
| 2,5-dimethoxyphenyl | phenyl | $CH_3$ | |
| 2,6-dimethoxyphenyl | phenyl | $CH_3$ | |
| 4-bromophenyl | 4-bromophenyl | $CH_3$ | $n_D^{21}$ 1.6245 |
| 4-phenylphenyl | 4-phenylphenyl | $CH_3$ | m.p. 42–46° |
| 4-methylphenyl | 4-methylphenyl | $CH_3$ | bp 169–173° (0.1 mm) |
| 4-methoxyphenyl | 4-methoxyphenyl | $CH_3$ | $n_D^{21}$ 1.5890 |
| 3-trifluoromethylphenyl | 3-trifluoromethylphenyl | $CH_3$ | |
| 2-chlorophenyl | 2-chlorophenyl | $CH_3$ | $n_D^{21}$ 1.5965 |
| 2-methoxyphenyl | 2-methoxyphenyl | $CH_3$ | |
| 2,4-dichlorophenyl | 2,4-dichlorophenyl | $CH_3$ | $n_D^{22}$ 1.6009 |
| 3,5-dichlorophenyl | 3,5-dichlorophenyl | $CH_3$ | |
| 2-chlorophenyl | 4-chlorophenyl | $CH_3$ | $n_D^{20}$ 1.5918 |
| 2-chlorophenyl | 4-fluorophenyl | $CH_3$ | |
| 4-phenylphenyl | 4-chlorophenyl | $CH_3$ | |
| 4-phenylphenyl | 4-fluorophenyl | $CH_3$ | $n_D^{22}$ 1.6151 |
| 4-phenylphenyl | 2,4-dichlorophenyl | $CH_3$ | |
| 4-fluorophenyl | 2,4-dichlorophenyl | $CH_3$ | |
| 4-chlorophenyl | 2,4-dichlorophenyl | $CH_3$ | |
| 1-naphthyl | 2,6-dimethoxyphenyl | $CH_3$ | |
| 4-phenoxyphenyl | 3,4-dichlorophenyl | $CH_3$ | |
| $C_2H_5$ | $C_2H_5$ | $C_2H_5$ | |
| i-$C_3H_7$ | i-$C_3H_7$ | i-$C_3H_7$ | |
| n-$C_4H_9$ | n-$C_4H_9$ | n-$C_4H_9$ | |
| n-$C_8H_{17}$ | $C_2H_5$ | cyclopentyl | |
| n-$C_{14}H_{29}$ | cyclopropyl | 1-methylbutyl | |
| n-$C_{18}H_{37}$ | n-$C_6H_{13}$ | n-$C_6H_{13}$ | |
| cyclopropyl | $C_2H_5$ | s-$C_4H_9$ | |
| cyclohexyl | n-$C_3H_7$ | n-$C_3H_7$ | |
| 1-naphthyl | n-$C_4H_9$ | n-$C_4H_9$ | |
| 2-naphthyl | n-$C_4H_9$ | cyclobutyl | |
| phenyl | cyclopropyl | n-$C_6H_{13}$ | |
| 4-phenylphenyl | $C_2H_5$ | $C_2H_5$ | |
| 4-phenylphenyl | n-$C_4H_9$ | n-$C_4H_9$ | |
| 4-phenylphenyl | n-$C_6H_{13}$ | n-$C_6H_{13}$ | |
| 4-phenylphenyl | cyclohexyl | cyclohexyl | |
| 4-chlorophenyl | n-$C_4H_9$ | n-$C_4H_9$ | |
| 4-fluorophenyl | n-$C_3H_7$ | n-$C_3H_7$ | |
| 4-phenoxyphenyl | n-$C_4H_9$ | cyclohexyl | |
| 4-(4-chlorophenoxy)phenyl | n-$C_4H_9$ | n-$C_4H_9$ | |
| 4-t-butylphenyl | s-$C_4H_9$ | i-$C_4H_9$ | |
| 3-methoxyphenyl | $C_2H_5$ | t-$C_4H_9$ | |
| 3-trifluoromethylphenyl | s-$C_4H_9$ | s-$C_4H_9$ | |
| 2-thiomethylphenyl | i-$C_3H_7$ | 3-methylbutyl | |
| 2-phenylphenyl | cyclohexyl | cyclohexyl | |
| 2,4-dichlophenyl | n-$C_4H_9$ | n-$C_4H_9$ | |
| 2,6-dimethylphenyl | t-$C_4H_9$ | t-$C_4H_9$ | |
| 3,5-dichlorophenyl | cyclopentyl | cyclopentyl | |
| 3-methyl-4-chlorophenyl | s-$C_4H_9$ | s-$C_4H_9$ | |
| 2-methyl-5-fluorophenyl | n-$C_4H_9$ | | |
| $C_2H_5$ | phenyl | phenyl | |
| cyclohexyl | phenyl | phenyl | |
| n-$C_{18}H_{37}$ | phenyl | phenyl | |
| n-$C_4H_9$ | 4-chlorophenyl | 4-chlorophenyl | |
| n-$C_{12}H_{25}$ | 4-chlorophenyl | 4-chlorophenyl | |
| 1-naphthyl | 4-fluorophenyl | 4-fluorophenyl | |
| cyclopropyl | phenyl | 4-t-butylphenyl | |
| n-$C_4H_9$ | phenyl | 4-phenylphenyl | |
| t-$C_4H_9$ | phenyl | 2,4-dichlorophenyl | |
| n-$C_3H_7$ | phenyl | 3-trifluoromethylphenyl | |
| i-$C_4H_9$ | phenyl | 3,5-dichlorophenyl | |

TABLE VI-continued

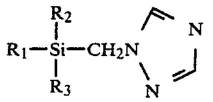

| $R_1$ | $R_2$ | $R_3$ | |
|---|---|---|---|
| cyclopentyl | phenyl | 2,6-dimethoxyphenyl | |
| n-$C_{14}H_{29}$ | 4-chlorophenyl | 2-fluorophenyl | |
| n-$C_4H_9$ | 4-fluorophenyl | 4-4-phenylphenyl | |
| phenyl | phenyl | phenyl | m.p. 118–121° |
| 4-chlorophenyl | 4-chlorophenyl | 4-chlorophenyl | m.p. 136–138° |
| 4-fluorophenyl | 4-fluorophenyl | 4-fluorophenyl | m.p. 84–85° |
| 4-phenylphenyl | 4-phenylphenyl | 4-phenylphenyl | |
| 2,4-dichlorophenyl | 2,4-dichlorophenyl | 2,4-dichlorophenyl | |
| phenyl | 4-fluorophenyl | 4-fluorophenyl | |
| phenyl | 4-chlorophenyl | 4-chlorophenyl | |
| phenyl | 4-phenylphenyl | 4-phenylphenyl | |
| phenyl | 2,4-dichlorophenyl | 2,4-dichlorophenyl | |
| 2-naphthyl | 4-methylthiophenyl | 4-methylthiophenyl | |
| 4-chlorophenyl | 2-methoxyphenyl | 2-methoxyphenyl | |
| 4-chlorophenyl | 3-chlorophenyl | | |
| phenyl | 2-chlorophenyl | 4-fluorophenyl | |
| phenyl | 4-chlorophenyl | 4-phenylphenyl | |
| 1-naphthyl | 4-bromophenyl | 3-methylphenyl | |
| 4-phenoxyphenyl | 3,5-dimethylphenyl | 3,4-dichlorophenyl | |

EXAMPLE 31

Preparation of (3,5-Dimethyl-1H-1,2,4-triazol-1-ylmethyl)[bis(4-fluorophenyl)]methylsilane The title compound is prepared by applying the procedure of Example 30 to equimolar quantities of chloromethyl[bis(4-fluorophenyl)]methylsilane and 3,5-dimethyl-1,2,4-triazole sodium salt.

Related compounds may be made by substituting salts of 3-methyl-1,2,4-triazole for the 3,5-dimethyltriazole salt.

EXAMPLE 32

Preparation of (1,1'-Biphenyl-4-yl)dimethyl(5-methyl-1H-1,2,4-triazol-1-ylmethyl)silane A solution of 5.9 g (0.020 mol) of (1,1'-biphenyl-4-yl)dimethyl(1H-1,2,4-triazol-1-ylmethyl)silane in 40 ml of dry tetrahydrofuran was chilled to −40° under $N_2$ and stirred while 12.5 ml (0.020 mol) of 1.6 molar n-butyllithium in hexane was added dropwise. The resulting yellow solution was stirred another 15 minutes at −40°, treated with 1.9 ml (4.2 g, 0.030 mol) of methyl iodide, and allowed to warm to room temperature. The resulting solution was diluted with water and extracted with hexanes. Washing the organic extracts with water and brine, drying over magnesium sulfate, and evaporation give 5.7 g of solid, which was purified by dry-column chromatography over silica gel (ethyl acetate elution) to give 1.1 g of crude product. Recrystallization from 12 ml of 3:1 hexanesethyl acetate then gave 0.97 g (16%) of the title compound as an off white solid: m.p. 95°–98°; ir (Nujol®) 1590, 1270, 1250, 1180, 1120, 830, 765, 700 $cm^{-1}$; nmr ($CDCl_3$) 0.5 (6H, s), 2.2 (3H, s), 3.7 (2H, s), 7.2–7.7 (9H, m), 7.8 (1H, s).

Although the indicated structure is preferred for chemical reasons, the position of the methyl group on the triazole ring has not been proven, and it is possible that the product is (1,1'-biphenyl-4-yl)dimethyl(3-methyl-1H-1,2,4-triazol-1-ylmethyl)silane.

The procedures of Examples 31 and 32 may be used to prepare the compounds of Table VII.

TABLE VII

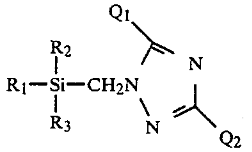

| $R_1$ | $R_2$ | $R_3$ | $Q_1$ | $Q_2$ |
|---|---|---|---|---|
| $C_2H_5$ | $CH_3$ | $CH_3$ | $CH_3$ | $CH_3$ |
| n-$C_{18}H_{37}$ | $CH_3$ | $CH_3$ | H | $CH_3$ |
| cyclohexyl | $CH_3$ | $CH_3$ | $CH_3$ | $CH_3$ |
| 1-naphthyl | $CH_3$ | $CH_3$ | $CH_3$ | $CH_3$ |
| phenyl | $CH_3$ | $CH_3$ | H | $CH_3$ |
| phenyl | $CH_3$ | $CH_3$ | $CH_3$ | H |
| 4-phenylphenyl | $CH_3$ | $CH_3$ | $CH_3$ | $CH_3$ |
| 4-(4-fluorophenyl)phenyl | $CH_3$ | $CH_3$ | $CH_3$ | $CH_3$ |
| 4-phenoxyphenyl | $CH_3$ | $CH_3$ | $CH_3$ | $CH_3$ |
| 3-trifluoromethylphenyl | $CH_3$ | $CH_3$ | $CH_3$ | $CH_3$ |
| 2-methoxyphenyl | $CH_3$ | $CH_3$ | $CH_3$ | $CH_3$ |
| 2,4-dichlorophenyl | $CH_3$ | $CH_3$ | $CH_3$ | $CH_3$ |
| 2-chloro-4-phenylphenyl | $CH_3$ | $CH_3$ | $CH_3$ | $CH_3$ |
| phenyl | n-$C_4H_9$ | $CH_3$ | $CH_3$ | $CH_3$ |
| 4-phenylphenyl | n-$C_4H_9$ | $CH_3$ | H | $CH_3$ |
| 2,4-dichlorophenyl | n-$C_6H_{13}$ | $CH_3$ | $CH_3$ | $CH_3$ |
| 4-(4-chlorophenoxy)-phenyl | cyclohexyl | $CH_3$ | $CH_3$ | $CH_3$ |
| phenyl | phenyl | $CH_3$ | H | $CH_3$ |
| 4-fluorophenyl | phenyl | $CH_3$ | $CH_3$ | $CH_3$ |
| 4-fluorophenyl | phenyl | $CH_3$ | H | $CH_3$ |
| 4-chlorophenyl | phenyl | $CH_3$ | H | $CH_3$ |
| 4-fluorophenyl | 4-fluorophenyl | $CH_3$ | H | $CH_3$ |
| 4-fluorophenyl | 4-fluorophenyl | $CH_3$ | $CH_3$ | H |
| 4-chlorophenyl | 4-chlorophenyl | $CH_3$ | H | $CH_3$ |
| 4-chlorophenyl | 4-chlorophenyl | $CH_3$ | $CH_3$ | $CH_3$ |
| 2-chlorophenyl | 4-chlorophenyl | $CH_3$ | H | $CH_3$ |
| 2,4-dichlorophenyl | 2,4-dichloro-phenyl | $CH_3$ | $CH_3$ | $CH_3$ |
| n-$C_{18}H_{37}$ | n-$C_6H_{13}$ | n-$C_6H_{13}$ | $CH_3$ | $CH_3$ |
| 1-naphthyl | n-$C_4H_9$ | n-$C_4H_9$ | H | $CH_3$ |
| phenyl | phenyl | phenyl | H | $CH_3$ |
| phenyl | phenyl | phenyl | $CH_3$ | H |
| phenyl | phenyl | phenyl | $CH_3$ | $CH_3$ |

EXAMPLE 32A

Preparation of bis(4-Fluorophenyl)methyl[1-(1H-1,2,4-triazol-1-yl)ethyl]silane

A mixture of 1.78 g (37 mmol) of 50% sodium hydride, 30 ml of dimethylformamide, and 2.56 g (37 mmol) of 1H-1,2,4-triazole was stirred at 50° for one hour, and a solution of 10 g (33.7 mmol) of a 1:1 mixture of bis(4-fluorophenyl)-1-chloroethyl(methyl)silane and bis(4-fluorophenyl)-2-chloroethyl(methyl)silane in 10 ml of dimethylformamide was added. The mixture was stirred at 50° for 64 hours, cooled, diluted with water, and extracted with ether. The ether extracts were washed with water and brine, dried over sodium sulfate, and evaporated to leave a viscous oil. Chromatography over silica gel eluting with dichloromethane followed by 3% methanol in dichloromethane provided 1.37 g (12%) of the title compound as a viscous oil: nmr ($CDCl_3$) 0.7 (3H, s), 1.6 (3H, d, J=7 Hz), 4.5 (1H, q, J=7 Hz), 6.9–7.7 (8H, m), 7.9 (1H, s), and 8.0 (1H, s).

EXAMPLE 32B

Preparation of (1,1'-Biphenyl-4-yl)dimethyl[1-(1H-1,2,4-triazol-1-yl)ethyl]silane A mixture of 2.50 g (7.46 mmol) of 82% pure (1,1'-biphenyl-4-yl)dimethyl-1-chloroethylsilane and 1.60 g (15 mmol) of 1H-1,2,4-triazole potassium salt in 15 ml of dimethylformamide was stirred at 50° for 64 hours, cooled, diluted with water, and extracted with ether. The ether extracts were washed with water and brine, dried over magnesium sulfate, and evaporated to leave a viscous oil. Chromatography over silica gel eluting with 2% methanol in dichloromethane gave 0.30 g (13%) of the title compound as a pale yellow oil: nmr ($CDCl_3$) 0.38 and 0.42 (total 6H, two equal s), 1.6 (3H, d, J=7 Hz), 4.2 (1H, q, J=7 Hz), 7.3–7.8 (9H, m), 7.9 (1H, s) and 8.0 (1H, s).

The compounds in Table VIIa were made according to the procedures of Examples 32A and 32B.

TABLE VIIa

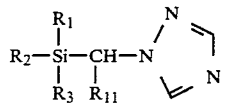

| $R_1$ | $R_2$ | $R_3$ | $R_{11}$ |
|---|---|---|---|
| 4-fluorophenyl | 4-fluorophenyl | $CH_3$ | $C_2H_5$ |
| 4-fluorophenyl | 4-fluorophenyl | $CH_3$ | $n-C_3H_7$ |
| 4-fluorophenyl | 4-fluorophenyl | $CH_3$ | $i-C_3H_7$ |
| 4-fluorophenyl | 4-fluorophenyl | $CH_3$ | $n-C_4H_9$ |
| 4-fluorophenyl | 4-fluorophenyl | $CH_3$ | $s-C_4H_9$ |
| 4-fluorophenyl | 4-fluorophenyl | $CH_3$ | $i-C_4H_9$ |
| 2,4-dichlorophenyl | 4-chlorophenyl | $CH_3$ | $CH_3$ |
| 4-phenylphenyl | $CH_3$ | $CH_3$ | $C_2H_5$ |
| 4-phenylphenyl | $CH_3$ | $CH_3$ | $n-C_3H_7$ |
| 4-phenylphenyl | $CH_3$ | $CH_3$ | $i-C_3H_7$ oil |
| 4-phenylphenyl | $CH_3$ | $CH_3$ | $n-C_4H_9$ |

EXAMPLE 33

Preparation of the 1:1 complex of (1,1'-Biphenyl-4-yl)dimethyl(1H-1,2,4-triazol-1-ylmethyl)silane and Cuprous Chloride A mixture of 5.0 g (0.017 mol) of (1,1'-biphenyl-4-yl)dimethyl(1H-1,2,4-triazol-1-ylmethyl)silane and 1.7 g (0.017 mol) of cuprous chloride in 170 ml of tetrahydrofuran was refluxed under $N_2$ for 30 minutes, and the resulting deep green solution was evaporated to leave the title compound as a dark greenish-brown solid: m.p. 85°–90°; ir (Nujol ®) 3110, 1590, 1280, 1250, 1120, 1010, 990, 840, 825, 760, 700 $cm^{-1}$.

The following metal complexes of (1,1'-biphenyl-4-yl)dimethyl(1H-1,2,4-triazol-4-ylmethyl)silane were prepared similarly:

1:1 Complex with cupric chloride: m.p. 83°–87°
2:1 Complex with cupric chloride: m.p. 85°–92°
1:1 Complex with zinc chloride: $n_D^{21}$ 1.5737
1:1 Complex with manganous sulfate: m.p. 244°–250° (decomp.)

EXAMPLE 34

Preparation of the 4-Dodecylbenzenesulfonate Salt of (1,1'-Biphenyl-4-yl)dimethyl(1H-1,2,4-triazol-1-ylmethyl)silane A solution of 1.0 g (0.0034 mol) of (1,1'-biphenyl-4-yl)dimethyl(1H-1,2,4-triazol-1-ylmethyl)silane in 10 ml of dichloromethane was combined with a solution of 1.1 g (0.0034 mol) of 4-dodecylbenzenesulfonic acid in 10 ml of dichloromethane. The resulting solution was evaporated to leave the title salt as a viscous yellow oil: $n_D^{20}$ 1.5645; ir (neat) 3110, 3050, 3020, 2960, 2920, 2850, 2570, 1920, 1600, 1545, 1485, 1455, 1405, 1250, 1225, 1165, 1120, 1030, 1010, 990, 845, 825, 755, 735, 700, 670, 635 $cm^{-1}$.

EXAMPLE 35

Preparation of the 2:1 complex of [bis(4-Fluorophenyl)]methyl(1H-1,2,4-triazol-1-ylmethyl)silane and Curpic Chloride A mixture of 1.0 g (0.0032 mol) of [bis(4-fluorophenyl)]methyl(1H-1,2,4-triazol-1-ylmethyl)silane and 0.2 g (0.0016 mol) of cupric chloride in 30 ml of tetrahydrofuran was refluxed under $N_2$ for 30 minutes and evaporated to leave the title complex as a bluegreen glass: no distinct m.p.; ir (Nujol ®) 1580, 1490, 1230, 1160, 1110, 830, 785 $cm^{-1}$.

The 1:1 complex with cuprous chloride was prepared similarly to give a dark green glass: no distinct m.p.; ir as above.

By applying the procedures of Examples 33–35, any of the compounds of Tables VI, VII, VIII, IX, XI or XII can be converted to salts or metal complexes.

EXAMPLE 36

Preparation of (1,1-'Biphenyl-4-yl)(1H-1,2,4-triazol-1-ylmethyl)(methoxy)methylsilane A mixture of (1,1'-biphenyl-4-yl)chlorochloromethylmethylsilane and two equivalents of 1,2,4-triazole sodium salt in dimethylformamide is warmed to 80°–90° C. for 2 hours. Ten equivalents of methanol is then added, and the mixture is held at 70° C. for 1 hour, cooled, diluted with water, and quickly extracted with ether. Washing the ether solution with water and brine, drying over magnesium sulfate, and evaporation leaves the title compound.

Related compounds can be made in the same way, using the appropriate chlorosilane and alcohol; for $R_6$=OH, water is used instead of an alcohol, and hydrolysis, is conducted at 20°–25° C. instead of 70°.

EXAMPLE 37

Preparation of (1,1-dimethylethoxy)methyl(phenyl)(1H-1,2,4-triazol-1-ylmethyl)silane A mixture of 3.6 g (0.015 mol) of chloromethyl(1,1-dimethylethoxy)methyl(phenyl)silane and 1.3 g (0.015 mol) of 1,2,4-triazole sodium salt in 8 ml of dimethylformamide was stirred at 80° for 2 hours, cooled, and poured onto water. The resulting mixture was extracted with ether, and the ether extracts were washed with water and brine, dried over magnesium sulfate, and evaporated to leave 2.7 g of a yellow oil. Chromatography on silica gel, eluting with 50:50 ethyl acetate-hexanes, provided 1.5 g (36%) of the title compound as a pale yellow oil: $n_D^{21}$ 1.5134; ir (neat) 3120, 3070, 3045, 2975, 2925, 1500, 1425, 1380, 1365, 1270, 1255, 1240, 1190, 1140, 1115, 1050, 1020, 1010, 830, 810, 790, 740, 700, 680 $cm^{-1}$; nmr ($CDCl_3$): 0.6 (3H, s), 1.3 (9H, s), 3.9 (2H, s), 7.3–7.7 (5H, m), 7.9 (1H, s) and 8.0 (1H, s).

EXAMPLE 38

Preparation of bis(4-Fluorophenyl)hydroxy(1H-1,2,4-triazol-1-ylmethyl)silane

A mixture of 10.0 g (30.6 mmol) of chloromethyl[-bis(4-fluorophenyl)](2-propoxy)silane and 3.1 g (30.6 mmol) of 1,2,4-triazole sodium salt in dimethylformamide was stirred at 80°–90° under nitrogen for 2 hours. Workup as in Example 37 gave a waxy solid that was washed with 1:1 ether-hexanes to leave 3.0 g (30%) of the title compound. Recrystallization from chlorobutane gave a purer sample: m.p. 130°–131°; nmr ($CDCl_3$) 4.1 (2H, s), 5.8 (1H, broad s), 7.1 (4H, t), 7.7 (4H, d of d), 7.8 (1H, s), 8.0 (1H, s).

Alternatively, the silanol can be made by reacting a chloromethylchlorosilane with two equivalents of a triazole salt followed by hydrolysis, as illustrated by the following procedure. A solution of 6.1 g (20 mmol) of chloro(chloromethyl)[bis(4-fluorophenyl)]silane in 20 ml of dimethylformamide was cooled in ice under nitrogen and stirred while solid 1,2,4-triazole potassium salt was added in portions over 20 minutes. The resulting solution was stirred overnight at room temperature, then diluted with ether, washed with water and brine, dried over magnesium sulfate, and evaporated to leave 6 g of a colorless semisolid. Thin layer chromatography and nmr analysis showed that this crude product was a mixture of the title silanol and the corresponding disiloxane oxybis[bis(4-fluorophenyl)(1H-1,2,4-triazol-1-ylmethyl)silane]. This crude product was then dissolved in a mixture of 100 ml of tetrahydrofuran, 20 ml of water and 10 ml of concentrated hydrochloric acid. The resulting solution was stirred under nitrogen at room temperature for 22 hours, diluted with ether, washed with aqueous sodium bicarbonate, water, and brine, dried over magnesium sulfate, and evaporated to leave a colorless solid. Washing the solid with hexanes left behind 3.8 g (59%) of the title compound as a colorless powder: m.p. 126°–131°; nmr ($CDCl_3$) as above.

Another method for making the title compound is to subject a silyl ether such as 1,1-dimethylethoxy[bis(4-fluorophenyl)(1H-1,2,4-triazol-1-ylmethyl)silane] to acid-catalyzed hydrolysis.

EXAMPLE 39

Preparation of bis(4-Chlorophenyl)hydroxy(1H-1,2,4-triazol-1-ylmethyl)silane and bis(4-Chlorophenyl)hydroxy(4H-1,2,4-triazol-4-ylmethyl)silane The procedure of Example 38 was applied to chloromethyl[bis(4-chlorophenyl)](2-propoxy)silane. Workup gave an oil, which was swirled with hexanes. The hexanes layer was then decanted, and the residual oil was crystallized from 9:1 hexanes-ethyl acetate to give the 1H isomer as a solid: m.p. 130°–131°; nmr ($CDCl_3$) 4.1 (2H, s), 6.3 (1H, broad s), 7.4 (4H, d), 7.6 (4H, d), 7.8 (1H, s), 8.0 (1H, s).

Chromatography of the mother liquors over silica gel, eluting first with hexanes and then with 9:1 dichloromethane-acetone, provided the 4H isomer as a solid: m.p. 98°–103°; nmr ($CDCl_3$) 1.7 (1H, broad s), 4.2 (2H, s), 7.3 (8H, s), 7.8 (2H, s).

EXAMPLE 40

Preparation of (1,1'-Biphenyl-4-yl)hydroxy(methyl)(1H-1,2,4-triazol-1-ylmethyl)silane A mixture of 3.0 g (8.9 mmol) of (1,1'-biphenyl-4-yl)methyl(2-propoxy)(1H-1,2,4-triazol-1-ylmethyl)silane, 3 ml of concentrated hydrochloric acid, 10 ml of water, and 10 ml of tetrahydrofuran was stirred at room temperature overnight. The resulting solution was diluted with ether, washed with saturated aqueous sodium bicarbonate, water, and brine, dried over magnesium sulfate, and evaporated to leave 2.3 g of viscous oil. Chromatography over silica gel, eluting with hexane followed by ether, provided 1.1 g (42%) of the title compound as a viscous oil that solidified on standing: m.p. 97°–99°; nmr ($CDCl_3$) 0.5 (3H, s), 3.9 (2H, s), 5.2 (1H, broad s), 7.3–7.8 (9H, m), 7.9 (1H, s), 8.0 (1H, s).

The compounds of Tables VIII and IX can be made using the procedures of Examples 36–40.

Preparation of disiloxanes is illustrated by Examples 41 and 42.

EXAMPLE 41

Preparation of Oxybis[bis(4-fluorophenyl)(1H-1,2,4-triazol-1-ylmethyl)silane]

A solution of 11.0 g (33.7 mmol) of chloromethyl[-bis(4-fluorophenyl)](2-propoxy)silane and 10 ml of 49% aqueous hydrofluoric acid in ethanol was refluxed for 2 hours under nitrogen, cooled, and partitioned between water and ether. The organic layer was washed with water and brine, dried over magnesium sulfate, and evaporated to leave 9.7 g (100%) of chloromethyl(-fluoro)[bis(4-fluorophenyl)]silane as a mobile oil: $n_D^{22}$ 1.5387; nmr ($CDCl_3$) 3.2 (2H, d), 7.2 (4H, t), 7.8 (4H, d of d).

A mixture of 4.5 g (16 mmol) of the fluorosilane prepared above and 1.6 g (18 mmol) of 1,2,4-triazole sodium salt in dimethylformamide was stirred at 80°–90° for 2 hours. The resulting slurry was diluted with ether, washed three times with water and once with brine, dried over magnesium sulfate, and evaporated to leave a viscous oil. Trituration with 1:1 etherhexanes gave 1.1 g (23%) of the title disiloxane as a colorless solid: m.p.

165°–168°; nmr ($CDCl_3$) 4.1 (2H, s), 7.0 (4H, t), 7.4 (4H, d of d), 7.8 (1H, s), 7.9 (1H, s).

EXAMPLE 42

Preparation of Oxybis[bis(4-chlorophenyl)(1H-1,2,4-triazol-1-ylmethyl)silane]

The procedure of Example 39 was repeated except that two equivalents of 1,2,4-triazole were used for each equivalent of chloromethylsilane. Work-up as in Example 38 provided a colorless solid that was recrystallized from 1-chlorobutane to give the title disiloxane as colorless prisms, m.p. 145°–147°; nmr ($CDCl_3$) 4.2 (2H, s), 7.3 (8H, s), 7.8 (1H, s), 7.9 (1H, s).

TABLE VIII

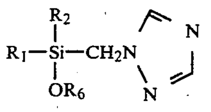

| $R_1$ | $R_2$ | $R_6$ | |
|---|---|---|---|
| $C_2H_5$ | $CH_3$ | $CH_3$ | |
| t-$C_4H_9$ | $CH_3$ | t-$C_4H_9$ | |
| n-$C_4H_9$ | $CH_3$ | $C_2H_5$ | |
| n-$C_{12}H_{25}$ | $C_2H_5$ | $CH_3$ | |
| n-$C_{18}H_{37}$ | n-$C_6H_{13}$ | $CH_3$ | |
| cyclopropyl | $CH_3$ | s-$C_4H_9$ | |
| cyclohexyl | $CH_3$ | $CH_3$ | |
| 1-naphthyl | i-$C_3H_7$ | i-$C_3H_7$ | |
| 2-naphthyl | cyclobutyl | n-$C_3H_7$ | |
| phenyl | $CH_3$ | H | |
| phenyl | $CH_3$ | $CH_3$ | |
| phenyl | $CH_3$ | $C_2H_5$ | |
| phenyl | $CH_3$ | i-$C_3H_7$ | $n_D^{20}$ 1.5367 |
| phenyl | t-$C_4H_9$ | H | |
| 4-phenylphenyl | n-$C_4H_9$ | $CH_3$ | |
| 4-phenylphenyl | t-$C_4H_9$ | H | |
| 4-phenylphenyl | $CH_3$ | $C_2H_5$ | |
| 4-phenylphenyl | $CH_3$ | i-$C_3H_7$ | $n_D^{22}$ 1.5959 |
| 4-phenylphenyl | $CH_3$ | n-$C_4H_9$ | |
| 4-chlorophenyl | n-$C_4H_9$ | n-$C_4H_9$ | |
| 4-chlorophenyl | $CH_3$ | $CH_3$ | |
| 4-chlorophenyl | $CH_3$ | $C_2H_5$ | |
| 4-fluorophenyl | n-$C_6H_{13}$ | n-$C_3H_7$ | |
| 4-fluorophenyl | $CH_3$ | $C_2H_5$ | |
| 4-fluorophenyl | $CH_3$ | i-$C_3H_7$ | $n_D^{22}$ 1.5110 |
| 4-phenoxyphenyl | cyclohexyl | i-$C_4H_9$ | |
| 4-t-butylphenyl | n-$C_3H_7$ | s-$C_4H_9$ | |
| 3-trifluoromethyl-phenyl | t-$C_4H_9$ | H | |
| 2-methylthiophenyl | cyclopentyl | $C_2H_5$ | |
| 2,4-dichlorophenyl | $CH_3$ | $CH_3$ | |
| 2,4-dichlorophenyl | $CH_3$ | $C_2H_5$ | |
| 2,4-dichlorophenyl | $CH_3$ | t-$C_4H_9$ | |
| 2,4-dichlorophenyl | n-$C_4H_9$ | $C_2H_5$ | |
| 2,3-dimethylphenyl | cyclopropyl | i-$C_3H_7$ | |
| 2-methyl-5-fluoro-phenyl | s-$C_4H_9$ | n-$C_3H_7$ | |
| 2,6-dimethoxyphenyl | 1,1-dimethylpropyl | H | |
| 3-methyl-4-chloro-phenyl | $C_2H_5$ | $CH_3$ | |
| 3,5-dichlorophenyl | n-$C_5H_{11}$ | $C_2H_5$ | |
| n-$C_{12}H_{25}$ | 2,4-dichlorophenyl | t-$C_4H_9$ | |
| n-$C_{18}H_{37}$ | phenyl | $CH_3$ | |
| 1-naphthyl | phenyl | $C_2H_5$ | |
| phenyl | phenyl | t-$C_4H_9$ | |
| 4-fluorophenyl | phenyl | $CH_3$ | |
| 4-chlorophenyl | phenyl | n-$C_3H_7$ | |
| 4-phenylphenyl | phenyl | $C_2H_5$ | |
| 4-phenylphenyl | phenyl | s-$C_4H_9$ | |
| 4-t-butylphenyl | phenyl | s-$C_4H_9$ | |
| 3-fluorophenyl | phenyl | $C_2H_5$ | |
| 2-methoxyphenyl | phenyl | H | |
| 2-chlorophenyl | phenyl | $CH_3$ | |
| 2,4-dichlorophenyl | phenyl | i-$C_3H_7$ | |
| 3,5-dichlorophenyl | phenyl | n-$C_3H_7$ | |
| 4-fluorophenyl | 4-fluorophenyl | t-$C_4H_9$ | $n_D^{22}$ 1.5375 |
| 4-fluorophenyl | 4-fluorophenyl | $C_2H_5$ | |

TABLE VIII-continued

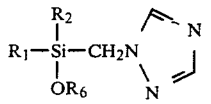

| $R_1$ | $R_2$ | $R_6$ |
|---|---|---|
| 4-chlorophenyl | 4-chlorophenyl | $CH_3$ |
| 4-chlorophenyl | 4-chlorophenyl | $C_2H_5$ |
| 4-phenylphenyl | 4-phenylphenyl | $CH_3$ |
| 2,4-dichlorophenyl | 2,4-dichlorophenyl | $C_2H_5$ |
| 3-trifluoromethyl-phenyl | 3-trifluoromethyl-phenyl | i-$C_4H_9$ |
| 2-methoxyphenyl | 2-methoxyphenyl | H |
| 2-chlorophenyl | 4-fluorophenyl | H |
| 3-trifluoromethyl-phenyl | 4-t-butylphenyl | n-$C_4H_9$ |
| 2-fluoro-4-chloro-phenyl | 4-bromophenyl | i-$C_3H_7$ |
| 2,3-dimethylphenyl | 4-methylthiophenyl | $C_2H_5$ |
| 2,6-dimethoxyphenyl | 4-methoxyphenyl | H |
| 3,4-dichlorophenyl | 4-methylphenyl | i-$C_4H_9$ |

TABLE IX

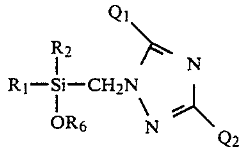

| $R_1$ | $R_2$ | $R_6$ | $Q_1$ | $Q_2$ |
|---|---|---|---|---|
| $C_2H_5$ | $CH_3$ | $CH_3$ | $CH_3$ | $CH_3$ |
| cyclohexyl | $CH_3$ | i-$C_3H_7$ | H | $CH_3$ |
| n-$C_{18}H_{37}$ | n-$C_6H_{13}$ | t-$C_4H_9$ | $CH_3$ | $CH_3$ |
| 1-naphthyl | $CH_3$ | i-$C_3H_7$ | $CH_3$ | $CH_3$ |
| phenyl | $CH_3$ | t-$C_4H_9$ | H | $CH_3$ |
| phenyl | $CH_3$ | t-$C_4H_9$ | $CH_3$ | H |
| phenyl | $CH_3$ | t-$C_4H_9$ | $CH_3$ | $CH_3$ |
| phenyl | $CH_3$ | s-$C_4H_9$ | H | $CH_3$ |
| phenyl | $CH_3$ | i-$C_4H_9$ | H | $CH_3$ |
| 4-phenylphenyl | n-$C_4H_9$ | t-$C_4H_9$ | H | $CH_3$ |
| 4-phenylphenyl | $CH_3$ | t-$C_4H_9$ | H | $CH_3$ |
| 4-phenylphenyl | $CH_3$ | t-$C_4H_9$ | $CH_3$ | $CH_3$ |
| 4-chlorophenyl | $CH_3$ | t-$C_4H_9$ | H | $CH_3$ |
| 4-chlorophenyl | $CH_3$ | t-$C_4H_9$ | $CH_3$ | $CH_3$ |
| 4-fluorophenyl | $CH_3$ | t-$C_4H_9$ | H | $CH_3$ |
| 4-fluorophenyl | $CH_3$ | t-$C_4H_9$ | $CH_3$ | $CH_3$ |
| phenyl | phenyl | $C_2H_5$ | $CH_3$ | $CH_3$ |
| phenyl | phenyl | n-$C_3H_7$ | $CH_3$ | $CH_3$ |
| 4-fluorophenyl | phenyl | i-$C_3H_7$ | H | $CH_3$ |
| 4-fluorophenyl | phenyl | t-$C_4H_9$ | $CH_3$ | $CH_3$ |
| 4-chlorophenyl | phenyl | i-$C_3H_7$ | H | $CH_3$ |
| 2,4-dichlorophenyl | phenyl | H | $CH_3$ | $CH_3$ |
| 4-fluorophenyl | 4-fluorophenyl | t-$C_4H_9$ | H | $CH_3$ |
| 4-fluorophenyl | 4-fluorophenyl | t-$C_4H_9$ | $CH_3$ | H |
| 4-fluorophenyl | 4-fluorophenyl | t-$C_4H_9$ | $CH_3$ | $CH_3$ |
| 2-methoxyphenyl | 2-methoxyphenyl | $C_2H_5$ | $CH_3$ | $CH_3$ |
| 3-methylphenyl | 3-methylphenyl | i-$C_4H_9$ | H | $CH_3$ |

EXAMPLE 43

Preparation of Chloromethyl(dichloro)phenylsilane

A solution of 25.1 ml (36.8 g, 0.200 mol) of chloromethyltrichlorosilane in 400 ml dry tetrahydrofuran was cooled to −78° under nitrogen and stirred vigorously while 48.0 ml (0.100 mol) of 2.1 molar phenyllithium was slowly dripped in over 1 hour. After stirring another 30 minutes at −78° the solution was allowed to warm to room temperature and evaporated to about 200 ml. Addition of 500 ml ether, filtration to remove precipitated lithium chloride, and evaporation of the filtrate left 25.0 g of liquid. Distillation gave 6.5 g (29%)

of the title compound as a colorless liquid: bp 62°-82° (0.15 mm); nmr ($CDCl_3$): δ3.3 (s, 2) and 7.1-7.9 (m, 5).

EXAMPLE 44

Preparation of Chloromethyl(diethoxy)phenylsilane

A solution of 1.0 g (0.0044 mol) of chloromethyl(dichloro)phenylsilane in 8 ml of absolute ethanol was cooled to 0° under nitrogen and stirred while 0.61 ml (0.445 g, 0.0044 mol) of triethylamine was slowly added, giving a slurry that was allowed to warm to room temperature. Addition of 50 ml of ether, filtration to remove precipitated triethylamine/hydrochloride, and evaporation of the filtrate left a residue which was filtered through a short silica gel column (95% petroleum ether:ethyl acetate as the eluent) to give 0.80 (73%) of the title compound as a colorless oil: nmr ($CDCl_3$): δ1.25 (t, 6, J=6 Hz), 3.0 (s, 2), 3.9 (q, 4, J=6 Hz) and 7.2-7.9 (m, 5).

EXAMPLE 45

Preparation of Chloromethyl(phenyl)bis(2-propoxy)silane

A solution of 2.0 g (0.009 mol) of chloromethyl(dichloro)phenylsilane and 5 ml of 2-propanol in 15 ml of dimethylformamide was stirred under $N_2$ while 2.5 ml (1.9 g, 0.018 mol) of triethylamine was added dropwise. The resulting slurry was warmed to 80° for 2 hours, cooled, diluted with water, and extracted with ether. The ether extracts were washed with water and brine, dried over magnesium sulfate, and evaporated to leave 2.2 g of liquid. Column chromatography over silica gel, eluting with petroleum ether, provided 1.4 g (58%) of the title compound as a colorless liquid: $n_D^{22}$ 1.4741; nmr ($CDCl_3$) 1.2 (12H, d, J=6), 3.0 (2H, s), 4.3 (2H, septet, J=6), 7.3-7.8 (5H, m).

EXAMPLE 46

Preparation of (1,1'-Biphenyl-4-yl)chloromethyl(diethoxy)silane

A mixture of 6.3 g (0.257 mol) of magnesium turnings and about 0.2 g of iodine in 30 ml of tetrahydrofuran was stirred under nitrogen while 25 ml of a solution of 60.0 g (0.257 mol) of 4-bromobiphenyl in 75 ml of tetrahydrofuran was added dropwise. When the iodine color disappeared, another 150 ml of tetrahydrofuran was added to the reaction followed by the dropwise addition of the remaining 4-bromobiphenyl solution at a rate that maintained a gentle reflux. The resulting solution was allowed to cool to room temperature and then added to a stirred solution of 35.5 ml (51.9 g, 0.282 mol) of chloromethyltrichlorosilane in 100 ml of tetrahydrofuran which had been cooled to −70° under nitrogen. The resulting solution was allowed to warm to room temperature and then cooled with an ice bath while 125 ml of ethyl alcohol was added followed by the dropwise addition of 84 ml (60.6 g, 0.600 mol) of triethylamine. The resulting slurry was stirred while warming to room temperature, allowed to stand overnight, diluted with water, and extracted with ether. The ether solution was washed with brine, dried over magnesium sulfate, evaporated, and distilled to provide 37.6 g (46%) of the title compound as a clear liquid: b.p. 165°-185° (0.05 mm); $n_D^{22}$ 1.5593; ir (neat) 2950, 1605, 1490, 1450, 1395, 1170 $cm^{-1}$; nmr ($CDCl_3$) 1.25 (6H, t, J=7), 2.95 (2H, s), 3.9 (4H, q, J=7) and 7.3-7.9 (9H, m).

The compounds of Table X can be made using the procedures of Examples 43-46.

It is sometimes advantageous to convert a chloromethylsilane to the corresponding iodomethylsilane prior to reaction with a triazole. This procedure is illustrated by Example 47.

EXAMPLE 47

Preparation of Diethoxy(iodomethyl)phenylsilane

A mixture of 12.8 g (0.052 mol) of chloromethyl(diethoxy)phenylsilane, 9.4 g (0.062 mol) of sodium iodide and 0.21 g (0.52 mol) of tricaprylylmethylammonium chloride (Aliquat®336) in 10 of ethyl alcohol was refluxed for 12 hours, cooled, filtered, and evaporated. The filtrate was diluted with water and extracted with ether. The ether solution was washed with brine, dried over magnesium sulfate, evaporated, and distilled to provide 8.7 g (50%) of the title compound as a clear liquid: b.p. 86°-100° (0.15 mm); $n_D^{19}$ 1.5204; ir (neat) 2980, 1590, 1480, 1430, 1390, 1290, 1165 $cm^{-1}$; nmr ($CDCl_3$) 1.25 (6H, t, J=7), 2.15 (2H, s), 3.85 (3H, q, J=7) and 7.3-7.9 (5H, m).

Any of the compounds of Table X may be converted to iodomethylsilanes using this procedure. Further examples include:

(1,1'-Biphenyl-4-yl)diethoxy(iodomethyl)silane: b.p. 190° (0.1 mm), $n_D^{21}$ 1.5861;

(4-Chlorophenyl)diethoxy(iodomethyl)silane: b.p. 90°-105° (0.05 mm), $n_D^{21}$ 1.5378; and Diethoxy(4-fluorophenyl)iodomethylsilane: b.p. 85°-87° (0.075 mm), $n_D^{21}$ 1.5169.

TABLE X

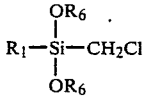

| $R_1$ | $R_6$ | |
|---|---|---|
| $C_2H_5$ | t-$C_4H_9$ | |
| n-$C_4H_9$ | $C_2H_5$ | |
| n-$C_{18}H_{37}$ | $CH_3$ | |
| cyclohexyl | n-$C_3H_7$ | |
| 1-naphthyl | i-$C_4H_9$ | |
| phenyl | $CH_3$ | |
| phenyl | n-$C_3H_7$ | |
| phenyl | t-$C_4H_9$ | |
| 4-phenylphenyl | n-$C_4H_9$ | |
| 4-phenoxyphenyl | $C_2H_5$ | |
| 4-fluorophenyl | $CH_3$ | |
| 4-fluorophenyl | $C_2H_5$ | $n_D^{22}$ 1.4768 |
| 4-chlorophenyl | $C_2H_5$ | $n_D^{22}$ 1.4979 |
| 4-chlorophenyl | i-$C_3H_7$ | |
| 3-trifluoromethylphenyl | s-$C_4H_9$ | |
| 2-methoxyphenyl | n-$C_3H_7$ | |
| 2,3-dimethylphenyl | i-$C_4H_9$ | |
| 2,4-dichlorophenyl | $CH_3$ | |
| 2,4-dichlorophenyl | $C_2H_5$ | |
| 2-methoxy-5-fluorophenyl | i-$C_3H_7$ | |
| 2,6-dimethoxyphenyl | $CH_3$ | |
| 3,4-dichlorophenyl | $C_2H_5$ | |
| 3,5-dichlorophenyl | n-$C_4H_9$ | |

EXAMPLE 48

Preparation of Phenylbis(2-propoxy)(1H-1,2,4-triazol-1-ylmethyl)silane

The title compound can be made by applying the procedure of Example 37 to chloromethyl(phenyl)bis(2- propoxy)silane: $n_D^{22}$ 1.4962; nmr ($CDCl_3$) 1.1 (12H, d, J=6), 4.0 (2H, s), 4.3 (2H, septet, J=6), 7.2–8.0 (7H, m).

EXAMPLE 49

Preparation of Diethoxy(phenyl)(1H-1,2,4-triazol-1-ylmethyl)silane

A mixture of 4.0 g (0.012 mol) of diethoxy(iodomethyl)phenylsilane, 1.5 g (0.014 mol) of 1,2,4-triazole potassium salt, and 0.5 g (0.14 mmol) of tetrabutylammonium hydrogen sulfate in 10 ml of toluene was stirred and warmed to 100°–110° C. for 5 hours, cooled, diluted with water, and extracted with methylene chloride. The methylene chloride solution was washed with brine, dried over magnesium sulfate, and evaporated to leave 2.6 g (79%) of the title compound as a pale brown oil: $n_D^{19}$ 1.5543; ir (neat) 2980, 1590, 1505, 1430, 1270 $cm^{-1}$; nmr ($CDCl_3$) 1.2 (6H, t, J=7), 3.8 (4H, q, J=7), 3.9 (2H, s), 7.2–7.7 (5H, m), 7.8 (s, 1H) and 8.0 (s, 1H).

EXAMPLE 50

Preparation of 2-Phenyl-4,6-dimethyl-2-(1H-1,2,4-triazol-1-ylmethyl)-2-sila-1,3-dioxane A mixture of 2.8 g (0.010 mol) of diethoxy(phenyl)(1H-1,2,4-triazol-1-ylmethyl)silane, 1.05 g (0.010 mol) of 2,4-pentanediol, and 0.1 g (0.5 mol) of p-toluenesulfonic acid monohydrate was heated to 100°–160° at atmospheric pressure until no further ethyl alcohol distilled. Further distillation at reduced pressure provided 0.70 g (24%) of the title compound as a pale yellow liquid: b.p. 147°–150° (0.1 mm); $n_D^{20}$ 1.5096; ir (neat) 2980, 1595, 1505, 1430, 1380, 1275 $cm^{-1}$; nmr ($CDCl_3$) 0.9–2.0 (8H, m), 4.0 (2H, s), 4.0–4.4 (2H, m), 7.1–7.8 (5H, m), 7.9 (1H, m) and 8.1 (1H, m).

The compounds of Tables XI and XII can be made using the procedures of Examples 48–50.

TABLE XI

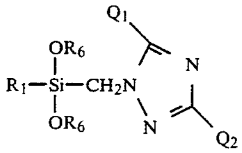

| $R_1$ | $R_6$ | $Q_1$ | $Q_2$ | |
|---|---|---|---|---|
| $C_2H_5$ | t-$C_4H_9$ | $CH_3$ | $CH_3$ | |
| n-$C_4H_9$ | $C_2H_5$ | H | $CH_3$ | |
| n-$C_{18}H_{37}$ | $CH_3$ | H | H | |
| n-$C_{18}H_{37}$ | $C_2H_5$ | H | $CH_3$ | |
| cyclohexyl | n-$C_3H_7$ | H | $CH_3$ | |
| l-naphthyl | i-$C_4H_9$ | $CH_3$ | H | |
| phenyl | $CH_3$ | $CH_3$ | $CH_3$ | |
| phenyl | n-$C_3H_7$ | H | $CH_3$ | |
| phenyl | i-$C_3H_7$ | $CH_3$ | $CH_3$ | |
| phenyl | 5-$C_4H_9$ | H | H | |
| 4-phenylphenyl | $C_2H_5$ | $CH_3$ | $CH_3$ | |
| 4-phenylphenyl | $C_2H_5$ | H | H | $n_D^{21}$ 1.5788 |
| 4-phenylphenyl | n-$C_4H_9$ | H | H | |
| 4-phenoxyphenyl | $C_2H_5$ | $CH_3$ | $CH_3$ | |
| 4-fluorophenyl | $CH_3$ | H | H | |
| 4-fluorophenyl | $C_2H_5$ | H | H | $n_D^{22}$ 1.5322 |
| 4-chlorophenyl | $C_2H_5$ | H | H | $n_D^{20}$ 1.5413 |
| 4-chlorophenyl | i-$C_3H_7$ | H | H | |
| 3-trifluoromethylphenyl | 2-$C_4H_9$ | $CH_3$ | $CH_3$ | |
| 2-methoxyphenyl | n-$C_3H_7$ | H | $CH_3$ | |
| 2,3-dimethylphenyl | i-$C_4H_9$ | $CH_3$ | $CH_3$ | |
| 2,4-dichlorophenyl | $CH_3$ | H | H | |
| 2,4-dichlorophenyl | $C_2H_5$ | H | H | |
| 2-methoxy-5-fluorophenyl | i-$C_3H_7$ | H | H | |
| 2,6-dimethoxyphenyl | $CH_3$ | H | H | |
| 3,4-dichlorophenyl | $C_2H_5$ | H | H | |
| 3,5-dichlorophenyl | n-$C_4H_9$ | H | H | |

TABLE XII

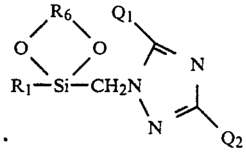

| $R_1$ | $R_6$ | $Q_1$ | $Q_2$ |
|---|---|---|---|
| $C_2H_5$ | $-CH_2CH_2-$ | $CH_3$ | $CH_3$ |
| n-$C_4H_9$ | $CH_3$<br>$-CH_2CH-$ | H | $CH_3$ |
| n-$C_{18}H_{37}$ | $-CH_2CH_2CH_2-$ | H | H |
| cyclohexyl | $C_2H_5$<br>$-CH_2CH-$ | H | $CH_3$ |
| 1-naphthyl | $-CH_2CH_2-$ | $CH_3$ | H |
| phenyl | $-CH_2CH_2-$ | $CH_3$ | $CH_3$ |
| phenyl | $C_2H_5$<br>$-CH_2CH-$ | H | H |
| phenyl | n-$C_3H_7$<br>$-CH_2CH-$ | H | H |
| phenyl | $-C(CH_3)_2C(CH_3)_2-$ | H | H |
| phenyl | $CH_3$<br>$-CH_2CH_2CH-$ . | H | H |

TABLE XII-continued

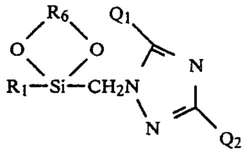

| $R_1$ | $R_6$ | $Q_1$ | $Q_2$ | |
|---|---|---|---|---|
| phenyl | $-CH_2CH_2CH_2-$ | H | H | |
| 4-phenylphenyl | $-CH_2CH_2-$ | H | H | |
| 4-phenylphenyl | $C_2H_5$<br>\|<br>$-CH_2CH-$ | H | H | |
| 4-phenylphenyl | $CH_3$ $CH_3$<br>\| \|<br>$-CH-CH-$ | H | H | |
| 4-phenylphenyl | $CH_3$ $CH_3$<br>\| \|<br>$-CHCH_2CH-$ | H | H | $n_D^{21}$ 1.5544 |
| 4-phenylphenyl | $CH_3$<br>\|<br>$-CH_2CH_2CH-$ | H | H | |
| 4-phenylphenyl | $-CH_2CH_2CH_2-$ | H | H | |
| 4-fluorophenyl | $-CH_2CH_2-$ | H | H | |
| 4-fluorophenyl | $CH_3$<br>\|<br>$-CH_2CH-$ | H | H | |
| 4-fluorophenyl | $CH_3$ $CH_3$<br>\| \|<br>$-CHCH_2CH-$ | H | H | $n_D^{22}$ 1.5037 |
| 4-fluorophenyl | $CH_3$<br>\|<br>$-CH_2CH_2CH-$ | H | H | |
| 4-fluorophenyl | $-CH_2CH_2CH_2-$ | H | H | |
| 4-chlorophenyl | $C_2H_5$<br>\|<br>$-CH_2CH-$ | H | H | |
| 4-chlorophenyl | $-C(CH_3)_2C(CH_3)_2-$ | H | H | |
| 4-chlorophenyl | $CH_3$ $CH_3$<br>\| \|<br>$-CHCH_2CH-$ | H | H | $n_D^{20}$ 1.5264 |
| 4-chlorophenyl | $CH_3$<br>\|<br>$-CH_2CH_2CH-$ | H | H | $n_D^{20}$ 1.5304 |
| 4-chlorophenyl | $-CH_2CH_2CH_2-$ | H | H | |
| 3-trifluoromethylphenyl | $CH_3$<br>\|<br>$-CHCH_2C(CH_3)_2-$ | $CH_3$ | $CH_3$ | |
| 2-methoxyphenyl | n-$C_4H_9$<br>\|<br>$-CH_2CH-$ | H | $CH_3$ | |
| 2,3-dimethylphenyl | $-CH_2CH_2-$ | $CH_3$ | $CH_3$ | |
| 2,4-dichlorophenyl | $C_2H_5$<br>\|<br>$-CH_2CH-$ | H | H | |
| 2,4-dichlorophenyl | n-$C_3H_7$<br>\|<br>$-CH_2CH-$ | H | H | |
| 2-methoxy-5-fluorophenyl | $CH_3$ $CH_3$<br>\| \|<br>$-CHC(CH_3)_2CH-$ | H | H | |

TABLE XII-continued

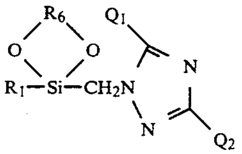

| R1 | R6 | Q1 | Q2 |
|---|---|---|---|
| 2,6-dimethoxyphenyl | $-CH_2CH_2-$ | H | H |
| 3,4-dichlorophenyl | 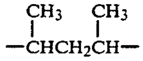 | H | H |
| 3,5-dichlorophenyl | 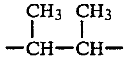 | H | H |
| $C_2H_5$ | $-CH_2CH=CHCH_2-$ | $CH_3$ | $CH_3$ |
| n-$C_{18}H_{37}$ | 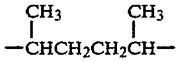 | H | $CH_3$ |
| phenyl | $-CH_2CH=CHCH_2-$ | H | H |
| phenyl | $-C(CH_3)_2CH=CHC(CH_3)_2-$ | H | H |
| phenyl | 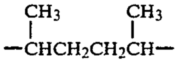 | H | H |
| phenyl | $-C(CH_3)_2CH_2CH_2C(CH_3)_2-$ | H | H |
| 4-phenylphenyl | $-CH_2CH=CHCH_2-$ | H | H |
| 4-phenylphenyl | 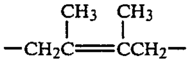 | H | H |
| 4-fluorophenyl | $-CH_2-CH=CHCH_2-$ | H | H |
| 4-chlorophenyl | $-CH_2CH_2CH_2CH_2-$ | H | H |
| 4-phenoxyphenyl | 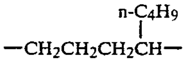 | $CH_3$ | $CH_3$ |
| 3-trifluoromethylphenyl | 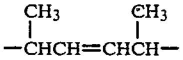 | $CH_3$ | $CH_3$ |
| 2-methoxyphenyl | 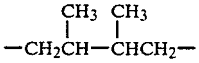 | H | $CH_3$ |

Formulations

Useful formulations of the compounds within the scope of this invention can be prepared in conventional ways. They include dusts, granules, pellets, solutions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulations. The formulations, broadly, contain about 1% to 99% by weight of active ingredient(s) and at least one of (a) about 0.1% to 20% surfactant(s) and (b) about 5% to 99% solid or liquid inert diluent(s). More specifically, they will contain these ingredients in the following approximate proportions:

| | Active Ingredient | Percent by Weight | |
|---|---|---|---|
| | | Diluent(s) | Surfactant(s) |
| Wettable Powders | 20-90 | 0-74 | 1-10 |
| Oil Suspensions, Emulsions, Solutions, | 5-50 | 40-95 | 0-15 |

-continued

| | Active Ingredient | Percent by Weight | |
|---|---|---|---|
| | | Diluent(s) | Surfactant(s) |
| (including Emulsifiable Concentrates) | | | |
| Aqueous Suspensions | 10-50 | 40-84 | 1-20 |
| Dusts | 1-25 | 70-99 | 0-5 |
| Granules and Pellets | 1-95 | 5-99 | 0-15 |
| High Strength Compositions | 90-99 | 0-10 | 0-2 |

Lower or higher levels of active ingredients can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for the wettable powders and the denser ones for dusts. Typical liquid diluents and solvents are described in Marsden, "Solvents Guide," 2nd Ed., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Corp., Ridgewood, N.J., as well as Sisely and Wood, "Encyclopedia of Surface Active Agents", Chemical Publishing Co., Inc., New York, 1964, list surfactants and recommended uses. All formulations can contain minor amounts of additives to reduce foam, caking, corrosion, microbiological growth, etc.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", *Chemical Engineering*, Dec. 4, 1967, pp. 147ff. and "Perry's Chemical Engineer's Handbook", 4th Ed., McGraw-Hill, New York, 1963, pp. 8-59ff.

EXAMPLE 51

Wettable Powder

| | |
|---|---|
| (1,1-Biphenyl-4-yl)dimethyl(1H—1,2,4-triazol-1-yl-methyl)silane | 40% |
| dioctyl sodium sulfosuccinate | 1.5% |
| sodium ligninsulfonate | 3% |
| low viscosity methyl cellulose | 1.5% |
| attapulgite | 54% |

The ingredients are thoroughly blended, passed through an air mill, to produce an average particle size under 15 microns, reblended, and sifted through a U.S.S. No. 50 sieve (0.3 mm opening) before packaging.

All compounds of the invention may be formulated in the same manner.

EXAMPLE 52

Wettable Powder

| | |
|---|---|
| (4-Bromophenyl)dimethyl(1H—1,2,4-triazol-1-ylmethyl)-silane | 20% |
| sodium alkylnaphthalenesulfonate | 2% |
| low viscosity methyl cellulose | 2% |
| diatomaceous earth | 76% |

The ingredients are blended, coarsely hammer-milled and then air milled to produce particles of active essentially all below 10 microns in diameter. The product is reblended before packaging.

EXAMPLE 53

High Strength Concentrate

| | |
|---|---|
| (4-Chlorophenyl)dimethyl(1H—1,2,4-triazol-1-yl-methyl)silane | 98.5% |
| silica aerogel | 0.5% |
| synthetic amorphous fine silica | 1.0% |

The ingredients are blended and ground in a hammer-mill to produce a high strength concentrate essentially all passing a U.S.S. No. 50 sieve (0.3 mm openings). This material may then be formulated in a variety of ways.

EXAMPLE 54

Dust

| | |
|---|---|
| high strength concentrate from Example 53 | 25.4% |
| pyrophyllite, powdered | 74.6% |

The ingredients are thoroughly blended and packaged for use.

EXAMPLE 55

Aqueous Suspension

| | |
|---|---|
| (1,1'-Biphenyl-4-yl)dimethyl(1H—1,2,4-triazol-1-yl-methyl)silane | 50.0% |
| polyacrylic acid thickener | 0.3% |
| dodecylphenyl polyethylene glycol ether | 0.5% |
| disodium phosphate | 1.0% |
| monosodium phosphate | 0.5% |
| polyvinyl alcohol | 1.0% |
| pentachlorophenyl | 0.4% |
| water | 46.3% |

The ingredients are ground together in a sand mill to produce particles substantially all under five microns in size.

EXAMPLE 56

Emulsifiable Concentrate

| | |
|---|---|
| Dimethyl(phenyl) (1H—1,2,4-triazol-1-ylmethyl)-silane | 20% |
| chlorobenzene | 74% |
| sorbitan monostearate and poly-oxyethylene condensates thereof | 6% |

The ingredients are combined and stirred to produce a solution which can be emulsified in water for application.

EXAMPLE 57

Emulsifiable Concentrate

| | |
|---|---|
| Dimethyl(4-methylphenyl) (1H—1,2,4-triazol-1-ylmethyl)-silane | 30% |
| blend of oil soluble sulfonates and polyoxyethylene ethers | 4% |
| xylene | 66% |

The ingredients are combined and stirred with gentle warming to speed solution. A fine screen filter is included in packaging operation to insure the absence of any extraneous undissolved material in the product.

EXAMPLE 58

Granule

| | |
|---|---|
| wettable powder of example 51 | 15% |
| gypsum | 69% |
| potassium sulfate | 16% |

The ingredients are blended in a rotating mixer and water sprayed on to accomplish granulation. When most of the material has reached the desired range of 1.0 to 0.42 mm. (U.S.S. No. 18 to 40 sieves), the granules are removed, dried, and screened. Oversize material is crushed to produce additional material in the desired range. These granules contain active ingredient.

EXAMPLE 59

Emulsifiable Concentrate

| | |
|---|---|
| (2,4-Dichlorophenyl)dimethyl(1H—1,2,4-triazol-1-yl-methyl)silane | 30% |
| blend of oil soluble sulfonates and polyoxyethylene ethers | 4% |
| xylene | 66% |

The ingredients are combined and stirred with gentle warming to speed solution. A fine screen filter is included in packaging operation to insure the absence of any extraneous undissolved material in the product.

EXAMPLE 60

Emulsifiable Concentrate

| | |
|---|---|
| Butyl(4-chlorophenyl)methyl(1H—1,2,4-triazol-1-yl-methyl)silane | 30% |
| blend of oil soluble sulfonates and polyoxyethylene ethers | 4% |
| xylene | 66% |

The ingredients are combined and stirred with gentle warming to speed solution. A fine screen filter is included in packaging operation to insure the absence of any extraneous undissolved material in the product.

EXAMPLE 61

Emulsifiable Concentrate

| | |
|---|---|
| bis(4-Chlorophenyl)methyl(1H—1,2,4-triazol-1-ylmethyl)-silane | 30% |
| blend of oil soluble sulfonates and polyoxyethylene ethers | 4% |
| xylene | 66% |

The ingredients are combined and stirred with gentle warming to speed solution. A fine screen filter is included in packaging operation to insure the absence of any extraneous undissolved material in the product.

EXAMPLE 62

Emulsifiable Concentrate

| | |
|---|---|
| bis(4-Fluorophenyl)methyl(1H—1,2,4-triazol-1-ylmethyl)-silane | 20% |
| chlorobenzene | 74% |
| sorbitan monostearate and poly-oxyethylene condensates thereof | 6% |

The ingredients are combined and stirred to produce a solution which can be emulsified in water for application.

EXAMPLE 63

Emulsifiable Concentrate

| | |
|---|---|
| 4-Fluorophenyl(methyl)phenyl(1H—1,2,4-triazol-1-yl-methyl)silane | 30% |
| blend of oil soluble sulfonates and polyoxyethylene ethers | 4% |
| xylene | 66% |

The ingredients are combined and stirred with gentle warming to speed solution. A fine screen filter is included in packaging operation to insure the absence of any extraneous undissolved material in the product.

EXAMPLE 64

Emulsifiable Concentrate

| | |
|---|---|
| (1,1'-Biphenyl-4-yl)dimethyl(4H—1,2,4-triazol-4-yl-methyl)silane | 45% |
| cyclohexanone | 45% |
| sorbitan monostearate and polyoxy-ethylene condensates thereof | 10% |

The ingredients are combined and stirred to produce a solution which can be emulsified in water for application.

EXAMPLE 65

Emulsifiable Concentrate

| | |
|---|---|
| bis(4-Fluorophenyl)methyl(1H—1,2,4-triazol-1-yl-methyl)silane | 45% |
| blend of oil soluble sulfonates and polyoxyethylene ethers | 10% |
| cyclohexanone | 45% |

The ingredients are combined and stirred with gentle warming to speed solution. A fine screen filter is included in packaging operation to insure the absence of any extraneous undissolved material in the product.

EXAMPLE 66

Emulsifiable Concentrate

| | |
|---|---|
| 4-Fluorophenyl(methyl)phenyl(1H—1,2,4-triazol-1-yl-methyl)silane | 45% |
| cyclohexanone | 45% |
| sorbitan monostearate and poly-oxyethylene condensates thereof | 10% |

The ingredients are combined and stirred to produce a solution which can be emulsified in water for application.

EXAMPLE 67

Emulsifiable Concentrate

| | |
|---|---|
| bis(4-Chlorophenyl)methyl(1H—1,2,4-triazol-1-yl-methyl)silane | 45% |
| blend of oil soluble sulfonates and polyoxyethylene ethers | 10% |
| cyclohexanone | 45% |

The ingredients are combined and stirred with gentle warming to speed solution. A fine screen filter is included in packaging operation to insure the absence of any extraneous undissolved material in the product.

EXAMPLE 68

Aqueous Suspension

| | |
|---|---|
| bis(4-fluorophenyl)methyl(1H—1,2,4-triazol-1-yl-methyl)silane | 6% |
| carbendazim | 11% |
| captafol | 33% |
| hydrated attapulgite | 3% |
| crude calcium ligninsulfonate | 10% |
| sodium dihydrogen phosphate | 0.5% |
| water | 36.5% |

The ingredients are ground together in a ball, sand or roller mill until the solid particles have been reduced to diameters under 10 microns.

EXAMPLE 69

Wettable Powder

| | |
|---|---|
| bis(4-fluorophenyl)hydroxy(1H—1,2,4-triazol-1-ylmethyl)silane | 6% |
| carbendazim | 11% |
| captafol | 33% |
| sodium alkylnaphthalenesulfonate | 2% |
| sodium ligninsulfonate | 2% |
| synthetic amorphous silica | 3% |
| kaolinite | 43% |

The ingredients are blended and hammer-milled.

EXAMPLE 70

Aqueous Suspension

| | |
|---|---|
| bis(4-fluorophenyl)methyl(1H—1,2,4-triazol-1-yl-methyl)silane | 6% |
| chlorothalomil | 44% |
| hydrated attapulgite | 3% |
| crude calcium ligninsulfonate | 10% |
| sodium dihydrogen phosphate | 0.5% |
| water | 36.5% |

The ingredients are ground together in a ball, sand or roller mill until the solid particles have been reduced to diameters under 10 microns.

EXAMPLE 71

Wettable Powder

| | |
|---|---|
| bis(4-fluorophenyl)hydroxy(1H—1,2,4-triazol-1-ylmethyl)silane | 6% |
| chlorothalomil | 44% |
| sodium alkylnaphthalenesulfonate | 2% |
| sodium ligninsulfonate | 2% |
| synthetic amorphous silica | 3% |
| kaolinite | 43% |

The ingredients are blended and hammer-milled.

EXAMPLE 72

Wettable Powder

| | |
|---|---|
| bis(4-fluorophenyl)methyl(1H—1,2,4-triazol-1-ylmethyl)silane | 6.25% |
| benomyl | 18.75% |
| sodium alkylnaphthalenesulfonate | 2% |
| sodium ligninsulfonate | 2% |
| diatomaceous earth | 71% |

The benomyl and inerts are blended and hammer-milled. Liquid bis(4-fluorophenyl)methyl(1H-triazol-1-ylmethyl)silane is sprayed unto the other ingredients in a double cone blender.

EXAMPLE 73

Wettable Powder

| | |
|---|---|
| bis(4-fluorophenyl)hydroxy(1H—1,2,4-triazol-1-ylmethyl)silane | 12.5% |
| benomyl | 37.5% |
| sodium alkylnaphthalenesulfonate | 2% |
| sodium ligninsulfonate | 2% |
| synthetic amorphous silica | 3% |
| kaolinite | 43% |

The ingredients are blended and hammer-milled.

EXAMPLE 74

Aqueous Suspension

| | |
|---|---|
| bis(4-fluorophenyl)methyl(1H—1,2,4-triazol-1-yl-methyl)silane | 4.5% |
| maneb | 45.5% |
| hydrated attapulgite | 3% |
| crude calcium ligninsulfonate | 10% |
| sodium dihydrogen phosphate | 0.5% |
| water | 36.5% |

The ingredients are ground together in a ball, sand or roller mill until the solid particles have been reduced to diameters under 10 microns.

EXAMPLE 75

Wettable Powder

| | |
|---|---|
| bis(4-fluorophenyl)hydroxy(1H—1,2,4-triazol-1-ylmethyl)silane | 4.5% |
| maneb | 45.5% |
| sodium alkylnaphthalenesulfonate | 2% |
| sodium ligninsulfonate | 2% |
| synthetic amorphous silica | 3% |
| kaolinite | 43% |

The ingredients are blended and hammer-milled.

EXAMPLE 76

Aqueous Suspension

| | |
|---|---|
| bis(4-fluorophenyl)methyl(1H—1,2,4-triazol-1-yl-methyl)silane | 12.5% |
| carbendazim | 37.5% |
| hydrated attapulgite | 3% |
| crude calcium ligninsulfonate | 10% |
| sodium dihydrogen phosphate | 0.5% |
| water | 36.5% |

The ingredients are ground together in a ball, sand or roller mill until the solid particles have been reduced to diameters under 10 microns.

EXAMPLE 77

Wettable Powder

| | |
|---|---|
| bis(4-fluorophenyl)hydroxy(1H—1,2,4-triazol-1-ylmethyl)silane | 12.5% |
| carbendazim | 37.5% |
| sodium alkylnaphthalenesulfonate | 2% |
| sodium ligninsulfonate | 2% |
| synthetic amorphous silica | 3% |

-continued

| | |
|---|---|
| kaolinite | 43% |

The ingredients are blended and hammer-milled.

EXAMPLE 78

Dust Seed Coat

| | |
|---|---|
| bis(4-fluorophenyl)hydroxy(1H—1,2,4-triazol-1-ylmethyl)silane | 75% |
| Permanent Red 2 B, Calcium Salt, Extended on Blanc Fixe | 5% |
| Diatomaceous earth | 20% |

The ingredients are blended and hammer-milled. The product is reblended before packaging.

Utility

The compounds of this invention are useful as plant disease control agents. They are effective in controlling a broad spectrum of plant diseases, particularly foliar pathogens of ornamental, vegetable, field, cereal and fruit crops, such as, *Puccinia recondita, Erysiphe cichoracearum, Erysiphe graminis, Venturia inaequalis, Helminthosporium maydis, Cercospora arachidicola, Uromyces phaseoli* and *Monilinia fructicola, Rhizoctonia solani, Pyricularia oryzae, Phytophthora infestans* and other Phytophthora species. They also control seed pathogens such as *Pythium aphanadermatum.*

Disease control is ordinarily accomplished by applying an effective amount of the compound either pre- or post-infection to the portion of the plant to be protected, such as the roots, stems, foliage, fruit, seeds, tubers or bulbs, or to the media (soil or sand) in which the plants to be protected are growing. The compound may also be applied to the seed from which the plants to be protected are to be grown.

Rates of application for these compounds can be influenced by many factors of the environment and should be determined under actual use conditions. Foliage can normally be protected when treated at a rate of from less than 1 to 500 ppm of active ingredient. Plants growing in soil treated at a concentration from 0.1 to about 20 kg/ha can be protected from disease. Seed and seedlings can normally be protected when seed is treated at a rate of from 0.06 to about 3 grams per kilogram of seed.

The compounds of this invention can be mixed with fungicides, bactericides, acaricides, nematicides, insecticides, or other biologically active compounds in order to achieve desired results with a minimum expenditure of time, effort and material. Amounts of these biologically active materials added for each part by weight of the composition of this invention may vary from 0.05 to 25 parts by weight. Suitable agents of this type are well-known to those skilled in the art. Some are listed below:

Fungicides methyl 2-benzimidazolecarbamate (carbendazim)
tetramethylthiuram disulfide (thiuram)
n-dodecylguanidine acetate (dodine)
manganese ethylenebisdithiocarbamate (maneb)
1,4-dichloro-2,5-dimethoxybenzene (chloroneb) methyl 1-(butylcarbamoyl)-2-benzimidazolecarbamate (benomyl)
2-cyano-N-ethylcarbamoyl-2-methoxyiminoacetamide (cymoxanil)
N-trichloromethylthiotetrahydrophthalimide (captan)
N-trichloromethylthiophthalimide (folpet)
dimethyl 4,4'-(o-phenylene)bis(3-thioallophanate) (thiophanate-methyl)
2-(thiazol-4-yl)benzimidazole (thiabendazole)
aluminum tris(O-ethyl phosphonate) (phosethyl aluminum)
tetrachloroisophthalonitrile (chlorothalonil)
2,6-dichloro-4-nitroaniline (dichloran)
N-(2,6-dimethylphenyl)-N-(methoxyacetyl)alanine methyl ester (metalaxyl)
cis-N-[(1,1,2,2-tetrachloroethyl)thio]cyclohex-4-ene-1,2-dicarbioximide (captafol)
3-(3,5-dichlorophenyl)-N-(1-methylethyl)-2,4-dioxo-1-imidazolidine carboxamide (iprodione)
3-(3,5-dichlorophenyl)-5-ethenyl-5-methyl-2,4-oxazolidinedione (vinclozolin)
kasugamycin
O-ethyl-S,S-diphenylphosphorodithioate (edifenphos)

Bactericides tribasic copper sulfate
streptomycin sulfate
oxytetracycline

Acaricides senecioic acid, ester with 2-sec-butyl-4,6-dinitrophenol (binapacryl)
6-methyl-1,3-dithiolo[2,3-B]quinonolin-2-one (oxythioquinox)
2,2,2-trichloro-1,1-bis(4-chlorophenyl)ethanol (dicofol)
bis(pentachloro-2,4-cyclopentadien-1-yl) (dienochlor)
tricyclohexyltin hydroxide (cyhexatin)
hexakis(2-methyl-2-phenylpropyl)distannoxane (fenbutin oxide)

Nematicides

2-[diethoxyphosphinylimino]-1,3-diethietane (fosthietan)
S-methyl-1-(dimethylcarbamoyl)-N-(methylcarbamoyloxy)thioformimidate (oxamyl)
S-methyl-1-carbamoyl-N-(methylcarbamoyloxy)thioformimidate
N-isopropylphosphoramidic acid, O-ethyl-O'-[4-(methylthio)-m-tolyl]diester (fenamiphos)

Insecticides 3-hydroxy-N-methylcrotonamide(dimethylphosphate)ester (monocrotophos)
methylcarbamic acid, ester with 2,3-dihydro-2,2-dimethyl-7-benzofuranol (carbofuran)
O-[2,4,5-trichloro-α-(chloromethyl)benzyl]phosphoric acid, O',O'-dimethyl ester (tetrachlorvinphos)
2-mercaptosuccinic acid, diethyl ester, S-ester with thionophosphoric acid, dimethyl ester (malathion)
phosphorothioic acid, O,O-dimethyl, O-p-nitrophenyl ester (methyl parathion)
methylcarbamic acid, ester with α-naphthol (carbaryl)
methyl N-[[(methylamino)carbonyl]oxy]ethanimidothioate (methomyl)
N'-(4-chloro-o-tolyl)-N,N-dimethylformamidine (chlordimeform)
O,O-diethyl-O-(2-isopropyl-4-methyl-6-pyrimidyl)-phosphorothioate (diazinon)
octachlorocamphene (toxaphene)

O-ethyl O-p-nitrophenyl phenylphosphonothioate (EPN)

cyano(3-phenoxyphenyl)-methyl 4-chloro-α-(1-methylethyl)benzeneacetate (fenvalerate)

(3-phenoxyphenyl)methyl (±)-cis,trans-3-(2,2-dichloroethenyl)-2,2-dimethylcyclopropanecarboxylate (permethrin)

dimethyl N,N'-[thiobis[(N-methylimino)carbonyloxy]]-bis[ethanimidothioate] (thiodicarb)

phosphorothiolothionic acid, O-ethyl-O-[4-(methylthio)phenyl]-S-n-propyl ester (sulprofos)

α-cyano-3-phenoxybenzyl 3-(2,2-dichlorovinyl)-2,2-dimethylcyclopropane carboxylate (cypermethrin)

cyano(3-phenoxyphenyl)methyl 4-(difluoromethoxy)-α-(methylethyl)benzeneacetate (flucythrinate)

O,O-diethyl-O-(3,5,6-trichloro-2-pyridyl)phosphorothioate (chlorpyrifos)

O,O-dimethyl-S-[(4-oxo-1,2,3-benzotriazin-3-(4H)-yl)methyl]phosphorodithioate (azinphos-methyl)

5,6-dimethyl-2-dimethylamino-4-pyrimidinyl dimethyl carbamate (pirimicarb)

S-(N-formyl-N-methylcarbamoylmethyl)-O,O-dimethyl phosphorodithioate (formothion)

S-2-(ethylthioethyl)-O,O-dimethyl phosphiorothioate (demeton-S-methyl)

α-cyano-3-phenoxybenzyl cis-3-(2,2-dibromovinyl)-2,2-dimethylcyclopropane carboxylate (deltamethrin)

cyano(3-phenoxyphenyl)methyl ester of N-(2-chloro-4-trifluoromethylphenyl)alanine (fluvalinate)

This invention is further illustrated by the following examples.

EXAMPLE 79

The compounds of this invention were dissolved in acetone in an amount equal to 6% of the final volume and then suspended at a concentration of 100 ppm in purified water containing 250 ppm of the surfactant TREM 014 (polyhydric alcohol esters). These suspensions were sprayed to the point of run-off on wheat seedlings. The following day, the plants were inoculated with a spore suspension of *Puccinia recondita* var. *tritici*, causal agent of wheat leaf rust, and incubated in a saturated humidity chamber at 20° for 24 hours and then in a growth room for an additional 7 days, when disease ratings were made. Percent disease control is shown in the following table. Treated plants from successful treatments had few or no rust pustules while the untreated plants had numerous rust pustules on each leaf.

TABLE 1

| Compound | % Control Wheat Rust |
|---|---|
| (Dimethyl)phenyl(1,2,4-triazol-1-ylmethyl)silane | 90 |
| Ethyldimethyl(1H—1,2,4-triazol-1-ylmethyl)silane | 0 |
| Butyldimethyl(1H—1,2,4-triazol-1-ylmethyl)silane | 0 |
| Dimethyl(4-methylphenyl)(1H—1,2,4-triazol-1-ylmethyl)silane | 0 |
| (4-Bromophenyl)dimethyl(1H—1,2,4-triazol-1-ylmethyl)silane | 80 |
| (1,1'-Biphenyl-4-yl)dimethyl(1H—1,2,4-triazol-1-ylmethyl)silane | 100 |
| (4-Chlorophenyl)dimethyl(1H—1,2,4-triazol-1-ylmethyl)silane | 100 |
| Butyl(4-chlorophenyl)methyl(1H—1,2,4-triazol-1-ylmethyl)silane | 80 |
| Dimethyl(1-naphthalenyl)(1H—1,2,4-triazol-1-ylmethyl)silane | 0 |

TABLE 1-continued

| Compound | % Control Wheat Rust |
|---|---|
| (3,4-Dichlorophenyl)dimethyl(1H—1,2,4-triazol-1-ylmethyl)silane | 60 |
| Dimethyl(4-phenoxyphenyl)(1H—1,2,4-triazol-1-ylmethyl)silane | 0 |
| Dimethyl(4-methoxyphenyl)(1H—1,2,4-triazol-1-ylmethyl)silane | 0 |
| (2,4-Dichlorophenyl)dimethyl(1H—1,2,4-triazol-1-ylmethyl)silane | 90 |
| bis(4-Chlorophenyl)(methyl)(1H—1,2,4-triazol-1-ylmethyl)silane | 90 |
| (1H—1,2,4-Triazol-1-ylmethyl)triphenylsilane | 0 |
| Methyldiphenyl(1H—1,2,4-triazol-1-ylmethyl)silane | 0 |
| (1,1'-Biphenyl-4-yl)dimethyl(4H—1,2,4-triazol-4-ylmethyl)silane | 0 |
| bis(4-Fluorophenyl)(methyl)(1H—1,2,4-triazol-1-ylmethyl)silane | 0 |
| Dimethyl(4-fluorophenyl)(1H—1,2,4-triazol-1-ylmethyl)silane | 100 |
| Dimethyl(4-methylthiophenyl)(1H—1,2,4-triazol-1-ylmethyl)silane | 0 |
| Dimethyl(1H—1,2,4-triazol-1-ylmethyl)(4-trifluoromethylphenyl)silane | 0 |
| Dimethyl(1H—1,2,4-triazol-1-ylmethyl)(3-trifluoromethylphenyl)silane | 0 |
| | 0 |
| [4-(1,1-Dimethylethyl)phenyl]dimethyl(1H—1,2,4-triazol-1-ylmethyl)silane | 80[A] |
| | 80[A] |
| (2-Methoxyphenyl)dimethyl(1H—1,2,4-triazol-1-ylmethyl)silane | 0 |
| Butyl(2,4-dichlorophenyl)methyl(1H—1,2,4-triazol-1-ylmethyl)silane | 100 |
| bis(2,4-Dichlorophenyl)(methyl)(1H—1,2,4-triazol-1-ylmethyl)silane | 100 |
| (2,4-Dichlorophenyl)methyl(phenyl)(1H—1,2,4-triazol-1-ylmethyl)silane | 100 |
| (4-Chlorophenyl)methyl(phenyl)(1H—1,2,4-triazol-1-ylmethyl)silane | 100 |
| (4-Fluorophenyl)methyl(phenyl)(1H—1,2,4-triazol-1-ylmethyl)silane | 90 |
| Butyl(methyl)phenyl(1H—1,2,4-triazol-1-ylmethyl)silane | 0 |
| (2,3-Dimethoxyphenyl)dimethyl(1H—1,2,4-triazol-1-ylmethyl)silane | 0 |
| (2,6-Dimethoxyphenyl)dimethyl(1H—1,2,4-triazol-1-ylmethyl)silane | 0 |
| Dodecyl(dimethyl)(1H—1,2,4-triazol-1-ylmethyl)silane | 100[A] |
| (2-Chlorophenyl)dimethyl(1H—1,2,4-triazol-1-ylmethyl)silane | 0 |
| [4-(4-Chlorophenoxy)phenyl]dimethyl(1H—1,2,4-triazol-1-ylmethyl)silane | 90 |
| (3,5-Dichlorophenyl)dimethyl(1H—1,2,4-triazol-1-ylmethyl)silane | 80 |
| (1,1'-Biphenyl-4-yl)butyl(methyl(1H—1,2,4-triazol-1-ylmethyl)silane | 90 |
| Butyl(4-fluorophenyl)methyl(1H—1,2,4-triazol-1-ylmethyl)silane | 0 |
| Dibutyl(methyl)(1H—1,2,4-triazol-1-ylmethyl)silane | 0 |
| bis(1,1'-Biphenyl-4-yl)(methyl)(1H—1,2,4-triazol-1-ylmethyl)silane | 80 |
| (1,1'-Biphenyl-4-yl)methyl(phenyl)(1H—1,2,4-triazol-1-ylmethyl)silane | 100 |
| (1,1-Dimethylethoxy)methyl(phenyl)(1H—1,2,4-triazol-1-ylmethyl)silane | 0 |
| Methyl(phenyl)(2-propoxy)(1H—1,2,4-triazol-1-ylmethyl silane | 0 |
| [bis(4-Methoxyphenyl)]methyl(1H—1,2,4-triazol-1-ylmethyl)silane | 0 |
| (1,1'-Biphenyl-2-yl)dimethyl(1H—1,2,4-triazol-1-ylmethyl)silane | 0 |
| (1,1'-Biphenyl-3-yl)dimethyl(1H—1,2,4-triazol-1-ylmethyl)silane | 80 |
| 2-Chlorophenyl(methyl)phenyl(1H—1,2,4-triazol-1-ylmethyl)silane | 80 |

TABLE 1-continued

| Compound | % Control Wheat Rust |
|---|---|
| 4-Bromophenyl(methyl)phenyl(1H—1,2,4-triazol-1-ylmethyl)silane | 0 |
| [bis(2-Chlorophenyl)]methyl(1H—1,2,4-triazol-1-ylmethyl)silane | 100 |
| Dimethyl(4-methylsulfonylphenyl)(1H—1,2,4-triazol-1-ylmethyl)silane | 0 |
| Cyclohexyl(dimethyl)(1H—1,2,4-triazol-1-ylmethyl)silane | 0 |
| [bis(4-Bromophenyl)]9 methyl(1H—1,2,4-triazol-1-ylmethyl)silane | 0 |
| (1,1'-Biphenyl-4-yl)dimethyl(1H—1,2,4-triazol-1-ylmethyl)silane, 4-dodecylbenzenesulfonic acid salt | 100 |
| (1,1'-Biphenyl-4-yl)dimethyl(1H—1,2,4-triazol-1-ylmethyl)silane, 1:1 complex with cuprous chloride | 0 |
| (1,1'-Biphenyl-4-yl)dimethyl(1H—1,2,4-triazol-1-ylmethyl)silane, 1:1 complex with zinc (II) chloride | 100 |
| (1,1'-Biphenyl-4-yl)dimethyl(1H—1,2,4-triazol-1-ylmethyl)silane, 1:1 complex with manganous sulfate | 90 |
| 2-Chlorophenyl(4-chlorophenyl)methyl-(1H—1,2,4-triazol-1-ylmethyl)silane | 100 |
| Phenyl[bis(2-propoxy)](1H—1,2,4-triazol-1-ylmethyl)silane | 0 |
| 2-Chlorophenyl(dimethyl)(1H—1,2,4-triazol-1-ylmethyl)silane | 0 |
| [bis(4-Fluorophenyl)]methyl(1H—1,2,4-triazol-1-ylmethyl)silane, 1:1 complex with cuprous chloride | 90 |
| [bis(4-Fluorophenyl)]methyl(1H—1,2,4-triazol-1-ylmethyl)silane, 2:1 complex with cupric chloride | 100 |
| bis(4-Chlorophenyl)hydroxy(1H—1,2,4-triazol-1-ylmethyl)silane | 90 |
| bis(4-Fluorophenyl)hydroxy(1H—1,2,4-triazol-1-ylmethyl)silane | 90 |
| tris(4-Chlorophenyl)(1H—1,2,4-triazol-1-ylmethyl)silane | 40 |
| tris(4-Fluorophenyl)(1H—1,2,4-triazol-1-ylmethyl)silane | 90 |
| bis(4-Chlorophenyl)hydroxy(4H—1,2,4-triazol-4-ylmethyl)silane | 90 |
| Oxybis[bis(4-fluorophenyl)(1H—1,2,4-triazol-1-ylmethyl)silane] | 100 |
| (1,1'-Biphenyl-4-yl)methyl(2-propoxy)-(1H—1,2,4-triazol-1-ylmethyl)silane | 100 |
| (3-Chlorophenyl)dimethyl(1H—1,2,4-triazol-1-ylmethyl)silane | 0 |
| (1,1'-Biphenyl-4-yl)hydroxy(methyl)-(1H—1,2,4-triazol-1-ylmethyl)silane | 90 |
| (1,1'-Biphenyl-4-yl)(4-fluorophenyl)-methyl(1H—1,2,4-triazol-1-ylmethyl)-silane | 100 |
| Dimethyl(4-trifluoromethoxyphenyl)(-1H—1,2,4-triazol-1-ylmethyl)silane | 100 |
| (4'-Bromo-1,1'-biphenyl-4-yl)dimethyl-(1H—1,2,4-triazol-1-ylmethyl)silane | 100 |
| (1,1'-Biphenyl-4-yl)dimethyl(5-methyl-1H—1,2,4-triazol-1-ylmethyl)silane | 100 |
| (1'1'-Biphenyl-4-yl)dimethyl(1H—1,2,4-triazol-1-ylmethyl)silane, 1:1 complex with cupric chloride | 100 |
| (1,1'-Biphenyl-4-yl)dimethyl(1H—1,2,4-triazol-1-ylmethyl)silane, 2:1 complex with cupric chloride | 100 |
| Methyl[bis(4-methylphenyl)](1H—1,2,4-triazol-1-ylmethyl)silane | 0 |
| Dimethyl(octadecyl)(1H—1,2,4-triazol-1-ylmethyl)silane | 0 |
| bis(4-Fluorophenyl)methyl[1-(1H—1,2,4-triazol-1-yl)ethyl]silane | 100 |

[A]Compound applied at a concentration of 200 ppm.

EXAMPLE 80

The compounds of the previous example were again dissolved in acetone in an amount equal to 6% of the final volume and then suspended at a concentration of 100 ppm in purified water containing 250 ppm of the surfactant TREM 014 (polyhydric alcohol esters). These suspensions were sprayed to the point of run-off, on cucumber seedlings. The following day, the plants were inoculated with a spore suspension of the fungus *Erysiphe cichoracearum*, causal agent of cucumber powdery mildew, and incubated in a growth room for 7 days. Disease ratings were then made. Percent disease control is shown in the following table. Treated plants from successful treatments had little or no powdery mildew in contrast to untreated plants which were covered with powdery mildew. Phytotoxicity in the form of growth reduction or hormonal effects was observed on some of the plants in association with disease control.

TABLE 2

| Compound | % Control Cucumber Powdery Mildew |
|---|---|
| (Dimethyl)phenyl(1,2,4-triazol-1-ylmethyl)silane | 100 |
| Ethyldimethyl(1H—1,2,4-triazol-1-ylmethyl)silane | 100 |
| Butyldimethyl(1H—1,2,4-triazol-1-ylmethyl)silane | 100 |
| Dimethyl(4-methylphenyl)(1H—1,2,4-triazol-1-ylmethyl)silane | 100G[A] |
| (4-Bromophenyl)dimethyl(1H—1,2,4-triazol-1-ylmethyl)silane | 100G |
| (1,1'-Biphenyl-4-yl)dimethyl(1H—1,2,4-triazol-1-ylmethyl)silane | 100 |
| (4-Chlorophenyl)dimethyl(1H—1,2,4-triazol-1-ylmethyl)silane | 100 |
| Butyl(4-chlorophenyl)methyl(1H—1,2,4-triazol-1-ylmethyl)silane | 100G |
| Dimethyl(1-naphthalenyl)(1H—1,2,4-triazol-1-ylmethyl)silane | 100 |
| (3,4-Dichlorophenyl)dimethyl(1H—1,2,4-triazol-1-ylmethyl)silane | 100 |
| Dimethyl(4-phenoxyphenyl)(1H—1,2,4-triazol-1-ylmethyl)silane | 70 |
| Dimethyl(4-methoxyphenyl)(1H—1,2,4-triazol-1-ylmethyl)silane | 100 |
| (2,4-Dichlorophenyl)dimethyl(1H—1,2,4-triazol-1-ylmethyl)silane | 100H[B] |
| bis(4-Chlolophenyl)(methyl)(1H—1,2,4-triazol-1-ylmethyl)silane | 100 |
| (1H—1,2,4-Triazol-1-ylmethyl)triphenylsilane | 100 |
| Methyldiphenyl(1H—1,2,4-triazol-1-ylmethyl)silane | 100G |
| (1,1'-Biphenyl-4-yl)dimethyl(4H—1,2,4-triazol-4-ylmethyl)silane | 90 |
| bis(4-Fluorophenyl)(methyl)(1H—1,2,4-triazol-1-ylmethyl)silane | 100G |
| Dimethyl(4-fluorophenyl)(1H—1,2,4-triazol-1-ylmethyl)silane | 100G |
| Dimethyl(4-methylthiophenyl)(1H—1,2,4-triazol-1-ylmethyl)silane | 100 |
| Dimethyl(1H—1,2,4-triazol-1-ylmethyl)(4-trifluoromethylphenyl)-silane | 100G |
| Dimethyl(1H—1,2,4-triazol-1-ylmethyl)(3-trifluoromethylphenyl)-silane | 100 |
| [4-(1,1-Dimethylethyl)phenyl]dimethyl(1H—1,2,4-triazol-1-ylmethyl)silane | 0 |
| Dimethyl(1H— 1,2,4-triazol-1-ylmethyl)(2-trifluoromethylphenyl)-silane | 100 |
| (2-Methoxyphenyl)dimethyl(1H—1,2,4-triazol-1-ylmethyl)silane | 100G |
| Butyl(2,4-dichlorophenyl)methyl(1H— | 100G |

TABLE 2-continued

| Compound | % Control Cucumber Powdery Mildew |
|---|---|
| 1,2,4-triazol-1-ylmethyl)silane | |
| bis(2,4-Dichlorophenyl)(methyl)(1H—1,2,4-triazol-1-ylmethyl)silane | 100G |
| (2,4-Dichlorophenyl)methyl(phenyl)-(1H—1,2,4-triazol-1-ylmethyl)silane | 100G |
| (4-Chlorophenyl)methyl(phenyl)(1H—1,2,4-triazol-1-ylmethyl)silane | 100G |
| (4-Fluorophenyl)methyl(phenyl)(1H—1,2,4-triazol-1-ylmethyl)silane | 100 |
| Butyl(methyl)phenyl(1H—1,2,4-triazol-1-ylmethyl)silane | 100 |
| (2,3-Dimethoxyphenyl)dimethyl(1H—1,2,4-triazol-1-ylmethyl)silane | 100G |
| (2,6-Dimethoxyphenyl)dimethyl(1H—1,2,4-triazol-1-ylmethyl)silane | 100G |
| Dodecyl(dimethyl)(1H—1,2,4-triazol-1-ylmethyl)silane | 60[C] |
| (2-Chlorophenyl)dimethyl(1H—1,2,4-triazol-1-ylmethyl)silane | 100G |
| [4-(4-Chlorophenoxy)phenyl]dimethyl-(1H—1,2,4-triazol-1-ylmethyl)silane | 80 |
| (3,5-Dichlorophenyl)dimethyl(1H—1,2,4-triazol-1-ylmethyl)silane | 0 |
| (1,1'Biphenyl-4-yl)butyl(methyl)-(1H—1,2,4-triazol-1-ylmethyl)silane | 100 |
| Butyl(4-fluorophenyl)methyl(1H—1,2,4-triazol-1-ylmethyl)silane | 100 |
| Dibutyl(methyl)(1H—1,2,4-triazol-1-ylmethyl)silane | 0 |
| bis(1,1'-Biphenyl-4-yl)(methyl)(1H—1,2,4-triazol-1-ylmethyl)silane | 100 |
| (1,1'-Biphenyl-4-yl)methyl(phenyl)-(1H—1,2,4-triazol-1-ylmethyl)silane | 100 |
| (1,1-Dimethylethoxy)methyl(phenyl)-(1H—1,2,4-triazol-1-ylmethyl)silane | 100 |
| Methyl(phenyl)(2-propoxy)(1H—1,2,4-triazol-1-ylmethyl)silane | 100 |
| [bis(4-Methoxyphenyl)]methyl(1H—1,2,4-triazol-1-ylmethyl)silane | 0 |
| (1,1'-Biphenyl-2-yl)dimethyl(1H—1,2,4-triazol-1-ylmethyl)silane | 90 |
| (1,1'-Biphenyl-3-yl)dimethyl(1H— 1,2,4-triazol-1-ylmethyl)silane | 0 |
| 2-Chlorophenyl(methyl)phenyl(1H—1,2,4-triazol-1-ylmethyl)silane | 100 |
| 4-Bromophenyl(methyl)phenyl(1H—1,2,4-triazol-1-ylmethyl)silane | 100 |
| [bis(2-Chlorophenyl)]methyl(1H—1,2,4-triazol-1-ylmethyl)silane | 100 |
| Dimethyl(4-methylsulfonylphenyl)(1H—1,2,4-triazol-1-ylmethyl silane | 0 |
| Cyclohexyl(dimethyl)(1H—1,2,4-triazol-1-ylmethyl)silane | 100G |
| [bis(4-Bromophenyl)]methyl(1H—1,2,4-triazol-1-ylmethyl)silane | 80G |
| (1,1'-Biphenyl-4-yl)dimethyl(1H—1,2,4-triazol-1-ylmethyl)silane, 4-dodecylbenzenesulfonic acid salt | 100 |
| (1,1'-Biphenyl-4-yl)dimethyl(1H—1,2,4-triazol-1-ylmethyl)silane, 1:1 complex with cuprous chloride | 100 |
| 1,1'-Biphenyl-4-yl)dimethyl(1H—1,2,4-triazol-1-ylmethyl)silane, 1:1 complex with zinc (II) chloride | 80 |
| (1,1'-Biphenyl-4-yl)dimethyl(1H—1,2,4-triazol-1-ylmethyl)silane, 1:1 complex with manganous sulfate | 90 |
| 2-Chlorophenyl(4-chlorophenyl)methyl-(1H—1,2,4-triazol-1-ylmethyl)silane | 100 |
| Phenyl[bis(2-propoxy)](1H—1,2,4-triazol-1-ylmethyl)silane | 100 |
| 2-Chlorophenyl)dimethyl)(1H—1,2,4-triazol-1-ylmethyl)silane | 0 |
| [bis(4-Fluorophenyl)]methyl(1H—1,2,4-triazol-1-ylmethyl)silane, 1:1 complex with cuprous chloride | 100 |
| [bis(4-Fluorophenyl)]methyl(1H—1,2,4-triazol-1-ylmethyl)silane, 2:1 complex with cupric chloride | 100 |
| bis(4-Chlorophenyl)hydroxy(1H—1,2,4-triazol-1-ylmethyl)silane | 100H |
| bis(4-Fluorophenyl)hydroxy(1H—1,2,4-triazol-1-ylmethyl)silane | 100H |
| tris(4-Chlorophenyl)(1H—1,2,4-triazol-1-ylmethyl)silane | 100 |
| tris(4-Fluorophenyl)(1H—1,2,4-triazol-1-ylmethyl)silane. | 0 |
| bis(4-Chlorophenyl)hydroxy(4H—1,2,4-triazol-4-ylmethyl)silane | 100 |
| Oxybis[bis(4-fluorophenyl)(1H—1,2,4-triazol-1-ylmethyl)silane] | 100 |
| (1,1'-Biphenyl-4-yl)methyl(2-propoxy)-(1H—1,2,4-triazol-1-ylmethyl)silane | 100 |
| (3-Chlorophenyl)dimethyl(1H—1,2,4-triazol-1-ylmethyl)silane | 0 |
| (1,1'-Biphenyl-4-yl)hydroxy(methyl)-(1H—1,2,4-triazol-1-ylmethyl)silane | 100 |
| (1,1'-Biphenyl-4-yl)(4-fluorophenyl)-methyl(1H—1,2,4-triazol-1-ylmethyl)-silane | 100 |
| Dimethyl(4-trifluoromethoxyphenyl)(1H—1,2,4-triazol-1-ylmethyl)silane | 100G |
| (4'-Bromo-1,1'-biphenyl-4-yl)dimethyl-(1H—1,2,4-triazol-1-ylmethyl)silane | 100 |
| (1,1'-Biphenyl-4-yl)dimethyl(5-methyl-1H—1,2,4-triazol-1-ylmethyl)silane | 100 |
| (1,1'-Biphenyl-4-yl)dimethyl(1H—1,2,4-triazol-1-ylmethyl)silane, 1:1 complex with cupric chloride | 100 |
| (1,1'-Biphenyl-4-yl)dimethyl(1H—1,2,4-triazol-1-ylmethyl)silane, 2:1 complex with cupric chloride | 100 |
| Methyl[bis(4-methylphenyl)](1H—1,2,4-triazol-1-ylmethyl)silane | 0 |
| Dimethyl(octadecyl)(1H—1,2,4-triazol-1-ylmethyl)silane | 0 |
| (4-Fluorophenyl)methyl(2-propoxy)(1H—1,2,4-triazol-1-ylmethyl)silane | 100 |
| (1,1-Dimethylethoxy)[bis(4-fluorophenyl)](1H—1,2,4-triazol-1-ylmethyl)-silane | 100 |
| bis(4-Fluorophenyl)methyl[1-(1H—1,2,4-triazol-1-yl)ethyl]silane | 100 |

[A]G = growth reduction;
[B]H = hormonal effects; and
[C]compound applied at a concentration of 400 ppm.

EXAMPLE 81

The compounds of the previous examples were again dissolved in acetone in an amount equal to 6% of the final volume and then suspended at a concentration of 100 ppm in purified water containing 250 ppm of the surfactant TREM 014 (polyhydric alcohol esters). These suspensions were sprayed to the point of run-off on barley seedlings. The following day, the plants were inoculated with a spore suspension of the fungus *Erysiphe graminis,* causal agent of barley powdery mildew, and incubated in growth room for 7 days. Disease ratings were then made. Percent disease control is shown in the following table. Treated plants from successful treatments had little or no powdery mildew in contrast to untreated plants which were covered with powdery mildew.

TABLE 3

| Compound | % Control Barley Powdery Mildew |
|---|---|
| Butyl(4-chlorophenyl)methyl(1H—1,2,4-triazol-1-ylmethyl)silane | 90 |
| Dimethyl(1-naphthalenyl)(1H—1,2,4-triazol-1-ylmethyl)silane | 0 |
| (3,4-Dichlorophenyl)dimethyl(1H—1,2,4-triazol-1-ylmethyl)silane | 100 |

TABLE 3-continued

| Compound | % Control Barley Powdery Mildew |
| --- | --- |
| Dimethyl(4-phenoxyphenyl)(1H—1,2,4-triazol-1-ylmethyl)silane | 0 |
| Dimethyl(4-methoxyphenyl)(1H—1,2,4-triazol-1-ylmethyl)silane | 100 |
| (2,4-Dichlorophenyl)dimethyl(1H—1,2,4-triazol-1-ylmethyl)silane | 100 |
| bis(4-Chlorophenyl)(methyl)(1H—1,2,4-triazol-1-ylmethyl)silane | 100 |
| (1H—1,2,4-Triazol-1-ylmethyl)triphenylsilane | 100 |
| Methyldiphenyl(1H—1,2,4-triazol-1-ylmethyl)silane | 100 |
| (1,1'-Biphenyl-4-yl)dimethyl(4H—1,2,4-triazol-4-ylmethyl)silane | 0 |
| Dimethyl(1H—1,2,4-triazol-1-ylmethyl)(2-trifluoromethylphenyl)silane | 100 |
| Dodecyl(dimethyl)(1H—1,2,4-triazol-1-ylmethyl)silane | $100^A$ |

$^A$Compound applied at a concentration of 200 ppm.

EXAMPLE 82

The compounds of the previous examples were again dissolved in acetone in an amount equal to 6% of the final volume and then suspended at a concentration of 100 ppm in purified water containing 250 ppm of the surfactant TREM 014 (polyhydric alcohol esters). These suspensions were sprayed to the point of run-off on apple seedlings. The following day, the plants were inoculated with a spore suspension of the fungus *Venturia inaequalis*, causal agent of apple scab, and incubated in a saturated humidity chamber at 20° for 24 hours and then in a growth room for an additional 10-12 days. Disease ratings were then made and recorded as shown in the following table. Treated plants from successful treatments had fewer apple scab lesions when compared to untreated plants which were covered with scab lesions. Phytotoxicity expressed as growth reduction was observed on some of the plants in association with disease control.

TABLE 4

| Compound | % Control Apple Scab |
| --- | --- |
| (Dimethyl)phenyl(1,2,4-triazol-1-ylmethyl)silane | 0 |
| Ethyldimethyl(1H—1,2,4-triazol-1-ylmethyl)silane | 0 |
| Butyldimethyl(1H—1,2,4-triazol-1-ylmethyl)silane | 0 |
| Dimethyl(4-methylphenyl)(1H—1,2,4-triazol-1-ylmethyl)silane | $50G^A$ |
| (4-Bromophenyl)dimethyl(1H—1,2,4-triazol-1-ylmethyl)silane | 90G |
| (1,1'-Biphenyl-4-yl)dimethyl(1H—1,2,4-triazol-1-ylmethyl)silane | 100 |
| (4-Chlorophenyl)dimethyl(1H—1,2,4-triazol-1-ylmethyl)silane | 100 |
| Butyl(4-chlorophenyl)methyl(1H—1,2,4-triazol-1-ylmethyl)silane | 100G |
| Dimethyl(1-naphthalenyl)(1H—1,2,4-triazol-1-ylmethyl)silane | 50 |
| (3,4-Dichlorophenyl)dimethyl(1H—1,2,4-triazol-1-ylmethyl)silane | 80 |
| Dimethyl(4-phenoxyphenyl)(1H—1,2,4-triazol-1-ylmethyl)silane | 100 |
| Dimethyl(4-methoxyphenyl)(1H—1,2,4-triazol-1-ylmethyl)silane | 100 |
| (2,4-Dichlorophenyl)dimethyl(1H—1,2,4-triazol-1-ylmethyl)silane | 100 |
| bis(4-Chlorophenyl)(methyl)(1H—1,2,4-triazol-1-ylmethyl)silane | 100 |

TABLE 4-continued

| Compound | % Control Apple Scab |
| --- | --- |
| (1H—1,2,4-Triazol-1-ylmethyl)triphenylsilane | 0 |
| Methyldiphenyl(1H—1,2,4-triazol-1-ylmethyl)silane | 100 |
| (1,1'-Biphenyl-4-yl)dimethyl(4H—1,2,4-triazol-4-ylmethyl)silane | 80 |
| bis(4-Fluorophenyl)(methyl)(1H—1,2,4-triazol-1-ylmethyl)silane | 100 |
| Dimethyl(4-fluorophenyl)(1H—1,2,4-triazol-1-ylmethyl)silane | $80C^B$ |
| Dimethyl(4-methylthiophenyl)(1H—1,2,4-triazol-1-ylmethyl)silane | 60 |
| Dimethyl(1H—1,2,4-triazol-1-ylmethyl)(4-trifluoromethylphenyl)silane | 0 |
| Dimethyl(1H—1,2,4-triazol-1-ylmethyl)(3-trifluoromethylphenyl)silane | 0 |
| [4-(1,1-Dimethylethyl)phenyl]dimethyl(1H—1,2,4-triazol-1-ylmethyl)silane | 0 |
| Dimethyl(1H—1,2,4-triazol-1-ylmethyl)(2-trifluoromethylphenyl)silane | $65G^{A,C}$ |
| (2-Methoxyphenyl)dimethyl(1H—1,2,4-triazol-1-ylmethyl)silane | 80 |
| Butyl(2,4-dichlorophenyl)methyl(1H—1,2,4-triazol-1-ylmethyl)silane | 100G |
| bis(2,4-Dichlorophenyl)(methyl)(1H—1,2,4-triazol-1-ylmethyl)silane | 100 |
| (2,4-Dichlorophenyl)methyl(phenyl)(1H—1,2,4-triazol-1-ylmethyl)silane | 100G |
| (4-Chlorophenyl)methyl(phenyl)1H—1,2,4-triazol-1-ylmethyl)silane | 100 |
| (4-Fluorophenyl)methyl(phenyl)(1H—1,2,4-triazol-1-ylmethyl)silane | 100 |
| Butyl(methyl)phenyl(1H—1,2,4-triazol-1-ylmethyl)silane | 80 |
| (2,3-Dimethoxyphenyl)dimethyl(1H—1,2,4-triazol-1-ylmethyl)silane | 0 |
| (2,6-Dimethoxyphenyl)dimethyl(1H—1,2,4-triazol-1-ylmethyl)silane | 0 |
| Dodecyl(dimethyl)(1H—1,2,4-triazol-1-ylmethyl)silane | $40B^{C,D}$ |
| (2-Chlorophenyl)dimethyl(1H—1,2,4-triazol-1-ylmethyl)silane | 100 |
| [4-(4-Chlorophenoxy)phenyl]dimethyl-(1H—1,2,4-triazol-1-ylmethyl)silane | 100 |
| (3,5-Dichlorophenyl)dimethyl(1H—1,2,4-triazol-1-ylmethyl)silane | 0 |
| (1,1'-Biphenyl-4-yl)butyl(methyl)-(1H—1,2,4-triazol-1-ylmethyl)silane | 80 |
| Butyl(4-fluorophenyl)methyl(1H—1,2,4-triazol-1-ylmethyl)silane | 100 |
| Dibutyl(methyl)(1H—1,2,4-triazol-1-ylmethyl)silane | 0 |
| bis(1,1'-Biphenyl-4-yl)(methyl)(1H—1,2,4-triazol-1-ylmethyl)silane | 0 |
| (1,1'-Biphenyl-4-yl)methyl(phenyl)-(1H—1,2,4-triazol-1-ylmethyl)silane | 100 |
| (1,1-Dimethylethoxy)methyl(phenyl)-(1H—1,2,4-triazol-1-ylmethyl)silane | 0 |
| Methyl(phenyl)(2-propoxy)(1H—1,2,4-triazol-1-ylmethyl)silane | 0 |
| [bis(4-Methoxyphenyl)]methyl(1H—1,2,4-triazol-1-ylmethyl)silane | 0 |
| (1,1'-Biphenyl-2-yl)dimethyl(1H—1,2,4-triazol-1-ylmethyl)silane | 60 |
| (1,1'-Biphenyl-3-yl)dimethyl(1H—1,2,4-triazol-1-ylmethyl)silane | 50 |
| 2-Chlorophenyl(methyl)phenyl(1H— 1,2,4-triazol-1-ylmethyl)silane | 90 |
| 4-Bromophenyl(methyl)phenyl(1H—1,2,4-triazol-1-ylmethyl)silane | 100 |
| [bis(2-Chlorophenyl)]methyl(1H—1,2,4-triazol-1-ylmethyl)silane | 40 |
| Dimethyl(4-methylsulfonylphenyl)(1H—1,2,4-triazol-1-ylmethyl)silane | 0 |
| Cyclohexyl(dimethyl)(1H—1,2,4-triazol-1-ylmethyl)silane | 0 |
| [bis(4-Bromophenyl)]methyl(1H—1,2,4- | 80 |

TABLE 4-continued

| Compound | % Control Apple Scab |
|---|---|
| triazol-1-ylmethyl)silane | |
| (1,1'-Biphenyl-4-yl)dimethyl(1H—1,2,4-triazol-1-ylmethyl)silane, 4-dodecylbenzenesulfonic acid salt | 100 |
| (1,1'-Biphenyl-4-yl)dimethyl(1H—1,2,4-triazol-1-ylmethyl)silane, 1:1 complex with cuprous chloride | 100 |
| (1,1'-Biphenyl-4-yl)dimethyl(1H—1,2,4-triazol-1-ylmethyl)silane, 1:1 complex with zinc (II) chloride | 100 |
| (1,1'-Biphenyl-4-yl)dimethyl(1H—1,2,4-triazol-1-ylmethyl)silane, 1:1 complex with manganous sulfate | 100 |
| 2-Chlorophenyl(4-chlorophenyl)methyl-(1H—1,2,4-triazol-1-ylmethyl)silane | 90 |
| Phenyl[bis(2-propoxy)](1H—1,2,4-triazol-1-ylmethyl)silane | 0 |
| 2-Chlorophenyl dimethyl)(1H—1,2,4-triazol-1-ylmethyl)silane | 60 |
| bis(4-Chlorophenyl)hydroxy(1H—1,2,4-triazol-1-ylmethyl)silane | 100 |
| bis(4-Fluorophenyl)hydroxy(1H—1,2,4-triazol-1-ylmethyl)silane | 100 |
| tris(4-Chlorophenyl)(1H—1,2,4-triazol-1-ylmethyl)silane | 0 |
| tris(4-Fluorophenyl)(1H—1,2,4-triazol-1-ylmethyl)silane | 60 |
| bis(4-Chlorophenyl)hydroxy(4H—1,2,4-triazol-4-ylmethyl)silane | 100 |
| Oxybis[bis(4-fluorophenyl)(1H—1,2,4-triazol-1-ylmethyl)silane] | 100 |
| (1,1'-Biphenyl-4-yl)methyl(2-propoxy)-(1H—1,2,4-triazol-1-ylmethyl)silane | 100 |
| (3-Chlorophenyl)dimethyl(1H—1,2,4-triazol-1-ylmethyl)silane | 60 |
| (1,1'-Biphenyl-4-yl)hydroxy(methyl)-(1H—1,2,4-triazol-1-ylmethyl)silane | 100 |
| (1,1'-Biphenyl-4-yl)(4-fluorophenyl)-methyl(1H—1,2,4-triazol-1-ylmethyl)-silane | 100 |
| Dimethyl(4-trifluoromethoxyphenyl)(1H—1,2,4-triazol-1-ylmethyl)silane | 90 |
| (4'-Bromo-1,1'-biphenyl-4-yl)dimethyl-(1H—1,2,4-triazol-1-ylmethyl)silane | 100 |
| (1,1'-Biphenyl-4-yl)dimethyl(5-methyl-1H—1,2,4-triazol-1-ylmethyl)silane | 100 |
| (1,1'-Biphenyl-4-yl)dimethyl(1H—1,2,4-triazol-1-ylmethyl)silane, 1:1 complex with cupric chloride | 100 |
| (1,1'-Biphenyl-4-yl)dimethyl(1H—1,2,4-triazol-1-ylmethyl)silane, 2:1 complex with cupric chloride | 100 |
| Methyl[bis(4-methylphenyl)](1H—1,2,4-triazol-1-ylmethyl,silane | 0 |
| Dimethyl(octadecyl)(1H—1,2,4-triazol-1-ylmethyl)silane | 60 |
| bis(4-Fluorophenyl)methyl[1-(1H—1,2,4-triazol-1-yl)ethyl]silane | 100 |

[A]G = growth reduction;
[B]C = chlorosis;
[C]compound applied at a concentration of 400 ppm;
[D]B = burn.

EXAMPLE 83

The compounds of the previous examples were again dissolved in acetone in an amount equal to 6% of the final volume and then suspended at a concentration of 100 ppm in purified water containing 250 ppm of the surfactant TREM 014 (polyhydric alcohol esters). These suspensions were sprayed to the point of run-off on corn seedlings. The following day, the plants were inoculated with a spore suspension of *Helminthosporium maydis*, causal agent of southern corn leaf blight, and incubated in a saturated humidity chamber at 20° for 24 hours and then in a growth room for an additional 7 days, when disease ratings were made. Percent disease control is shown in the following table. Treated plants from successful treatments had few or no lesions while the untreated plants had numerous lesions on each leaf. Phytotoxicity expressed as growth reduction was observed on some of the plants in association with disease control.

TABLE 5

| Compound | % Control of Southern Corn Leaf Blight |
|---|---|
| (Dimethyl)phenyl(1,2,4-triazol-1-ylmethyl)silane | 0 |
| Ethyldimethyl(1H—1,2,4-triazol-1-ylmethyl)silane | 0 |
| Butyldimethyl(1H—1,2,4-triazol-1-ylmethyl)silane | 0 |
| Dimethyl(4-methylphenyl)(1H—1,2,4-triazol-1-ylmethyl)silane | 0 |
| (4-Bromophenyl)dimethyl(1H—1,2,4-triazol-1-ylmethyl)silane | 90 |
| (1,1'-Biphenyl-4-yl)dimethyl(1H—1,2,4-triazol-1-ylmethyl)silane | 90 |
| (4-Chlorophenyl)dimethyl(1H—1,2,4-triazol-1-ylmethyl)silane | 0G[A] |
| Butyl(4-chlorophenyl)methyl(1H—1,2,4-triazol-1-ylmethyl)silane | 0 |
| Dimethyl(1-naphthalenyl)(1H—1,2,4-triazol-1-ylmethyl)silane | 0 |
| (3,4-Dichlorophenyl)dimethyl(1H—1,2,4-triazol-1-ylmethyl)silane | 90 |
| Dimethyl(4-phenoxyphenyl)(1H—1,2,4-triazol-1-ylmethyl)silane | 0 |
| Dimethyl(4-methoxyphenyl)(1H—1,2,4-triazol-1-ylmethyl)silane | 90 |
| (2,4-Dichlorophenyl)dimethyl(1H—1,2,4-triazol-1-ylmethyl)silane | 90 |
| bis(4-Chlorophenyl)(methyl)(1H—1,2,4-triazol-1-ylmethyl)silane | 80 |
| (1H—1,2,4-Triazol-1-ylmethyl)triphenylsilane | 0 |
| Methyldiphenyl(1H—1,2,4-triazol-1-ylmethyl)silane | 80 |
| (1,1'-Biphenyl-4-yl)dimethyl(4H—1,2,4-triazol-4-ylmethyl)silane | 100 |
| bis(4-Fluorophenyl)(methyl)1H—1,2,4-triazol-1-ylmethyl)silane | 100 |
| Dimethyl(4-fluorophenyl)(1H—1,2,4-triazol-1-ylmethyl)silane | 90 |
| Dimethyl(4-methylthiophenyl)(1H—1,2,4-triazol-1-ylmethyl)silane | 80 |
| Dimethyl(1H—1,2,4-triazol-1-ylmethyl)(4-trifluoromethylphenyl)-silane | 50 |
| Dimethyl(1H—1,2,4-triazol-1-ylmethyl)(3-trifluoromethylphenyl)-silane | 0 |
| [4-(1,1-Dimethylethyl)phenyl]dimethyl(1H—1,2,4-triazol-1-ylmethyl)silane | 60 |
| Dimethyl(1H—1,2,4-triazol-1-ylmethyl)(2-trifluoromethylphenyl)-silane | 0 |
| (2-Methoxyphenyl)dimethyl(1H— 1,2,4-triazol-1-ylmethyl)silane | 70 |
| Butyl(2,4-dichlorophenyl)methyl(1H—1,2,4-triazol-1-ylmethyl)silane | 100 |
| bis(2,4-Dichlorophenyl)(methyl)(1H—1,2,4-triazol-1-ylmethyl)silane | 80 |
| (2,4-Dichlorophenyl)methyl(phenyl)-(1H—1,2,4-triazol-1-ylmethyl)silane | 0 |
| (4-Chlorophenyl)methyl(phenyl)(1H—1,2,4-triazol-1-ylmethyl)silane | 90 |
| (4-Fluorophenyl)methyl(phenyl)(1H—1,2,4-triazol-1-ylmethyl)silane | 90 |
| Butyl(methyl)phenyl(1H—1,2,4-triazol-1-ylmethyl)silane | 0 |
| (2,3-Dimethoxyphenyl)dimethyl(1H—1,2,4-triazol-1-ylmethyl)silane | 0 |
| (2,6-Dimethoxyphenyl)dimethyl(1H—1,2,4-triazol-1-ylmethyl)silane | 0 |
| Dodecyl(dimethyl)(1H—1,2,4-triazol- | 0 |

TABLE 5-continued

| Compound | % Control of Southern Corn Leaf Blight |
|---|---|
| 1-ylmethyl)silane | |
| (2-Chlorophenyl)dimethyl(1H—1,2,4-triazol-1-ylmethyl)silane | 100 |
| [4-(4-Chlorophenoxy)phenyl]dimethyl-(1H—1,2,4-triazol-1-ylmethyl)silane | 50 |
| (3,5-Dichlorophenyl)dimethyl(1H—1,2,4-triazol-1-ylmethyl)silane | 40 |
| (1,1'-Biphenyl-4-yl)butyl(methyl)-(1H—1,2,4-triazol-1-ylmethyl)silane | 50 |
| Butyl(4-fluorophenyl)methyl(1H—1,2,4-triazol-1-ylmethyl)silane | 0 |
| Dibutyl(methyl)(1H—1,2,4-triazol-1-ylmethyl)silane | 0 |
| bis(1,1'-Biphenyl-4-yl)(methyl)(1H—1,2,4-triazol-1-ylmethyl)silane | 0 |
| (1,1'-Biphenyl-4-yl)methyl(phenyl)-(1H—1,2,4-triazol-1-ylmethyl)silane | 90 |
| (1,1-Dimethylethoxy)methyl(phenyl)-(1H—1,2,4-triazol-1-ylmethyl)silane | 0 |
| Methyl(phenyl)(2-propoxy)(1H—1,2,4-triazol-1-ylmethyl)silane | 0 |
| [bis(4-Methoxyphenyl)]methyl(1H—1,2,4-triazol-1-ylmethyl)silane | 90 |
| (1,1'-Biphenyl-2-yl)dimethyl(1H—1,2,4-triazol-1-ylmethyl)silane | 90 |
| (1,1'-Biphenyl-3-yl)dimethyl(1H—1,2,4-triazol-1-ylmethyl)silane | 100 |
| 2-Chlorophenyl(methyl)phenyl(1H—1,2,4-triazol-1-ylmethyl)silane | 100 |
| 4-Bromophenyl(methyl)phenyl(1H—1,2,4-triazol-1-ylmethyl)silane | 80 |
| [bis(2-Chlorophenyl)] methyl(1H—1,2,4-triazol-1-ylmethyl)silane | 60 |
| Dimethyl(4-methylsulfonylphenyl)(1H—1,2,4-triazol-1-ylmethyl)silane | 0 |
| Cyclohexy(dimethyl)(1H—1,2,4-triazol-1-ylmethyl)silane | 50 |
| [bis(4-Bromophenyl)]methyl(1H—1,2,4-triazol-1-ylmethyl)silane | 0 |
| (1,1'-Biphenyl-4-yl)dimethyl(1H—1,2,4-triazol-1-ylmethyl)silane, 4-dodecylbenzenesulfonic acid salt | 100 |
| (1,1'-Biphenyl-4-yl)dimethyl(1H—1,2,4-triazol-1-ylmethyl)silane, 1:1 complex with cuprous chloride | 100 |
| (1,1'-Biphenyl-4-yl)dimethyl(1H—1,2,4-triazol-1-ylmethyl)silane, 1:1 complex with zinc (II) chloride | 90 |
| (1,1'-Biphenyl-4-yl)dimethyl(1H—1,2,4-triazol-1-ylmethyl)silane, 1:1 complex with manganous sulfate | 100 |
| 2-Chlorophenyl(4-chlorophenyl methyl-(1H—1,2,4-triazol-1-ylmethyl)silane | 60 |
| Phenyl[bis(2-propoxy)](1H—1,2,4-triazol-1-ylmethyl)silane | 0 |
| 2-Chlorophenyl(dimethyl)(1H—1,2,4-triazol-1-ylmethyl)silane | 0 |
| [bis(4-Fluorophenyl)]methyl(1H—1,2,4-triazol-1-ylmethyl)silane, 1:1 complex with cuprous chloride | 0 |
| [bis(4-Fluorophenyl)]methyl(1H—1,2,4-triazol-1-ylmethyl)silane, 2:1 complex with cupric chloride | 0 |
| bis(4-Chlorophenyl)hydroxy(1H—1,2,4-triazol-1-ylmethyl)silane | 90 |
| bis(4-Fluorophenyl)hydroxy(1H—1,2,4-triazol-1-ylmethyl)silane | 100 |
| tris(4-Chlorophenyl)(1H-1,2,4-triazol-1-ylmethyl)silane | 0 |
| tris(4-Fluorophenyl)(1H—1,2,4-triazol-1-ylmethyl)silane | 0 |
| bis(4-Chlorophenyl)hydroxy(4H—1,2,4-triazol-4-ylmethyl)silane | 80 |
| Oxybis[bis(4-fluorophenyl)(1H—1,2,4-triazol-1-ylmethyl)silane] | 97 |
| (1,1'-Biphenyl-4-yl)methyl(2-propoxy)-(1H—1,2,4-triazol-1-ylmethyl)silane | 90 |
| (3-Chlorophenyl)dimethyl(1H—1,2,4-triazol-1-ylmethyl)silane | 0 |
| (1,1'-Biphenyl-4-yl)hydroxy(methyl)-(1H—1,2,4-triazol-1-ylmethyl)silane | 0 |
| (1,1'-Biphenyl-4-yl)(4-fluorophenyl)-methyl(1H—1,2,4-triazol-1-ylmethyl)-silane | 80 |
| Dimethyl(4-trifluoromethoxyphenyl)(1H—1,2,4-triazol-1-ylmethyl)silane | 80 |
| (4'-Bromo-1,1'-biphenyl-4-yl)dimethyl-(1H—1,2,4-triazol-1-ylmethyl)silane | 70 |
| (1,1'-Biphenyl-4-yl)dimethyl(5-methyl-1H—1,2,4-triazol-1-ylmethyl)silane | 80 |
| (1,1'-Biphenyl-4-yl)dimethyl(1H—1,2,4-triazol-1-ylmethyl)silane, 1:1 complex with cupric chloride | 80 |
| (1,1'-Biphenyl-4-yl)dimethyl(1H—1,2,4-triazol-1-ylmethyl)silane, 2:1 complex with cupric chloride | 80 |
| Methyl[bis(4-methylphenyl)](1H—1,2,4-triazol-1-ylmethyl)silane | 0 |
| Dimethyl(octadecyl)(1H—1,2,4-triazol-1-ylmethyl)silane | 0 |
| (4-Fluorophenyl)methyl(2-propoxy)(1H—1,2,4-triazol-1-ylmethyl)silane | 0 |
| (1,1-Dimethylethoxy)[bis(4-fluorophenyl)](1H—1,2,4-triazol-1-ylmethyl)-silane | 0 |

[A] G = growth reduction.

EXAMPLE 84

The compounds of the previous examples were again dissolved in acetone in an amount equal to 6% of the final volume and then suspended at a concentration of 100 ppm in purified water containing 250 ppm of the surfactant TREM 014 (polyhydric alcohol esters). These suspensions were sprayed to the point of run-off on peanut seedlings. The following day, the plants were inoculated with a spore suspension of *Cercospora arachidicola,* causal agent of peanut early leafspot, and incubated in a saturated humidity chamber at 27° for 24 hours and then in a growth room for an additional 14 days, when disease ratings were made. The results are shown in the following table. Treated plants from successful treatments had few or no leafspots while the untreated plants had numerous leafspots.

TABLE 6

| Compound | % Control Peanut Easly Leafspot |
|---|---|
| (Dimethyl)phenyl(1,2,4-triazol-1-ylmethyl)silane | 0 |
| Ethyldimethyl(1H—1,2,4-triazol-1-ylmethyl)silane | 0 |
| Butyldimethyl(1H—1,2,4-triazol-1-ylmethyl)silane | 0 |
| Dimethyl(4-methylphenyl)(1H—1,2,4-triazol-1-ylmethyl silane | 0 |
| (4-Bromophenyl)dimethyl(1H—1,2,4-triazol-1-ylmethyl)silane | 0 |
| (1,1'-Biphenyl-4-yl)dimethyl(1H—1,2,4-triazol-1-ylmethyl silane | 100 |
| (4-Chlorophenyl)dimethyl(1H—1,2,4-triazol-1-ylmethyl)silane | 90 |
| Butyl(4-chlorophenyl)methyl(1H—1,2,4-triazol-1-ylmethyl)silane | 0 |
| Dimethyl(1-naphthalenyl)(1H—1,2,4-triazol-1-ylmethyl)silane | 90 |
| 3,4-Dichlorophenyl)dimethyl(1H—1,2,4-triazol-1-ylmethyl)silane | 0 |
| Dimethyl(4-phenoxyphenyl)(1H—1,2,4-triazol-1-ylmethyl)silane | 0 |
| Dimethyl(4-methoxyphenyl)(1H—1,2,4-triazol-1-ylmethyl)silane | 0 |

TABLE 6-continued

| Compound | % Control Peanut Easly Leafspot |
|---|---|
| (2,4-Dichlorophenyl)dimethyl(1H—1,2,4-triazol-1-ylmethyl)silane | 100 |
| bis(4-Chlorophenyl)(methyl)(1H—1,2,4-triazol-1-ylmethyl)silane | 100 |
| (1H—1,2,4-Triazol-1-ylmethyl)triphenylsilane | 0 |
| Methyldiphenyl(1H—1,2,4-triazol-1-ylmethyl)silane | 100 |
| (1,1'-Biphenyl-4-yl)dimethyl(4H—1,2,4-triazol-4-ylmethyl)silane | 0 |
| bis(4-Fluorophenyl)(methyl)(1H—1,2,4-triazol-1-ylmethyl)silane | 100 |
| Dimethyl(4-Fluorophenyl)(1H—1,2,4-triazol-1-ylmethyl) silane | 50 |
| Dimethyl(4-methylthiophenyl)(1H—1,2,4-triazol-1-ylmethyl)silane | 0 |
| Dimethyl(1H—1,2,4-triazol-1-ylmethyl)(4-trifluoromethylphenyl)-silane | 0 |
| Dimethyl(1H—1,2,4-triazol-1-ylmethyl)(3-trifluoromethylphenyl)-silane | 0 |
| [4-(1,1-Dimethylethyl)phenyl]dimethyl(1H—1,2,4-triazol-1-ylmethyl)silane | 35 |
| Dimethyl(1H—1,2,4-triazol-1-ylmethyl)(2-trifluoromethylphenyl)-silane | 25[A] |
| (2-Methoxyphenyl)dimethyl(1H— 1,2,4-triazol-1-ylmethyl)silane | 0 |
| Butyl(2,4-dichlorophenyl)methyl(1H—1,2,4-triazol-1-ylmethyl)silane | 100 |
| bis(2,4-Dichlorophenyl)(methyl)(1H—1,2,4-triazol-1-ylmethyl)silane | 100 |
| (2,4-Dichlorophenyl)methyl(phenyl)-(1H—1,2,4-triazol-1-ylmethyl)silane | 100 |
| (4-Chlorophenyl)methyl(phenyl)(1H—1,2,4-triazol-1-ylmethyl)silane | 100 |
| (4-Fluorophenyl)methyl(phenyl)(1H—1,2,4-triazol-1-ylmethyl)silane | 100 |
| Butyl(methyl)phenyl(1H—1,2,4-triazol-1-ylmethyl)silane | 0 |
| (2,3-Dimethoxyphenyl)dimethyl(1H—1,2,4-triazol-1-ylmethyl)silane | 0 |
| (2,6-Dimethoxyphenyl)dimethyl(1H—1,2,4-triazol-1-ylmethyl)silane | 0 |
| (2-Chlorophenyl)dimethyl(1H—1,2,4-triazol-1-ylmethyl)silane | 30 |
| [4-(4-Chlorophenoxy)phenyl]dimethyl-(1H—1,2,4-triazol-1-ylmethyl)silane | 0 |
| (3,5-Dichlorophenyl)dimethyl(1H—1,2,4-triazol-1-ylmethyl)silane | 0 |
| (1,1'-Biphenyl-4-yl)butyl(methyl)-(1H—1,2,4-triazol-1-ylmethyl)silane | 100 |
| Butyl(4-fluorophenyl)methyl(1H—1,2,4-triazol-1-ylmethyl)silane | 0 |
| Dibutyl(methyl)(1H—1,2,4-triazol-1-ylmethyl)silane | 0 |
| bis(1,1'-Biphenyl-4-yl)(methyl)(1H—1,2,4-triazol-1-ylmethyl)silane | 80 |
| (1,1'-Biphenyl-4-yl)methyl(phenyl)-(1H—1,2,4-triazol-1-ylmethyl)silane | 100 |
| (1,1-Dimethylethoxy)methyl(phenyl)-(1H—1,2,4-triazol-1-ylmethyl)silane | 0 |
| Methyl(phenyl)(2-propoxy)(1H—1,2,4-triazol-1-ylmethyl)silane | 0 |
| [bis(4-Methoxyphenyl)]methyl(1H—1,2,4-triazol-1-ylmethyl)silane | 30 |
| (1,1'-Biphenyl-2-yl)dimethyl(1H—1,2,4-triazol-1-ylmethyl)silane | 100 |
| (1,1'-Biphenyl-3-yl)dimethyl(1H—1,2,4-triazol-1-ylmethyl)silane | 90 |
| 2-Chlorophenyl(methyl)phenyl(1H—phenyl(1H—1,2,4-triazol-1-ylmethyl)silane | 100 |
| 4-Bromophenyl(methyl)phenyl(1H—1,2,4-triazol-1-ylmethyl)silane | 100 |
| [bis(2-Chlorophenyl)]methyl(1H—1,2,4-triazol-1-ylmethyl)silane | 100 |
| Dimethyl(4-methylsufonylphenyl)(1H—1,2,4-triazol-1-ylmethyl)silane | 0 |
| Cyclohexyl(dimethyl)(1H—1,2,4-triazol-1-ylmethyl)silane | 0 |
| [bis(4-Bromophenyl)]methyl(1H—1,2,4-triazol-1-ylmethyl)silane | 100 |
| (1,1'-Biphenyl-4-yl)dimethyl(1H—1,2,4-triazol-1-ylmethyl)silane, 4-dodecylbenzenesulfonic acid salt | 100 |
| (1,1'-Biphenyl-4-yl)dimethyl(1H—1,2,4-triazol-1-ylmethyl)silane, 1:1 complex with cuprous chloride | 100 |
| (1,1'-Biphenyl-4-yl)dimethyl(1H—1,2,4-triazol-1-ylmethyl)silane, 1:1 complex with zinc (II) chloride | 100 |
| (1,1'-Biphenyl-4-yl)dimethyl(1H—1,2,4-triazol-1-ylmethyl)silane, 1:1 complex with manganous sulfate | 100 |
| 2-Chlorophenyl(4-chlorophenyl)methyl-(1H—1,2,4-triazol-1-ylmethyl)silane | 90 |
| Phenyl[bis(2-propoxy)](1H—1,2,4-triazol-1-ylmethyl)silane | 0 |
| 2-Chlorophenyl(dimethyl)(1H—1,2,4-triazol-1-ylmethyl)silane | 0 |
| [bis(4-Fluorophenyl)]methyl(1H—1,2,4-triazol-1-ylmethyl)silane, 1:1 complex with cuprous chloride | 100 |
| [bis(4-Fluorophenyl)]methyl(1H—1,2,4-triazol-1-ylmethyl)silane, 2:1 complex with cupric chloride | 100 |
| bis(4-Chlorophenyl)hydroxy(1H—1,2,4-triazol-1-ylmethyl)silane | 100 |
| bis(4-Fluorophenyl)hydroxy(1H—1,2,4-triazol-1-ylmethyl)silane | 100 |
| tris(4-Chlorophenyl)(1H—1,2,4-triazol-1-ylmethyl)silane | 0 |
| tris(4-Fluorophenyl)(1H—1,2,4-triazol-1-ylmethyl)silane | 90 |
| bis(4-Chlorophenyl)hydroxy(4H—1,2,4-triazol-1-ylmethyl)silane | 100 |
| Oxybis[bis(4-fluorophenyl)(1H—1,2,4-triazol-1-ylmethyl)silane] | 93[B] |
| (1,1'-Biphenyl-4-yl)methyl(2-propoxy)-(1H—1,2,4-triazol-1-ylmethyl)silane | 100 |
| (3-Chlorophenyl)dimethyl(1H—1,2,4-triazol-1-ylmethyl)silane | 0 |
| (1,1'-Biphenyl-4-yl)hydroxy(methyl)-(1H—1,2,4-triazol-1-ylmethyl)silane | 100 |
| (1,1'-Biphenyl-4-yl)(4-fluorophenyl)-methyl(1H—1,2,4-triazol-1-ylmethyl)-silane | 100 |
| Dimethyl(4-trifluoromethoxyphenyl)(1H—1,2,4-triazol-1-ylmethyl)silane | 50 |
| (4'-Bromo-1,1'-biphenyl-4-yl)dimethyl-(1H—1,2,4-triazol-1-ylmethyl)silane | 100 |
| (1,1'-Biphenyl-4-yl)dimethyl(5-methyl-1H—1,2,4-triazol-1-ylmethyl)silane | 100 |
| (1,1'-Biphenyl-4-yl)dimethyl(1H—1,2,4-triazol-1-ylmethyl)silane, 1:1 complex with cupric chloride | 100 |
| (1,1'-Biphenyl-4-yl)dimethyl(1H—1,2,4-triazol-1-ylmethyl)silane, 2:1 complex with cupric chloride | 100 |
| Methyl[bis(4-methylphenyl)](1H—1,2,4-triazol-1-ylmethyl)silane | 0 |
| Dimethyl(octadecyl)(1H—1,2,4-triazol-1-ylmethyl)silane | 0 |
| bis(4-Fluorophenyl)methyl[1-(1H—1,2,4-triazol-1-yl)ethyl]silane | 100 |

[A]Compound applied at a concentration of 400 ppm.
[B]Compound applied at a concentration of 20 ppm.

EXAMPLE 85

Compounds of the previous examples were again dissolved in acetone in an amount equal to 6% of the final volume and then suspended at a concentration of 80 ppm in purified water containing 250 ppm of the surfactant TREM 014 (polyhydric alcohol esters). This suspension was sprayed to the point of run-off on bean seedlings. The following day, the plants were inoculated with a spore suspension of the fungus *Uromyces phaseoli*, causal agent of bean rust, and incubated in a saturated humidity chamber at 20° for 24 hours and then in a greenhouse for 7 days. Disease ratings were then made. Percent disease control is shown in the following table. Treated plants from successful treatments had few or no rust pustules in contrast to untreated plants which were covered with rust pustules. Phytotoxicity in the form of growth reduction was observed in association with disease control for some treated plants.

TABLE 7

| Compound | % Control Bean Rust |
|---|---|
| (1,1'-Biphenyl-4-yl)dimethyl(1H—1,2,4-triazol-1-ylmethyl)silane | 100 |
| (2,4-Dichlorophenyl)dimethyl(1H—1,2,4-triazol-1-ylmethyl)silane | 30G[A] |
| bis(4-Chlorophenyl)(methyl)(1H—1,2,4-triazol-1-ylmethyl)silane | 100G |
| (4-Chlorophenyl)methyl(phenyl)(1H—1,2,4-triazol-1-ylmethyl)silane | 98[B] |
| (4-Fluorophenyl)methyl(phenyl)(1H—1,2,4-triazol-1-ylmethyl)silane | 100[B] |
| bis(4-Fluorophenyl)(methyl)(1H—1,2,4-triazol-1-ylmethyl)silane | 98[B] |

[A]G = growth reduction.
[B]compound applied at a concentration of 16 ppm.

EXAMPLE 86

Several compounds of the previous examples were again dissolved in acetone in an amount equal to 5% of the final volume and then suspended at a concentration of 100 ppm in purified water containing 700 ppm of the surfactant TREM 014 (polyhydric alcohol esters). Canned peach halves were dipped in this suspension for three minutes and then placed to air dry in sterile containers. Upon drying, the peach halves were inoculated with two pieces of *Monilinia fructicola mycelium*, causal agent of stone fruit brown rot, and incubated in the sterile containers for five days. At that time the radii of the colonies' growth were measured on each peach. Colonies on treated peaches did not grow or grew only a few milliliters in diameter while those growing on untreated peaches covered the entire surface of the peach. Percent disease control (percent growth inhibition of colonies on treated peaches as compared to that of colonies on untreated peaches) is expressed in the table below.

TABLE 8

| Compound | % Control Brown Rot |
|---|---|
| (Dimethyl)phenyl(1,2,4-triazol-1-ylmethyl)silane | 89 |
| (Butyl)dimethyl(1H—1,2,4-triazol-1-ylmethyl)silane | 95 |
| (1,1'-Biphenyl-4-yl)dimethyl(1H—1,2,4-triazol-1-ylmethyl)silane | 100 |
| Butyl(4-chlorophenyl)methyl(1H—1,2,4 triazol-1-ylmethyl)silane | 98 |
| Dimethyl(4-methoxyphenyl)(1H—1,2,4-triazol-1-ylmethyl silane | 97 |
| (2,4-Dichlorophenyl)dimethyl(1H—1,2,4-triazol-1-ylmethyl)silane | 100 |
| bis(4-Chlorophenyl)(methyl)(1H—1,2,4-triazol-1-ylmethyl)silane | 95 |
| (1,1'-Biphenyl-4-yl)dimethyl(4H—1,2,4-triazol-4-ylmethyl)silane | 96 |
| bis(4-Fluorophenyl)(methyl)(1H—1,2,4-triazol-1-ylmethyl)silane | 100 |

TABLE 8-continued

| Compound | % Control Brown Rot |
|---|---|
| Butyl)2,4-dichlorophenyl methyl(1H—1,2,4-triazol-1-ylmethyl)silane | 98 |
| (4-Chlorophenyl)methyl(phenyl)(1H—1,2,4-triazol-1-ylmethyl)silane | 70 |
| (4-Fluorophenyl)methyl(phenyl)(1H—1,2,4-triazol-1-ylmethyl)silane | 90 |
| (1,1'-Biphenyl-4-yl)butyl(methyl)-(1H—1,2,4-triazol-1-ylmethyl)silane | 0 |
| Butyl(4-fluorophenyl)methyl(1H—1,2,4-triazol-1-ylmethyl)silane | 100 |
| Dibutyl(methyl)(1H—1,2,4-triazol-1-ylmethyl)silane | 81 |

EXAMPLE 87

The compounds of the previous examples were again dissolved in acetone in an amount equal to 6% of the final volume and then suspended at a concentration of 100 ppm in purified water containing 250 ppm of the surfactant TREM 014 (polyhydric alcohol esters). This suspension was sprayed to the point of run-off on rice seedlings. The following day, the plants were inoculated with a mixture of bran and the mycelium of *Rhizoctonia solani*, causal agent of sheath blight of rice, and incubated in a growth room for 7 days. Disease ratings were then made. Percent disease control is shown in the following table. Treated plants from successful treatments had little sheath blight in contrast to untreated plants which were covered with sheath blight.

TABLE 9

| Compound | % Control of Rice Sheath Blight |
|---|---|
| (1,1'-Biphenyl-4-yl)dimethyl-(1H—1,2,4-triazol-1-ylmethyl)-silane | 40 |
| Butyl(4-chlorophenyl)methyl(1H—1,2,4-triazol-1-ylmethyl)silane | 0 |
| Dimethyl(1-naphthalenyl)(1H—1,2,4-triazol-1-ylmethyl)silane | 0 |
| (3,4-Dichlorophenyl)dimethyl(1H—1,2,4-triazol-1-ylmethyl)silane | 80 |
| Dimethyl(4-phenoxyphenyl)(1H—1,2,4-triazol-1-ylmethyl)silane | 0 |
| Dimethyl(4-methoxyphenyl)(1H—1,2,4-triazol-1-ylmethyl)silane | 0 |
| (2,4-Dichlorophenyl)dimethyl(1H—1,2,4-triazol-1-ylmethyl)silane | 0 |
| bis(4-Chlorophenyl)(methyl)(1H—0 1,2,4-triazol-1-ylmethyl)silane | |
| (1H—1,2,4-Triazol-1-ylmethyl)triphenylsilane | 0 |
| Methyldiphenyl(1H—1,2,4-triazol-1-ylmethyl)silane | 0 |
| (1,1'-Biphenyl-4-yl)dimethyl(4H—1,2,4-triazol-4-ylmethyl)silane | 0 |
| bis(4-Fluorophenyl)(methyl)(1H—1,2,4-triazol-1-ylmethyl)silane | 80 |
| Dimethyl(4-fluorophenyl)(1H—1,2,4-triazol-1-ylmethyl)silane | 0 |
| Dimethyl(4-methylthiophenyl)(1H—1,2,4-triazol-1-ylmethyl)silane | 0 |
| Dimethyl(1H—1,2,4-triazol-1-ylmethyl)(4-trifluoromethylphenyl)silane | 0 |
| Dimethyl(1H—1,2,4-triazol-1-ylmethyl)(3-trifluoromethylphenyl)silane | 0 |
| [4-(1,1-Dimethylethyl)phenyl]dimethyl(1H—1,2,4-triazol-1-ylmethyl)silane | 90 |
| (2-Methoxyphenyl)dimethyl(1H—1,2,4-triazol-1-ylmethyl)silane | 0 |
| Butyl(2,4-dichlorophenyl)methyl(1H— | 50 |

TABLE 9-continued

| Compound | % Control of Rice Sheath Blight |
|---|---|
| 1,2,4-triazol-1-ylmethyl)silane | |
| bis(2,4-Dichlorophenyl)(methyl)(1H—1,2,4-triazol-1-ylmethyl)silane | 0 |
| (2,4-Dichlorophenyl)methyl(phenyl)-(1H—1,2,4-triazol-1-ylmethyl)silane | 0 |
| (4-Chlorophenyl)methyl(phenyl)(1H—1,2,4-triazol-1-ylmethyl)silane | 90 |
| (4-Fluorophenyl)methyl(phenyl)(1H—1,2,4-triazol-1-ylmethyl)silane | 80 |
| Butyl(methyl)phenyl(1H—1,2,4-triazol-1-ylmethyl)silane | 90 |
| (2,3-Dimethoxyphenyl)dimethyl(1H—1,2,4-triazol-1-ylmethyl)silane | 0 |
| (2,6-Dimethoxyphenyl)dimethyl(1H—1,2,4-triazol-1-ylmethyl)silane | 0 |
| (2-Chlorophenyl)dimethyl(1H—1,2,4-triazol-1-ylmethyl)silane | 0 |
| [4-(4-Chlorophenoxy)phenyl]dimethyl-(1H—1,2,4-triazol-1-ylmethyl)silane | 0 |
| (3,5-Dichlorophenyl)dimethyl(1H—1,2,4-triazol-1-ylmethyl)silane | 0 |
| (1,1'-Biphenyl-4-yl)butyl(methyl)-(1H—1,2,4-triazol-1-ylmethyl)silane | 80 |
| Butyl(4-fluorophenyl)methyl(1H—1,2,4-triazol-1-ylmethyl)silane | 80 |
| Dibutyl(methyl)(1H—1,2,4-triazol-1-ylmethyl)silane | 0 |
| bis(1,1'-Biphenyl-4-yl)(methyl)(1H—1,2,4-triazol-1-ylmethyl)silane | 90 |
| (1,1'-Biphenyl-4-yl)methyl(phenyl)-(1H—1,2,4-triazol-1-ylmethyl)silane | 0 |
| (1,1-Dimethylethoxy)methyl(phenyl)-(1H—1,2,4-triazol-1-ylmethyl)silane | 0 |
| Methyl(phenyl)(2-propoxy)(1H—1,2,4-triazol-1-ylmethyl)silane | 0 |
| [bis(4-Methoxyphenyl)]methyl(1H—1,2,4-triazol-1-ylmethyl)silane | 80 |
| (1,1'-Biphenyl-2-yl)dimethyl(1H—1,2,4-triazol-1-ylmethyl)silane | 0 |
| (1,1'-Biphenyl-3-yl)dimethyl(1H—1,2,4-triazol-1-ylmethyl)silane | 0 |
| 2-Chlorophenyl(methyl)phenyl(1H—1,2,4-triazol-1-ylmethyl)silane | 90 |
| 4-Bromophenyl(methyl)phenyl(1H—1,2,4-triazol-1-ylmethyl)silane | 90 |
| [bis(2-Chlorophenyl)]methyl(1H—1,2,4-triazol-1-ylmethyl)silane | 60 |
| Dimethyl(4-methylsulfonylphenyl)1H—1,2,4-triazol-1-ylmethyl)silane | 0 |
| Cyclohexyl(dimethyl)(1H—1,2,4-triazol-1-ylmethyl)silane | 0 |
| [bis(4-Bromophenyl)]methyl 1H—1,2,4-triazol-1-ylmethyl)silane | 0 |
| (1,1'-Biphenyl-4-yl)dimethyl(1H—1,2,4-triazol-1-ylmethyl)silane, 4-dodecylbenzenesulfonic acid salt | 0 |
| (1,1'-Biphenyl-4-yl)dimethyl(1H—1,2,4-triazol-1-ylmethyl)silane, 1:1 complex with cuprous chloride | 90 |
| (1,1'-Biphenyl-4-yl)dimethyl(1H—1,2,4-triazol-1-ylmethyl)silane, 1:1 complex with zinc (II) chloride | 90 |
| (1,1'-Biphenyl-4-yl)dimethyl(1H—1,2,4-triazol-1-ylmethyl)silane, 1:1 complex with manganous sulfate | 0 |
| 2-Chlorophenyl(4-chlorophenyl)methyl-(1H—1,2,4-triazol-1-ylmethyl)silane | 70 |
| Phenyl[bis(2-propoxy)](1H—1,2,4-triazol-1-ylmethyl)silane | 0 |
| 2-Chlorophenyl(dimethyl)(1H—1,2,4-triazol-1-ylmethyl)silane | 0 |
| [bis(4-Fluorophenyl)]methyl(1H—1,2,4-triazol-1-ylmethyl)silane, 1:1 complex with cuprous chloride | 90 |
| [bis(4-Fluorophenyl)]methyl(1H—1,2,4-triazol-1-ylmethyl)silane, 2:1 complex with cupric chloride | 0 |
| bis(4-Chlorophenyl)hydroxy(1H—1,2,4-triazol-1-ylmethyl)silane | 0 |
| bis(4-Fluorophenyl)hydroxy(1H—1,2,4-triazol-1-ylmethyl)silane | 0 |
| tris(4-Chlorophenyl)(1H—1,2,4-triazol-1-ylmethyl)silane | 0 |
| tris(4-Fluorophenyl)(1H—1,2,4-triazol-1-ylmethyl)silane | 0 |
| bis(4-Chlorophenyl)hydroxy(4H—1,2,4-triazol-4-ylmethyl)silane | 0 |
| Oxybis[bis(4-fluorophenyl)1H—1,2,4-triazol-1-ylmethyl)silane] | 0 |
| (1,1'-Biphenyl-4-yl)methyl(2-propoxy)-(1H—1,2,4-triazol-1-ylmethyl)silane | 0 |
| (3-Chlorophenyl)dimethyl(1H—1,2,4-triazol-1-ylmethyl)silane | 0 |
| (1,1'-Biphenyl-4-yl)hydroxy(methyl)-(1H—1,2,4-triazol-1-ylmethyl)silane | 0 |
| (1,1'-Biphenyl-4-yl)(4-fluorophenyl)-methyl(1H—1,2,4-triazol-1-ylmethyl)-silane | 0 |
| Dimethyl(4-trifluoromethoxyphenyl)(1H—1,2,4-triazol-1-ylmethyl)silane | 0 |
| (4'-Bromo-1,1'-biphenyl-4-yl)dimethyl-(1H—1,2,4-triazol-1-ylmethyl)silane | 90 |
| (1,1'-Biphenyl)dimethyl(5-methyl-1H—1,2,4-triazol-1-ylmethyl)silane | 0 |
| (1,1'-Biphenyl-4-yl)dimethyl(1H—1,2,4-triazol-1-ylmethyl)silane, 1:1 complex with cupric chloride | 0 |
| (1,1'-Biphenyl-4-yl)dimethyl(1H—1,2,4-triazol-1-ylmethyl)silane, 2:1 complex with cupric chloride | 80 |
| Methyl[bis(4-methylphenyl)](1H—1,2,4-triazol-1-ylmethyl)silane | 30 |
| Dimethyl(octadecyl)(1H—1,2,4-triazol-1-ylmethyl)silane | 0 |
| bis(4-Fluorophenyl)mehyl[1-(1H—1,2,4-triazol-1-yl)ethyl]silane | 80 |

EXAMPLE 88

The compounds of the previous examples were again dissolved in acetone in an amount equal to 6% of the final volume and then suspended at a concentration of 100 ppm in purified water containing 250 ppm of the surfactant TREM 014 (polyhydric alcohol esters). These suspensions were sprayed to the point of run-off on rice seedlings. The following day, the plants were inoculated with a spore suspension of *Pyricularia oryzae,* causal agent of rice blast, and incubated in a saturated humidity chamber at 28° C. for 24 hours and then in a growth room for an additional 7 days, when disease ratings were made. Percent disease control is shown in the following table. Treated plants from successful treatments had no or few lesions while the untreated plants had numerous lesions on each leaf.

TABLE 10

| Compound | % Control of Rice Blast |
|---|---|
| (Dimethyl)phenyl(1,2,4-triazol-1-ylmethyl)silane | 0 |
| Ethyldimethyl(1H—1,2,4-triazol-1-ylmethyl)silane | 0 |
| Butyldimethyl(1H—1,2,4-triazol-1-ylmethyl)silane | 0 |
| Dimethyl(4-methylphenyl)(1H—1,2,4-triazol-1-ylmethyl)silane | 0 |
| (4-Bromophenyl)dimethyl(1H—1,2,4-triazol-1-ylmethyl)silane | 0 |
| (1,1'-Biphenyl-4-yl)dimethyl(1H—1,2,4-triazol-1-ylmethyl)silane | 0 |
| (4-Chlorophenyl)dimethyl(1H—1,2,4-triazol-1-ylmethyl)silane | 0 |
| Butyl(4-chlorophenyl)methyl(1H—1,2,4-triazol-1-ylmethyl)silane | 0 |

TABLE 10-continued

| Compound | % Control of Rice Blast |
|---|---|
| Dimethyl(1-naphthalenyl)(1H—1,2,4-triazol-1-ylmethyl)silane | 70 |
| (3,4-Dichlorophenyl)dimethyl(1H—1,2,4-triazol-1-ylmethyl)silane | 0 |
| Dimethyl(4-phenoxyphenyl)(1H—1,2,4-triazol-1-ylmethyl)silane | 0 |
| Dimethyl(4-methoxyphenyl)(1H—1,2,4-triazol-1-ylmethyl)silane | 0 |
| (2,4-Dichlorophenyl)dimethyl(1H—1,2,4-triazol-1-ylmethyl)silane | 0 |
| bis(4-Chlorophenyl)(methyl)(1H—1,2,4-triazol-1-ylmethyl)silane | 90 |
| (1H—1,2,4-Triazol-1-ylmethyl)triphenylsilane | 0 |
| Methyldiphenyl(1H—1,2,4-triazol-1-ylmethyl)silane | 0 |
| (1,1'-Biphenyl-4-yl)dimethyl(4H—1,2,4-triazol-4-ylmethyl)silane | 0 |
| bis(4-Fluorophenyl)(methyl)(1H—1,2,4-triazol-1-ylmethyl)silane | 100 |
| Dimethyl(4-fluorophenyl)(1H—1,2,4-triazol-1-ylmethyl)silane | 0 |
| Dimethyl(4-methylthiophenyl)(1H—1,2,4-triazol-1-ylmethyl)silane | 0 |
| Dimethyl(1H—1,2,4-triazol-1-ylmethyl)(4-trifluoromethylphenyl)silane | 0 |
| Dimethyl(1H—1,2,4-triazol-1-ylmethyl)(3-trifluoromethylphenyl)silane | 0 |
| [4-(1,1-Dimethylethyl)phenyl]dimethyl(1H—1,2,4-triazol-1-ylmethyl)silane | 90 |
| (2-Methoxyphenyl)dimethyl(1H—1,2,4-triazol-1-ylmethyl)silane | 0 |
| Butyl(2,4-dichlorophenyl)methyl(1H—1,2,4-triazol-1-ylmethyl)silane | 0 |
| bis(2,4-Dichlorophenyl)(methyl)(1H—1,2,4-triazol-1-ylmethyl)silane | 0 |
| (2,4-Dichlorophenyl)methyl(phenyl)-(1H—1,2,4-triazol-1-ylmethyl)silane | 0 |
| (4-Chlorophenyl)methyl(phenyl)(1H—1,2,4-triazol-1-ylmethyl)silane | 100 |
| (4-Fluorophenyl)methyl(phenyl)(1H—1,2,4-triazol-1-ylmethyl)silane | 0 |
| Butyl(methyl)phenyl(1H—1,2,4-triazol-1-ylmethyl)silane | 90 |
| (2,3-Dimethoxyphenyl)dimethyl(1H—1,2,4-triazol-1-ylmethyl)silane | 0 |
| (2,6-Dimethoxyphenyl)dimethyl(1H—1,2,4-triazol-1-ylmethyl)silane | 0 |
| (2-Chlorophenyl)dimethyl(1H—1,2,4-triazol-1-ylmethyl)silane | 100 |
| [4-(4-Chlorophenoxy)phenyl]dimethyl-(1H—1,2,4-triazol-1-ylmethyl)silane | 0 |
| (3,5-Dichlorophenyl)dimethyl(1H—1,2,4-triazol-1-ylmethyl)silane | 0 |
| (1,1'-Biphenyl-4-yl)butyl(methyl)-(1H—1,2,4-triazol-1-ylmethyl)silane | 100 |
| Butyl(4-fluorophenyl)methyl(1H—1,2,4-triazol-1-ylmethyl)silane | 100 |
| Dibutyl(methyl)(1H—1,2,4-triazol-1-ylmethyl)silane | 80 |
| bis(1,1'Biphenyl-4-yl)(methyl)(1H—1,2,4-triazol-1-ylmethyl)silane | 100 |
| (1,1'Biphenyl-4-yl)methyl(phenyl)-(1H—1,2,4-triazol-1-ylmethyl)silane | 0 |
| (1,1-Dimethylethoxy)methyl(phenyl)-(1H—1,2,4-triazol-1-ylmethyl)silane | 0 |
| Methyl(phenyl)(2-propoxy)(1H—1,2,4-triazol-1-ylmethyl)silane | 0 |
| [bis(4-Methoxyphenyl)]methyl(1H—1,2,4-triazol-1-ylmethyl)silane | 0 |
| (1,1'-Biphenyl-2-yl)dimethyl(1H—1,2,4-triazol-1-ylmethyl)silane | 90 |
| (1,1'-Biphenyl-3-yl)dimethyl(1H—1,2,4-triazol-1-ylmethyl)silane | 0 |
| 2-Chlorophenyl(methyl)phenyl(1H—1,2,4-triazol-1-ylmethyl)silane | 100 |
| 4-Bromophenyl(methyl)phenyl(1H—1,2,4-triazol-1-ylmethyl)silane | 80 |
| [bis(2-Chlorophenyl)]methyl(1H—1,2,4-triazol-1-ylmethyl)silane | 90 |
| Dimethyl(4-methylsulfonylphenyl)(1H—1,2,4-triazol-1-ylmethyl)silane | 70 |
| [bis(4-Bromophenyl)]methyl(1H—1,2,4-triazol-1-ylmethyl)silane | 90 |
| (1,1'-Biphenyl-4-yl)dimethyl(1H—1,2,4-triazol-1-ylmethyl)silane, 4-dodecylbenzenesulfonic acid salt | 80 |
| (1,1'-Biphenyl-4-yl)dimethyl(1H—1,2,4-triazol-1-ylmethyl)silane, 1:1 complex with cuprous chloride | 100 |
| (1,1'-Biphenyl-4-yl)dimethyl(1H—1,2,4-triazol-1-ylmethyl)silane, 1:1 complex with zinc (II) chloride | 100 |
| (1,1'-Biphenyl-4-yl)dimethyl(1H—1,2,4-triazol-1-ylmethyl)silane, 1:1 complex with manganous sulfate | 0 |
| [bis(4-Fluorophenyl)]methyl(1H—1,2,4-triazol-1-ylmethyl)silane, 1:1 complex with cuprous chloride | 90 |
| [bis(4-Fluorophenyl)]methyl(1H—1,2,4-triazol-1-ylmethyl)silane, 2:1 complex with cupric chloride | 100 |
| bis(4-Chlorophenyl)hydroxy(1H—1,2,4-triazol-1-ylmethyl)silane | 0 |
| bis(4-Fluorophenyl)hydroxy(1H—1,2,4-triazol-1-ylmethyl)silane | 0 |
| tris(4-Chlorophenyl)(1H—1,2,4-triazol-1-ylmethyl)silane | 0 |
| tris(4-Fluoropenyl)(1H—1,2,4-triazol-1-ylmethyl)silane | 0 |
| bis(4-Chlorophenyl)hydroxy(4H—1,2,4-triazol-4-ylmethyl)silane | 0 |
| Oxybis[bis(4-fluorophenyl)(1H—1,2,4-triazol-1-ylmethyl)silane] | 50 |
| (1,1'-Biphenyl-4-yl)methyl(2-propoxy)-(1H—1,2,4-triazol-1-ylmethyl)silane | 0 |
| (3-Chlorophenyl)dimethyl(1H—1,2,4-triazol-1-ylmethyl)silane | 0 |
| (1,1'-Biphenyl-4-yl)hydroxy(methyl)-(1H—1,2,4-triazol-1-ylmethyl)silane | 0 |
| Dimethyl(4-trifluoromethoxyphenyl)(1H—1,2,4-triazol-1-ylmethyl)silane | 0 |
| (4'-Bromo-1,1'-biphenyl-4-yl)dimethyl-(1H—1,2,4-triazol-1-ylmethyl)silane | 90 |
| (1,1'-Biphenyl-4-yl)dimethyl(5-methyl-1H—1,2,4-triazol-1-ylmethyl)silane | 0 |
| (1,1'-Biphenyl-4-yl)dimethyl(1H—1,2,4-triazol-1-ylmethyl)silane, 1:1 complex with cupric chloride | 100 |
| (1,1'-Biphenyl-4-yl)dimethyl(1H—1,2,4-triazol-1-ylmethyl)silane, 2:1 complex with cupric chloride | 0 |
| Methyl[bis(4-methylphenyl)](1H—1,2,4-triazol-1-ylmethyl)silane | 80 |
| Dimethyl(octadecyl)(1H—1,2,4-triazol-1-ylmethyl)silane | 0 |
| bis(4-Fluorophenyl)methyl[1-(1H—1,2,4-triazol-1-yl)ethyl]silane | 0 |

EXAMPLE 89

The compounds of the previous examples were again dissolved in acetone in an amount equal to 6% of the final volume and then suspended at a concentration of 100 ppm in purified water containing 250 ppm of the surfactant TREM 014 (polyhydric alcohol esters). These suspensions were sprayed to the point of run-off on tomato seedlings. The following day, the plants were inoculated with a spore suspension of *Phytophthora infestans,* causal agent of tomato late blight, and incubated in a saturated humidity chamber at 20° C. for 24 hours and then in a growth room for an additional 7 days, when disease ratings were made. Percent disease control is shown in the following table. Treated plants from successful treatments had no or few lesions while the untreated plants had numerous lesions on each leaf.

TABLE 11

| Compound | % Control of Tomato Late Blight |
|---|---|
| (Dimethyl)phenyl(1,2,4-triazol-1-ylmethyl)silane | 0 |
| Ethyldimethyl(1H—1,2,4-triazol-1-ylmethyl)silane | 0 |
| Butyldimethyl(1H—1,2,4-triazol-1-ylmethyl)silane | 0 |
| Dimethyl(4-methylphenyl)(1H—1,2,4-triazol-1-ylmethyl)silane | 0 |
| (4-Bromophenyl)dimethyl(1H—1,2,4-triazol-1-ylmethyl)silane | 0 |
| (1,1'-Biphenyl-4-yl)dimethyl(1H—1,2,4-triazol-1-ylmethyl)silane | 0 |
| (4-Chlorophenyl)dimethyl(1H—1,2,4-triazol-1-ylmethyl)silane | 0 |
| Butyl(4-chlorophenyl)methyl(1H—1,2,4-triazol-1-ylmethyl)silane | 0 |
| Dimethyl(1-naphthalenyl)(1H—1,2,4-triazol-1-ylmethyl)silane | 0 |
| (3,4-Dichlorophenyl)dimethyl(1H—1,2,4-triazol-1-ylmethyl)silane | 0 |
| Dimethyl(4-phenoxyphenyl)(1H—1,2,4-triazol-1-ylmethyl)silane | 50 |
| Dimethyl(4-methoxyphenyl)(1H—1,2,4-triazol-1-ylmethyl)silane | 0 |
| (2,4-Dichlorophenyl)dimethyl(1H—1,2,4-triazol-1-ylmethyl)silane | 0 |
| bis(4-Chlorophenyl)(methyl)(1H—1,2,4-triazol-1-ylmethyl)silane | 0 |
| (1H—1,2,4-Triazol-1-ylmethyl)triphenylsilane | 0 |
| Methyldiphenyl(1H—1,2,4-triazol-1-ylmethyl)silane | 0 |
| (1,1'-Biphenyl-4-yl)dimethyl(4H—1,2,4-triazol-4-ylmethyl)silane | 0 |
| (bis(4-Fluorophenyl)(methyl)(1H—1,2,4-triazol-1-ylmethyl)silane | 0 |
| Dimethyl(4-fluorophenyl)(1H—1,2,4-triazol-1-ylmethyl)silane | 0 |
| Dimethyl(4-methylthiophenyl)(1H—1,2,4-triazol-1-ylmethyl)silane | 0 |
| Dimethyl(1H—1,2,4-triazol-1-ylmethyl)(4-trifluoromethylphenyl)silane | 0 |
| Dimethyl(1H—1,2,4-triazol-1-ylmethyl)(3-trifluoromethylphenyl)silane | 0 |
| [4-(1,1-Dimethylethyl)phenyl]dimethyl(1H—1,2,4-triazol-1-ylmethyl)silane | 0 |
| (2-Methoxyphenyl)dimethyl(1H—1,2,4-triazol-1-ylmethyl)silane | 0 |
| Butyl(2,4-dichlorophenyl)methyl(1H—1,2,4-triazol-1-ylmethyl)silane | 0 |
| bis(2,4-Dichlorophenyl)(methyl)(1H—1,2,4-triazol-1-ylmethyl)silane | 0 |
| (2,4-Dichlorophenyl)methyl(phenyl)(1H—1,2,4-triazol-1-ylmethyl)silane | 0 |
| (4-Chlorophenyl)methyl(phenyl)(1H—1,2,4-triazol-1-ylmethyl)silane | 0 |
| (4-Fluorophenyl)methyl(phenyl)(1H—1,2,4-triazol-1-ylmethyl)silane | 0 |
| Butyl(methyl)phenyl(1H—1,2,4-triazol-1-ylmethyl)silane | 0 |
| (2,3-Dimethoxyphenyl)dimethyl(1H—1,2,4-triazol-1-ylmethyl)silane | 0 |
| (2,6-Dimethoxyphenyl)dimethyl(1H—1,2,4-triazol-1-ylmethyl)silane | 0 |
| (2-Chlorophenyl)dimethyl(1H—1,2,4-triazol-1-ylmethyl)silane | 0 |
| [4-(4-Chlorophenoxy)phenyl]dimethyl(1H—1,2,4-triazol-1-ylmethyl)silane | 50 |
| (3,5-Dichlorophenyl)dimethyl(1H—1,2,4-triazol-1-ylmethyl)silane | 0 |
| (1,1'-Biphenyl-4-yl)butyl(methyl)(1H—1,2,4-triazol-1-ylmethyl)silane | 0 |
| Butyl(4-fluorophenyl)methyl(1H—1,2,4-triazol-1-ylmethyl)silane | 0 |
| Dibutyl(methyl)(1H—1,2,4-triazol-1-ylmethyl)silane | 0 |
| bis(1,1'-Biphenyl-4-yl)(methyl)(1H—1,2,4-triazol-1-ylmethyl)silane | 0 |
| (1,1'-Biphenyl-4-yl)methyl(phenyl)(1H—1,2,4-triazol-1-ylmethyl)silane | 0 |
| (1,1-Dimethylethoxy)methyl(phenyl)(1H—1,2,4-triazol-1-ylmethyl)silane | 0 |
| Methyl(phenyl)(2-propoxy)(1H—1,2,4-triazol-1-ylmethyl)silane | 0 |
| [bis(4-Methoxyphenyl)]methyl(1H—1,2,4-triazol-1-ylmethyl)silane | 0 |
| (1,1'-Biphenyl-2-yl)dimethyl(1H—1,2,4-triazol-1-ylmethyl)silane | 50 |
| (1,1'-Biphenyl-3-yl)dimethyl(1H—1,2,4-triazol-1-ylmethyl)silane | 0 |
| 2-Chlorophenyl(methyl)phenyl(1H—1,2,4-triazol-1-ylmethyl)silane | 0 |
| 4-Bromophenyl(methyl)phenyl(1H—1,2,4-triazol-1-ylmethyl)silane | 0 |
| [bis(2-Chlorophenyl)]methyl(1H—1,2,4-triazol-1-ylmethyl)silane | 0 |
| Dimethyl(4-methylsulfonylphenyl)(1H—1,2,4-triazol-1-ylmethyl)silane | 0 |
| Cyclohexyl(dimethyl)(1H—1,2,4-triazol-1-ylmethyl)silane | 0 |
| [bis(4-Bromophenyl)]methyl(1H—1,2,4-triazol-1-ylmethyl)silane | 0 |
| (1,1'-Biphenyl-4-yl)dimethyl(1H—1,2,4-triazol-1-ylmethyl)silane, 4-dodecylbenzenesulfonic acid salt | 60 |
| (1,1'-Biphenyl-4-yl)dimethyl(1H—1,2,4-triazol-1-ylmethyl)silane, 1:1 complex with cuprous chloride | 100 |
| (1,1'-Biphenyl-4-yl)dimethyl(1H—1,2,4-triazol-1-ylmethyl)silane, 1:1 complex with zinc (II) chloride | 90 |
| (1,1'-Biphenyl-4-yl)dimethyl(1H—1,2,4-triazol-1-ylmethyl)silane, 1:1 complex with manganous sulfate | 0 |
| 2-Chlorophenyl(4-chlorophenyl)methyl(1H—1,2,4-triazol-1-ylmethyl)silane | 0 |
| Phenyl[bis(2-propoxy)](1H—1,2,4-triazol-1-ylmethyl)silane | 0 |
| 2-Chlorophenyl(dimethyl)(1H—1,2,4-triazol-1-ylmethyl)silane | 0 |
| [bis(4-Fluorophenyl)]methyl(1H—1,2,4-triazol-1-ylmethyl)silane, 1:1 complex with cuprous chlroide | 0 |
| [bis(4-Fluorophenyl)]methyl(1H—1,2,4-triazol-1-ylmethyl)silane, 2:1 complex with cupric chloride | 40 |
| bis(4-Chlorophenyl)hydroxy(1H—1,2,4-triazol-1-ylmethyl)silane | 0 |
| bis(4-Fluorophenyl)hydroxy(1H—1,2,4-triazol-1-ylmethyl)silane | 0 |
| tris(4-Chlorophenyl)(1H—1,2,4-triazol-1-ylmethyl)silane | 0 |
| tris(4-Fluorophenyl)(1H—1,2,4-triazol-1-ylmethyl)silane | 0 |
| bis(4-Chlorophenyl)hydroxy(4H—1,2,4-triazol-4-ylmethyl)silane | 0 |
| Oxybis[bis(4-fluorophenyl)(1H—1,2,4-triazol-1-ylmethyl)silane] | 0 |
| (1,1'Biphenyl-4-yl)methyl(2-propoxy)-(1H—1,2,4-triazol-1-ylmethyl)silane | 0 |
| (3-Chlorophenyl)dimethyl(1H—1,2,4-triazol-1-ylmethyl)silane | 0 |
| (1,1'-Biphenyl-4-yl)hydroxy(methyl)-(1H—1,2,4-triazol-1-ylmethyl)silane | 0 |
| (1,1'-Biphenyl-4-yl)(4-fluorophenyl)-methyl(1H—1,2,4-triazol-1-ylmethyl)-silane | 0 |
| Dimethyl(4-trifluoromethoxyphenyl)(1H—1,2,4-triazol-1-ylmethyl)silane | 0 |
| (4'-Bromo-1,1'-biphenyl-4-yl)imethyl-(1H—1,2,4-triazol-1-ylmethyl)silane | 30 |
| (1,1'-Biphenyl-4-yl)dimethyl(5-methyl-1H—1,2,4-triazol-1-ylmethyl)silane | 80 |

TABLE 11-continued

| Compound | % Control of Tomato Late Blight |
|---|---|
| (1,1'-Biphenyl-4-yl)dimethyl(1H—1,2,4-triazol-1-ylmethyl)silane, 1:1 complex with cupric chloride | 90 |
| (1,1'-Biphenyl-4-yl)dimethyl(1H—1,2,4-triazol-1-ylmethyl)silane, 2:1 complex with cupric chloride | 0 |
| Methyl[bis(4-methylphenyl)](1H—1,2,4-triazol-1-ylmethyl)silane | 0 |
| Dimethyl(octadecyl)(1H—1,2,4-triazol-1-ylmethyl)silane | 0 |
| bis(4-Fluorophenyl)methyl[1-(1H—1,2,4-triazol-1-yl)ethyl]silane | 0 |

EXAMPLE 90

Compounds of the previous examples were incorporated into 45° C. standard strength V-8 agar at a concentration of 200.0 ppm. The amended media were then dispensed into petri dishes and allowed to solidify. Plugs approximately 4 $mm^2$ from agar cultures of 5 Phytophthora species: *Phytophthora cinnamomi, P. cactorum, P. infestans, P. palmivora,* and *P. parasitica* var. *nicotianae* were placed on the media and incubated at 22° C. for 6 days. Colonies whose radial growth extended 1 mm or less were considered to be controlled by a compound when compared to colonies whose radial growth extended 15 mm or more when growing on unamended media. The number of Phytophthora species controlled by certain compounds of this invention are listed in the table below.

TABLE 12

| Compound | No. of 5 Phytophthora species controlled in vitro |
|---|---|
| (1,1'-Biphenyl-4-yl)dimethyl(1H—1,2,4-triazol-1-ylmethyl)silane | 0 |
| (Butyl)dimethyl(1H—1,2,4-triazol-1-ylmethyl)silane | 1 |
| (3,4-Dichlorophenyl)dimethyl(1H—1,2,4-triazol-1-ylmethyl)silane | 2 |
| (2,4-Dichlorophenyl)dimethyl(1H—1,2,4-triazol-1-ylmethyl)silane | 0 |
| bis(4-Chlorophenyl)(methyl)(1H—1,2,4-triazol-1-ylmethyl)silane | 0 |
| Dimethyl(4-phenoxyphenyl)(1H—1,2,4-triazol-1-ylmethyl)silane | 0 |
| bis(4-Fluorophenyl)(methyl)(1H—1,2,4-triazol-1-ylmethyl)silane | 0 |
| Butyl(2,4-dichlorophenyl)methyl-(1H—1,2,4-triazol-1-ylmethyl)-silane | 0 |
| (4-Chlorophenyl)methyl(phenyl)-(1H—1,2,4-triazol-1-ylmethyl)-silane | 0 |
| (4-Fluorophenyl)methyl(phenyl)-(1H—1,2,4-triazol-1-ylmethyl)-silane | 0 |
| [4-(4-Chlorophenoxy)phenyl]dimethyl-(1H—1,2,4-triazol-1-ylmethyl)-silane | 0 |

EXAMPLE 91

Several compounds of the previous examples were incorporated into a proprietary formulation and used to coat cotton seeds at a rate of 2 gm/kg seed. After being thoroughly coated, the seeds were allowed to air dry at room temperature. The cotton seeds were then planted into soil amended with the fungus *Pythium aphanadermatum,* sand, and corn meal at a rate sufficient to kill most untreated seeds. The seeds were held at room temperature for 1 week, after which time disease ratings were made. Percent disease control is shown in the following table. Most or all seeds from successful treatments germinated and produced vigorous seedlings in contrast to untreated seeds which either did not germinate or produced damped off or weak seedlings.

TABLE 13

| Compound | % Control of Pythium on Cotton |
|---|---|
| (Dimethyl)phenyl(1,2,4-triazol-1-ylmethyl silane | 0 |
| Ethyldimethyl(1H—1,2,4-triazol-1-ylmethyl)silane | 48 |
| Butyldimethyl(1H—1,2,4-triazol-1-ylmethyl)silane | 0 |
| Dimethyl(4-methylphenyl)(1H—1,2,4-triazol-1-ylmethyl)silane | 0 |
| (1,1'-Biphenyl-4-yl)dimethyl(1H—1,2,4-triazol-1-ylmethyl)silane | 12 |
| (4-Chlorophenyl)dimethyl(1H—1,2,4-triazol-1-ylmethyl)silane | 53[A] |
| Dimethyl(4-phenoxyphenyl)(1H—1,2,4-triazol-1-ylmethyl)silane | 18[A] |
| Dimethyl(4-methoxyphenyl)(1H—1,2,4-triazol-1-ylmethyl)silane | 0 |
| (2,4-Dichlorophenyl)dimethyl(1H—1,2,4-triazol-1-ylmethyl)silane | 0 |
| bis(4-Chlorophenyl)(methyl)(1H—1,2,4-triazol-1-ylmethyl)silane | 0 |
| Methyldiphenyl(1H—1,2,4-triazol-1-ylmethyl)silane | 0 |
| bis(4-Fluorophenyl)(methyl)(1H—1,2,4-triazol-1-ylmethyl)silane | 0 |
| Butyl(4-fluorophenyl)methyl(1H—1,2,4-triazol-1-ylmethyl)silane | 0 |
| bis(1,1'-Biphenyl-4-yl)methyl(1H—1,2,4-triazol-1-ylmethyl)silane | 0 |
| (1,1'-Biphenyl-4-yl)methyl(phenyl)-(1H—1,2,4-triazol-1-ylmethyl)-silane | 0 |

[A]control at a rate of 0.5 gm/kg seed.

EXAMPLE 92

Several compounds of the previous examples were incorporated into a proprietary formulation and used to coat corn seeds at a rate of 2 gm/kg seed. After being thoroughly coated, the seeds were allowed to air dry at room temperature. The seeds were then planted into soil amended with a mixture of the fungus *Pythium aphanadermatum,* sand, and corn meal at a rate sufficient to kill most untreated seeds. The seeds were held at 49° F. for 2 weeks and then at 70° F. for 1 additional week. After this time disease ratings were made. Percent disease control is shown in the following table. Most or all seeds from successful treatments germinated and produced vigorous seedlings in contrast to untreated seeds which either did not germinate or produced damped off or weak seedlings.

TABLE 14

| Compound | % Control of Pythium on Corn |
|---|---|
| Ethyldimethyl(1H—1,2,4-triazol-1-ylmethyl)silane | 13 |
| Butyldimethyl(1H—1,2,4-triazol-1-ylmethyl)silane | 0 |
| Dimethyl(4-methylphenyl)(1H—1,2,4-triazol-1-ylmethyl)silane | 0 |
| (1,1'-Biphenyl-4-yl)dimethyl(1H—1,2,4-triazol-1-ylmethyl)silane | 30 |
| (4-Chlorophenyl)dimethyl(1H—1,2,4-triazol-1-ylmethyl)silane | 8 |
| Dimethyl(1-naphthalenyl)(1H—1,2,4-triazol-1-ylmethyl)silane | 30 |

TABLE 14-continued

| Compound | % Control of Pythium on Corn |
| --- | --- |
| (3,4-Dichlorophenyl)dimethyl(1H—1,2,4-triazol-1-ylmethyl)silane | 43 |
| Dimethyl(4-phenoxyphenyl)(1H—1,2,4-triazol-1-ylmethyl)silane | 0 |
| Methyldiphenyl(1H—1,2,4-triazol-1-ylmethyl)silane | 0 |
| bis(4-Fluorophenyl)(methyl)(1H—1,2,4-triazol-1-ylmethyl)silane | 0 |
| Butyl(4-fluorophenyl)methyl(1H—1,2,4-triazol-1-ylmethyl)silane | 0 |
| (1,1'-Biphenyl-4-yl)methyl(phenyl)-(1H—1,2,4-triazol-1-ylmethyl)silane | 0 |

What is claimed is:

1. A compound of the formula:

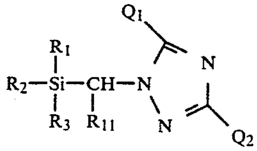

I wherein $Q_1$ and $Q_2$ are independently H or $CH_3$;

$R_1$ is $C_2$–$C_{18}$ alkyl, $C_3$–$C_6$ cycloalkyl, naphthyl, or

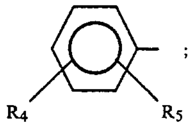

;

where $R_4$ and $R_5$ are independently —H, halogen, —$OCH_3$, —$OCF_3$, —$SCH_3$, —$SO_2CH_3$, phenyl, phenyl substituted with halogen and/or $C_1$–$C_4$ alkyl and/or —$CF_3$, phenoxy, phenoxy substituted with halogen and/or $C_1$–$C_4$ alkyl and/or —$CF_3$, —$CF_3$, $C_1$–$C_4$ alkyl, or cyclohexyl; and $R_2$ and $R_3$ are independently $C_1$–$C_6$ alkyl, $C_3$–$C_6$ cycloalkyl, $OR_6$, or

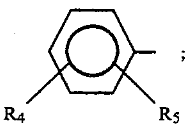

;

where $R_6$ is H, $C_1$–$C_4$ alkyl, or

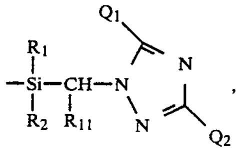

, with the proviso that when both $R_2$ and $R_3$ are $OR_6$, then $R_6$ must be $C_1$–$C_4$ alkyl; or $R_2$ and $R_3$ may be a 1,2- or 1,3- or 1,4-glycol bridge substituted by up to four alkyl groups $R_7$–$R_{10}$ that have a total of up to four carbon atoms

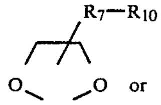

or

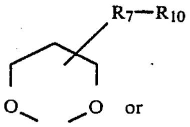

or

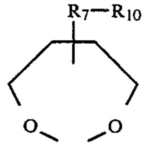

or

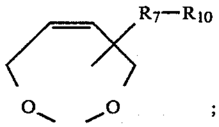

;

$R_{11}$ is H or $C_1$–$C_4$ alkyl;

and fungicidally active metal complexes or protic acid salts of said compounds.

2. A compound of claim 1 wherein $Q_1=Q_2=H$ and $R_{11}$ is H or $CH_3$.

3. A compound of claim 2 wherein $R_1$ is

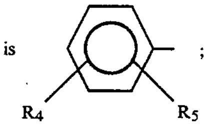

;

and $R_2$ is $C_1$–$C_4$ alkyl or

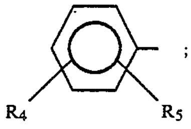

;

and $R_3$ is $C_1$–$C_4$ alkyl or $OR_6$, where $R_6$ is H, $C_1$–$C_4$ alkyl or

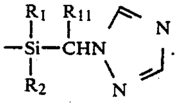

.

4. A compound of claim 3 wherein $R_1$ is

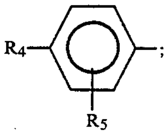

;

where $R_4$ is at the para position of $R_1$, and $R_4$ is H, F, Cl, Br, or phenyl, and $R_5$ is H, F, Cl, or Br; and $R_2$ is

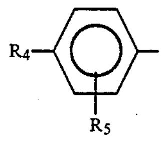

or $C_1$–$C_4$ alkyl; and $R_3$ is $C_1$–$C_4$ alkyl or $OR_6$, where $R_6$ is H, $C_1$–$C_4$ alkyl or

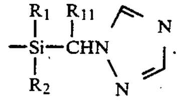

5. The compound of claim 1 which is (1,1′-biphenyl-4-yl)dimethyl(1H-1,2,4-triazol-1-ylmethyl)silane.

6. The compound of claim 1 which is bis(4-fluorophenyl)methyl(1H-1,2,4-triazol-1-ylmethyl)silane.

7. The compound of claim 1 which is bis(4-fluorophenyl)hydroxy(1H-1,2,4-triazol-1-ylmethyl)silane.

8. The compound of claim 1 which is oxybis[bis(4-fluorophenyl)(1H-1,2,4-triazol-1-ylmethyl)silane].

9. The compound of claim 1 which is bis(4-fluorophenyl)methyl[1-(1H-1,2,4-triazol-1-yl)ethyl]silane.

10. The compound of claim 1 which is (4-fluorophenyl)methyl(phenyl)(1H-1,2,4-triazol-1-yl-methyl)silane.

11. The compound of claim 1 which is bis-(4-chlorophenyl)methyl(1H-1,2,4-triazol-1-yl-methyl)silane.

12. The compound of claim 1 which is (4-chlorophenyl)methyl(phenyl)(1H-1,2,4-triazol-1-yl-methyl)silane.

13. A composition suitable for controlling fungus disease which comprises an effective amount of a compound of claim 1 and at least one of the following: surfactant, solid or liquid inert diluent.

14. A composition suitable for controlling fungus disease which comprises an effective amount of a compound of claim 2 and at least one of the following: surfactant, solid or liquid inert diluent.

15. A composition suitable for controlling fungus disease which comprises an effective amount of a compound of claim 3 and at least one of the following: surfactant, solid or liquid inert diluent.

16. A composition suitable for controlling fungus disease which comprises an effective amount of a compound of claim 4 and at least one of the following: surfactant, solid or liquid inert diluent.

17. A composition suitable for controlling fungus disease which comprises an effective amount of the compound of claim 5 and at least one of the following: surfactant, solid or liquid inert diluent.

18. A composition suitable for controlling fungus disease which comprises an effective amount of the compound of claim 6 and at least one of the following: surfactant, solid or liquid inert diluent.

19. A composition suitable for controlling fungus disease which comprises an effective amount of the compound of claim 7 and at least one of the following: surfactant, solid or liquid inert diluent.

20. A composition suitable for controlling fungus disease which comprises an effective amount of the compound of claim 8 and at least one of the following: surfactant, solid or liquid inert diluent.

21. A composition suitable for controlling fungus disease which comprises an effective amount of the compound of claim 9 and at least one of the following: surfactant, solid or liquid inert diluent.

22. A composition suitable for controlling fungus disease which comprises an effective amount of the compound of claim 10 and at least one of the following: surfactant, solid or liquid inert diluent.

23. A composition suitable for controlling fungus disease which comprises an effective amount of the compound of claim 14 and at least one of the following: surfactant, solid or liquid inert diluent.

24. A composition suitable for controlling fungus disease which comprises an effective amount of the compound of claim 15 and at least one of the following: surfactant, solid or liquid inert diluent.

25. A method for controlling fungus disease which comprises applying to the locus of infestation to be protected an effective amount of a compound of claim 1.

26. A method for controlling fungus disease which comprises applying to the locus of infestation to be protected an effective amount of a compound of claim 2.

27. A method for controlling fungus disease which comprises applying to the locus of infestation to be protected an effective amount of a compound of claim 3.

28. A method for controlling fungus disease which comprises applying to the locus of infestation to be protected an effective amount of a compound of claim 4.

29. A method for controlling fungus disease which comprises applying to the locus of infestation to be protected an effective amount of the compound of claim 5.

30. A method for controlling fungus disease which comprises applying to the locus of infestation to be protected an effective amount of the compound of claim 6.

31. A method for controlling fungus disease which comprises applying to the locus of infestation to be protected an effective amount of the compound of claim 7.

32. A method for controlling fungus disease which comprises applying to the locus of infestation to be protected an effective amount of the compound of claim 8.

33. A method for controlling fungus disease which comprises applying to the locus of infestation to be protected an effective amount of the compound of claim 9.

34. A method for controlling fungus disease which comprises applying to the locus of infestation to be protected an effective amount of a compound of claim 13.

35. A method for controlling fungus disease which comprises applying to the locus of infestation to be protected an effective amount of a compound of claim 14.

36. A method for controlling fungus disease which comprises applying to the locus of infestation to be protected an effective amount of a compound of claim 15.

* * * * *